(12) United States Patent
Ma et al.

(10) Patent No.: US 8,603,992 B2
(45) Date of Patent: *Dec. 10, 2013

(54) COMPOSITIONS COMPRISING MG29 NUCLEIC ACIDS, POLYPEPTIDES, AND ASSOCIATED METHODS OF USE

(75) Inventors: Jianjie Ma, Belle Mead, NJ (US); Noah Weisleder, Elizabeth, NJ (US)

(73) Assignee: University of Medicine and Dentistry of New Jersey, Somerset, NJ (US)

(*) Notice: Subject to any disclaimer, the term of this patent is extended or adjusted under 35 U.S.C. 154(b) by 586 days.

This patent is subject to a terminal disclaimer.

(21) Appl. No.: 12/504,331

(22) Filed: Jul. 16, 2009

(65) Prior Publication Data

US 2010/0017901 A1 Jan. 21, 2010

Related U.S. Application Data

(60) Provisional application No. 61/135,325, filed on Jul. 18, 2008, provisional application No. 61/212,275, filed on Apr. 8, 2009.

(51) Int. Cl.
| | | |
|---|---|---|
| *C12N 15/11* | (2006.01) | |
| *A61K 48/00* | (2006.01) | |
| *C07H 21/02* | (2006.01) | |
| *C07H 21/04* | (2006.01) | |

(52) U.S. Cl.
USPC ............... 514/44 A; 514/44 R; 536/24.5

(58) Field of Classification Search
USPC ............................................. 514/44; 536/24.5
See application file for complete search history.

(56) References Cited

U.S. PATENT DOCUMENTS

| | | |
|---|---|---|
| 2003/0170838 A1 | 9/2003 | Mishra et al. |
| 2004/0029116 A1 | 2/2004 | Edinger et al. |
| 2004/0029222 A1 | 2/2004 | Edinger et al. |
| 2005/0181400 A1* | 8/2005 | Monia et al. ................ 435/6 |
| 2011/0034533 A1* | 2/2011 | Ma et al. ................... 514/44 A |

FOREIGN PATENT DOCUMENTS

| | | |
|---|---|---|
| JP | 2006-122048 | 5/2006 |
| WO | WO 02-24733 A2 | 3/2002 |

OTHER PUBLICATIONS

Thornton, Angela. Regulation of Store-Operated Calcium Channel by mitsugumin29 in Skeletal Muscle Aging, Graduate Dissertation dated Jan. 2009, pp. 1-103.*
David Bartel. MicroRNAs: Genomics, Biogenesis, Mechanism, and Function. Cell, 2004. vol. 116:281-294.*
Pan et al. (Journal of Biological Chemistry, 2004 vol. 279, No. 19:19387-19390).*
Komazaki, S., et al., "Abnormal Formation of Sarcoplasmic Reticulum Networks and Triads During Early Development of Skeletal Muscle Cells in Mitsugumin29-Deficient Mice", Dev. Growth Differ., vol. 43(6), p. 717-723(Dec. 2001).
NCBI Accession No. NP_001035799 (Jun. 26, 2007).

(Continued)

*Primary Examiner* — Terra Cotta Gibbs
(74) *Attorney, Agent, or Firm* — McCarter & English, LLP

(57) ABSTRACT

Disclosed herein are compositions and methods for treatment of muscle dysfunction (including sarcopenia) and other diseases involving skeletal muscle, including age-related muscle dysfunction. In addition, the invention relates to therapeutic compositions comprising nucleotides and/or polypeptides of the invention in combination with a pharmaceutically acceptable carrier, wherein the composition facilitates the treatment of skeletal muscle disorder, including those related to thr normal aging process. Moreover, the invention relates to the treatment and/or prevention of pathological conditions associated with altered intracellular Ca2+ regulation and disrupted membrane structure that occurs when the expression levels of MG29 are reduced.

16 Claims, 18 Drawing Sheets

(56) References Cited

OTHER PUBLICATIONS

NCBI Accession No. BC113102 (Oct. 4, 2006).
*ISR and Written Opinion of Int'l Searching Authority* for PCT/US2009/050846.

File history of U.S. Appl. No. 12/794,006.
*Written Opinion of Int'l Searching Authority* for PCT/US2010/037389.

* cited by examiner

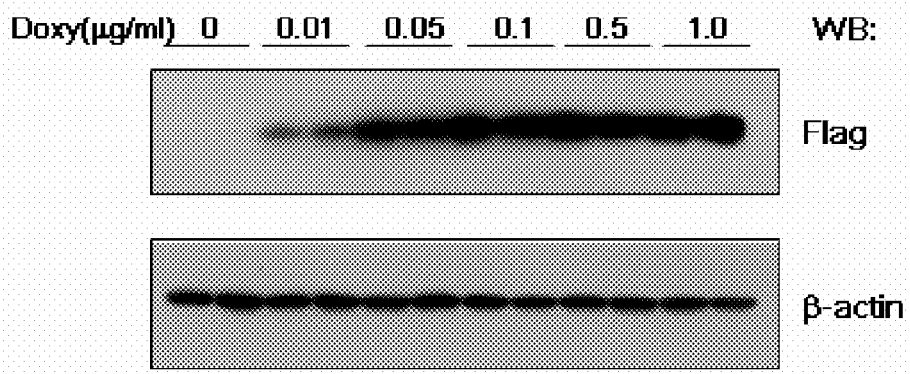
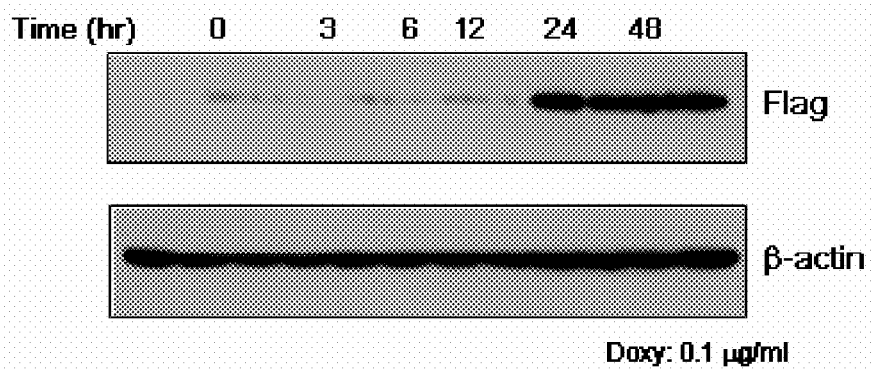
FIGURE 2

(See SEQ ID NO. 28)

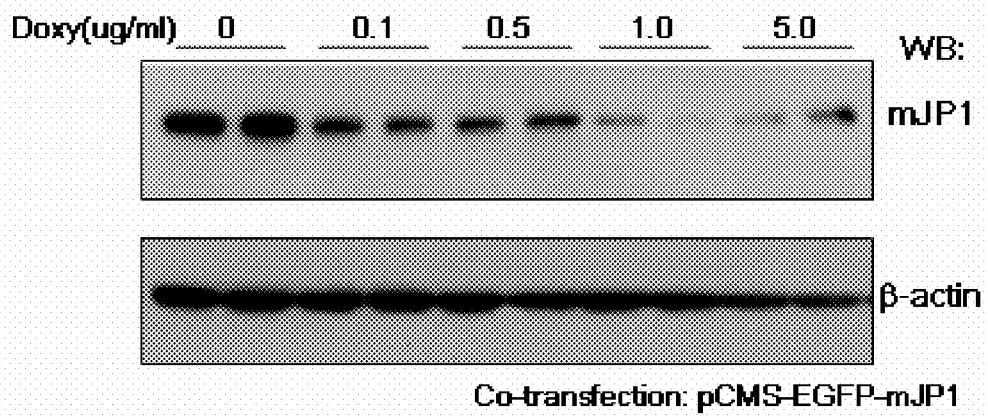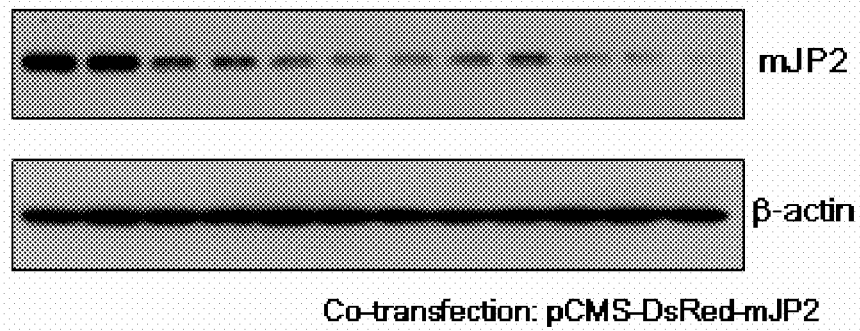
FIGURE 5

A
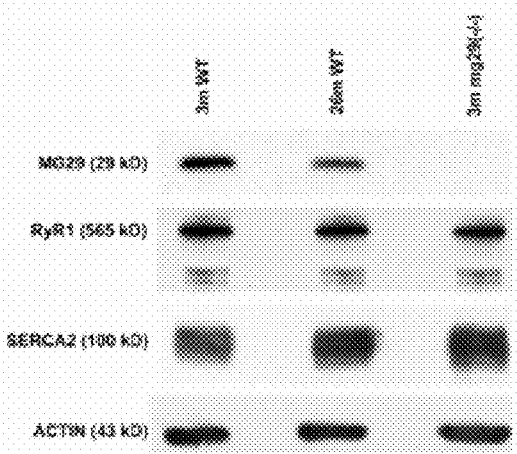
B
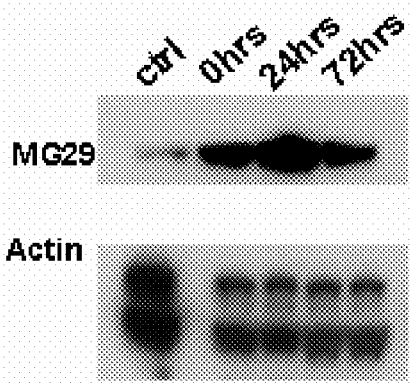
FIGURE 6

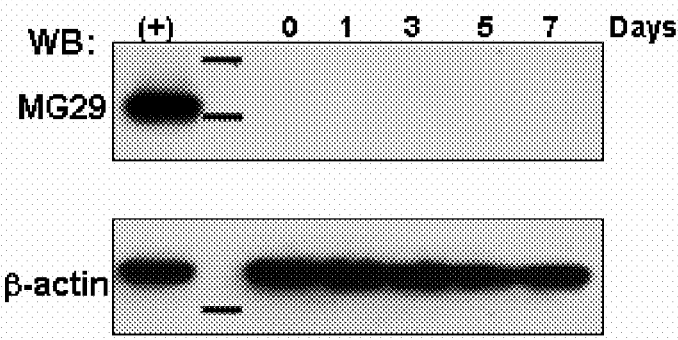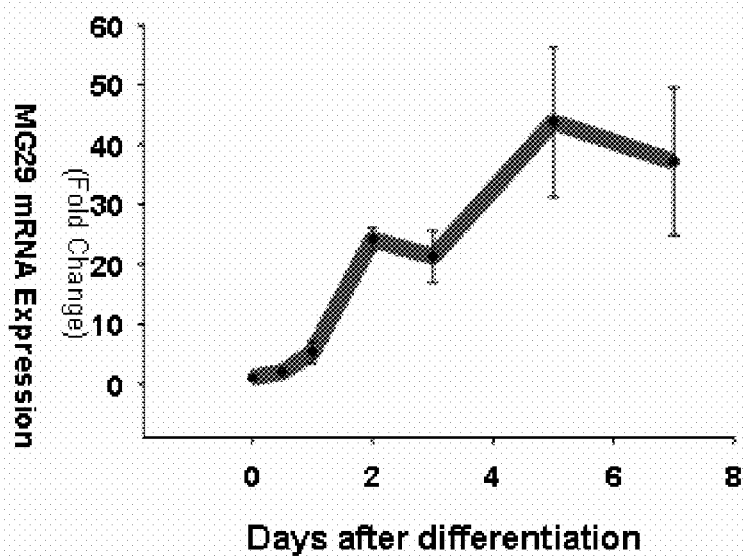
FIGURE 7

Table 1

Features of complete UTR sequences derived from genomic entries annotated in UTRdb [47,48,50].

| | 5' UTR | | | | 3' UTR | | | |
|---|---|---|---|---|---|---|---|---|
| | Number of sequences | Average length | Maximum length | Minimum length | Number of sequences | Average length | Maximum length | Minimum length |
| Humans | 3,208 | 210.2 | 2,803 | 18 | 1,347 | 1,027.7 | 8,555 | 21 |
| Other mammals | 142 | 161.3 | 936 | 20 | 148 | 441.1 | 3,324 | 37 |
| Rodents | 638 | 186.3 | 1,786 | 16 | 457 | 607.3 | 3,354 | 19 |
| Aves | 59 | 326.4 | 620 | 17 | 56 | 621.9 | 3,990 | 21 |
| Other vertebrates | 105 | 184.0 | 1,154 | 15 | 111 | 446.5 | 2,858 | 21 |

MG29
human   ~370    ~2,600
mouse   ~180    ~2,300

MG29 CDS : human 819 bp
          mouse  795 bp

FIGURE 8

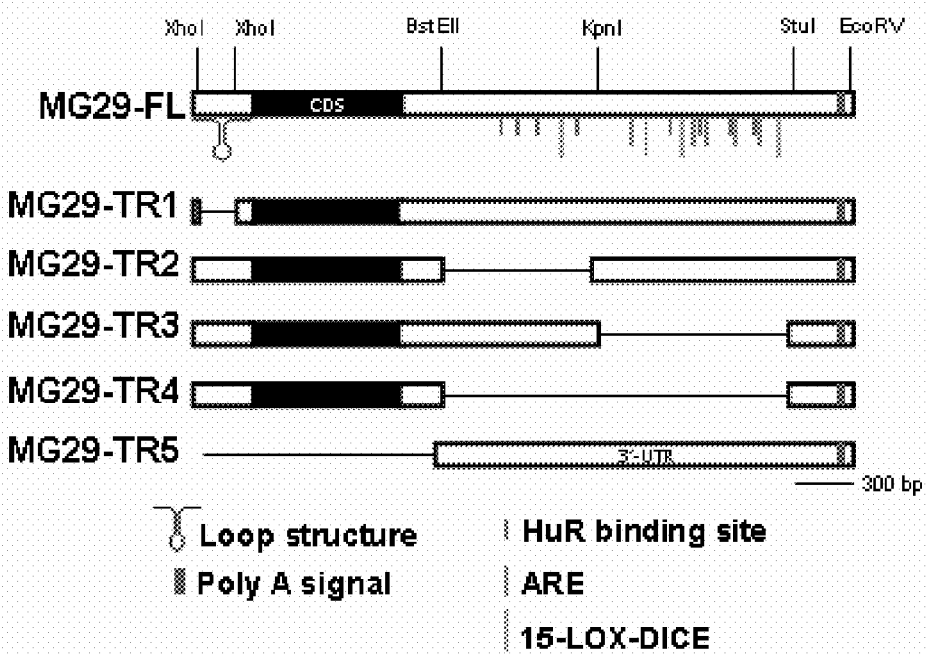
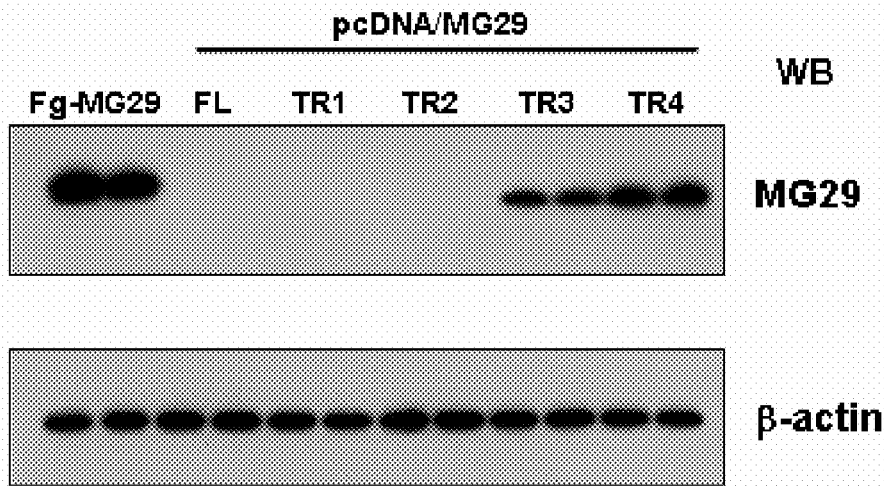
FIGURE 15

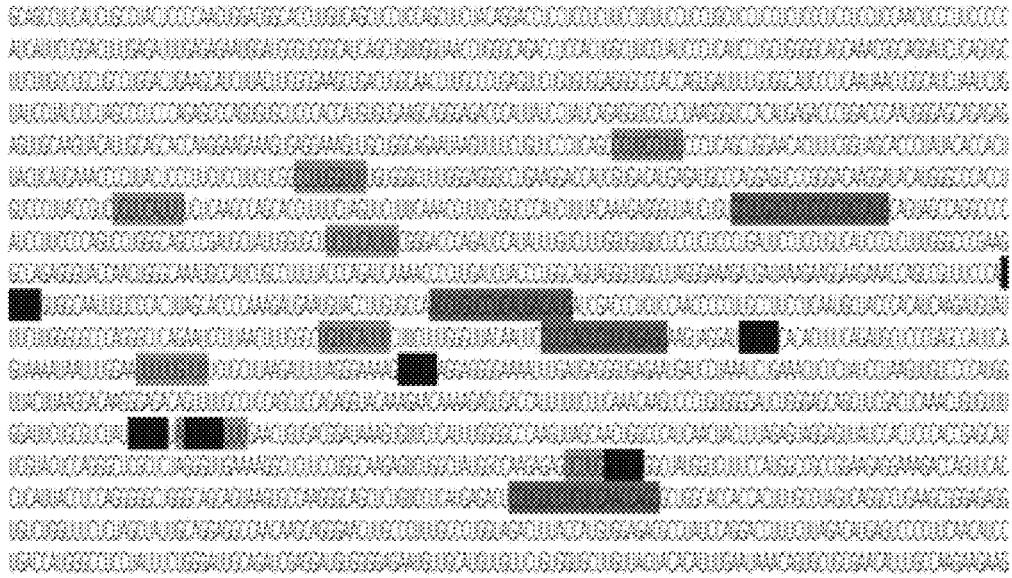

(See SEQ ID NO. 25)

HuR binding site

▓▓▓ HuR regulates the stability and translation of mRNA in the response of the stress such as oxidative stress. (Abdelmohsen et al., (2008) Biol Chem. 389: 243-255; Kuwano and Gorospe (2008) Cell cycle 7: 2640-2642; Adams et al., (2003) J. of Biol. Chem. 278: 44894-44903: Wang et al., (2000) EMBO J. 19: 2340-2350)

▬▬▬ ARE (AU rich Element). ARE is mRNA destabilizing elements

▬▬▬ 15-LOX-DICE (15-LipOXygenase DIfferentiation Control Element)
hnRNP E1 and K inhibit initiation of translation by binding 15-LOX-DICE.
(Ostareck et al., (1997) Cell 89: 597-606;
Reimann et al., (2002) J.of Mol. Biol. 315: 965-974)

FIGURE 16

```
-702 CAGAGTCTTG GACTGTCGCC AGGGCTGGAG          GC
                                       ---------    M00075GATA-1 91.0
                                       ---------    M00076GATA-2 88.9
                                       --------->   M00075GATA-1 86.5
                                       --------     M00077GATA-3 85.0

-652 TCACTGCAAC TTCCACCTCC CGGGTTCAAG CAATTCTCCT

-602 CCTGAGTAGC TGGGATTACA     C     ACCG
                                -----                M00271RUNX1 100.0
                                ---------            M00075GATA-1 89.8
                                                     M00087Ik-2
     --------->                                      M00221SREBP1 87.3
                                                     ---------M00099S8
                                          -          M00159C/EBP 86.2

-552 TGTATTTTTA GTAGAGACGG GGTTTCACTA TGTTGGCC  G
     ----                                            M00099S8
     ------                                          M00101CdxA
                                       ---           M00033       85.1

-502          CTCGTGATCT TCTGGCCTCG GCCTCCCAAA
                                                     M00141Lyf1
                        ---------------              M00087Ik-2    6.8
                                  ---------M00087Ik-2
     ----------                                      M00033       85.1

-452 TGCAGGCGTG AGCCACCAAG CCTGGCCAAT (SEQ ID NO. 27)
     -->                                             M00087Ik-2
```

FIGURE 18

```
SEQUENCE LISTING

<160> NUMBER OF SEQ ID NOS: 28

<210> SEQ ID NO 1
<211> LENGTH: 264
<212> TYPE: PRT
<213> ORGANISM: Mus musculus
<220> FEATURE:
<221> NAME/KEY: MISC_FEATURE
<222> LOCATION: (1)..(264)

<400> SEQUENCE: 1

Met Ser Ser Thr Glu Ser Pro Gly Arg Thr Ser Asp Lys Ser Pro Arg
1               5                   10                  15

Gln Gln Val Asp Arg Leu Leu Leu Gly Leu Arg Trp Gln Arg Leu Glu
            20                  25                  30

Glu Pro Leu Gly Phe Ile Lys Val Leu Gln Trp Leu Phe Ala Ile Phe
        35                  40                  45

Ala Phe Gly Ser Cys Gly Ser Tyr Ser Gly Glu Thr Gly Ala Leu Val
    50                  55                  60

Leu Cys Asn Asn Glu Ala Lys Asp Val Ser Ser Ile Ile Val Leu Phe
65                  70                  75                  80

Gly Tyr Pro Phe Arg Leu Tyr Gln Val Gln Tyr Glu Met Pro Leu Cys
                85                  90                  95

Asp Gln Asp Ser Thr Ser Lys Thr Met Asn Leu Met Gly Asp Phe Ser
            100                 105                 110

Ala Pro Ala Glu Phe Phe Val Thr Leu Gly Ile Phe Ser Phe Phe Tyr
        115                 120                 125

Thr Met Ala Ala Leu Val Ile Tyr Leu Arg Phe His Lys Leu Tyr Thr
    130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175
```

```
Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
            195                 200                 205

Met Gly Leu Ala Asn Leu Ser Val Leu Phe Gly Phe Ile Asn Phe Phe
            210                 215                 220

Leu Trp Ala Gly Asn Cys Trp Phe Val Phe Lys Glu Thr Pro Trp His
225                 230                 235                 240

Gly Gln Gly Gln Asp Gln Gly Gln Gly Pro Ser Gln Glu Ser Ala Ala
                    245                 250                 255

Glu Gln Gly Ala Val Glu Lys Gln
            260

<210> SEQ ID NO 2
<211> LENGTH: 264
<212> TYPE: PRT
<213> ORGANISM: Oryctolagus cuniculus
<220> FEATURE:
<221> NAME/KEY: MISC_FEATURE
<222> LOCATION: (1)..(264)

<400> SEQUENCE: 2

Met Ser Ser Thr Glu Ser Pro Ser Arg Ala Ala Asp Lys Ser Pro Arg
1               5                   10                  15

Gln Gln Val Asp Arg Leu Leu Glu Gly Leu Arg Trp Arg Arg Leu Glu
            20                  25                  30

Glu Pro Leu Gly Phe Ile Lys Val Leu Gln Trp Leu Phe Ala Ile Phe
            35                  40                  45

Ala Phe Gly Ser Cys Gly Ser Tyr Ser Gly Glu Thr Gly Ala Met Val
            50                  55                  60

Arg Cys Asn Asn Glu Ala Lys Asp Val Ser Ser Ile Ile Val Leu Phe
65                  70                  75                  80

Gly Tyr Pro Phe Arg Leu His Arg Ile Glu Tyr Glu Met Pro Leu Cys
                85                  90                  95

Asp Asp Asp Ser Ser Ser Lys Thr Met His Leu Met Gly Asp Phe Ser
            100                 105                 110

Ala Pro Ala Glu Phe Phe Val Thr Leu Gly Ile Phe Ser Phe Phe Tyr
            115                 120                 125

Thr Met Ala Ala Leu Val Val Tyr Leu Arg Phe His Lys Leu Tyr Thr
            130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175

Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
            195                 200                 205

Met Gly Leu Ala Asn Ile Ser Val Leu Phe Gly Phe Ile Asn Phe Phe
            210                 215                 220

Leu Trp Ala Gly Asn Cys Trp Phe Val Phe Lys Glu Thr Pro Trp His
225                 230                 235                 240

Gly Gln Gly Gln Asp Gln Gly Gln Gly Pro Ser Gln Glu Ser Ala Ala
                    245                 250                 255

Glu Gln Gly Ala Val Glu Lys Gln
            260
```

```
<210> SEQ ID NO 3
<211> LENGTH: 272
<212> TYPE: PRT
<213> ORGANISM: Homo sapiens
<220> FEATURE:
<221> NAME/KEY: MISC_FEATURE
<222> LOCATION: (1)..(272)

<400> SEQUENCE: 3

Met Ser Ser Thr Glu Ser Ala Gly Arg Thr Ala Asp Lys Ser Pro Arg
1               5                   10                  15

Gln Gln Val Asp Arg Leu Leu Val Gly Leu Arg Trp Arg Arg Leu Glu
            20                  25                  30

Glu Pro Leu Gly Phe Ile Lys Val Leu Gln Trp Leu Phe Ala Ile Phe
        35                  40                  45

Ala Phe Gly Ser Cys Gly Ser Tyr Ser Gly Glu Thr Gly Ala Met Val
    50                  55                  60

Arg Cys Asn Asn Glu Ala Lys Asp Val Ser Ser Ile Ile Val Ala Phe
65                  70                  75                  80

Gly Tyr Pro Phe Arg Leu His Arg Ile Gln Tyr Glu Met Pro Leu Cys
                85                  90                  95

Asp Glu Glu Ser Ser Ser Lys Thr Met His Leu Met Gly Asp Phe Ser
            100                 105                 110

Ala Pro Ala Glu Phe Phe Val Thr Leu Gly Ile Phe Ser Phe Phe Tyr
        115                 120                 125

Thr Met Ala Ala Leu Val Ile Tyr Leu Arg Phe His Asn Leu Tyr Thr
    130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Ala Trp Gly Lys Gly Leu Thr
                165                 170                 175

Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
        195                 200                 205

Met Gly Leu Ala Asn Ile Ser Val Leu Phe Gly Phe Ile Asn Phe Phe
    210                 215                 220

Leu Trp Ala Gly Asn Cys Trp Phe Val Phe Lys Glu Thr Pro Trp His
225                 230                 235                 240

Gly Gln Gly Gln Gly Gln Asp Gln Asp Gln Asp Gln Asp Gln Gly Gln
                245                 250                 255

Gly Pro Ser Gln Glu Ser Ala Ala Glu Gln Gly Ala Val Glu Lys Gln
            260                 265                 270

<210> SEQ ID NO 4
<211> LENGTH: 236
<212> TYPE: PRT
<213> ORGANISM: Homo sapiens
<220> FEATURE:
<221> NAME/KEY: MISC_FEATURE
<222> LOCATION: (1)..(236)

<400> SEQUENCE: 4

Met Ser Ser Thr Glu Ser Ala Gly Arg Thr Ala Asp Lys Ser Pro Arg
1               5                   10                  15

Gln Gln Val Asp Arg Leu Leu Val Gly Leu Arg Trp Arg Arg Leu Glu
            20                  25                  30

Glu Pro Leu Gly Phe Ile Lys Val Leu Gln Trp Leu Phe Ala Ile Phe
```

```
                35                  40                  45
Ala Phe Gly Ser Cys Gly Ser Tyr Ser Gly Glu Thr Gly Ala Met Val
 50                  55                  60
Arg Cys Asn Asn Glu Ala Lys Asp Val Ser Ser Ile Ile Val Ala Phe
65                  70                  75                  80
Gly Tyr Pro Phe Arg Leu His Arg Ile Gln Tyr Glu Met Pro Leu Cys
                 85                  90                  95
Asp Glu Ser Ser Ser Lys Thr Met His Leu Met Gly Asp Phe Ser
            100                 105                 110
Ala Pro Ala Glu Phe Phe Val Thr Leu Gly Ile Phe Ser Phe Phe Tyr
            115                 120                 125
Thr Met Ala Ala Leu Val Ile Tyr Leu Arg Phe His Asn Leu Tyr Thr
    130                 135                 140
Glu Asn Lys Arg Phe Pro Leu Val Asp Phe Cys Val Thr Val Ser Phe
145                 150                 155                 160
Thr Phe Phe Trp Leu Val Ala Ala Ala Trp Gly Lys Gly Leu Thr
                165                 170                 175
Asp Val Lys Gly Ala Thr Arg Pro Ser Ser Leu Thr Ala Ala Met Ser
            180                 185                 190
Val Cys His Gly Glu Glu Ala Val Cys Ser Ala Gly Ala Thr Pro Ser
            195                 200                 205
Met Gly Leu Ala Asn Ile Ser Val Val Arg Pro Val Thr Ala Gly
    210                 215                 220
Ser Ser Thr Ser Pro Ala Ala Gln Ala Cys Pro Ser
225                 230                 235

<210> SEQ ID NO 5
<211> LENGTH: 264
<212> TYPE: PRT
<213> ORGANISM: Bos taurus
<220> FEATURE:
<221> NAME/KEY: MISC_FEATURE
<222> LOCATION: (1)..(264)

<400> SEQUENCE: 5

Met Ser Ser Thr Glu Ser Ser Arg Thr Ala Asp Lys Ser Pro Arg
 1               5                  10                  15
Gln Gln Val Asp Arg Leu Leu Val Gly Leu Arg Trp Arg Arg Leu Glu
                 20                  25                  30
Glu Pro Leu Gly Phe Ile Lys Val Leu Gln Trp Leu Phe Ala Ile Phe
             35                  40                  45
Ala Phe Gly Ser Cys Gly Ser Tyr Ser Gly Glu Thr Gly Ala Thr Val
 50                  55                  60
Arg Cys Asn Asn Glu Ala Lys Asp Val Ser Ala Ile Ile Val Ser Phe
65                  70                  75                  80
Gly Tyr Pro Phe Arg Leu Asn Arg Val Gln Tyr Glu Met Pro Leu Cys
                 85                  90                  95
Asp Asp Glu Ser Thr Ser Lys Thr Met His Leu Met Gly Asp Phe Ser
            100                 105                 110
Ala Pro Ala Glu Phe Phe Val Thr Leu Gly Ile Phe Ser Phe Phe Tyr
            115                 120                 125
Thr Ile Ala Ala Leu Val Ile Tyr Leu Arg Phe His Lys Leu Tyr Thr
    130                 135                 140
Glu Asn Arg Arg Phe Pro Leu Val Asp Phe Cys Val Thr Val Ser Phe
145                 150                 155                 160
Thr Phe Phe Trp Leu Val Ala Ala Ala Ala Trp Gly Lys Gly Leu Thr
```

-continued

```
                  165                 170                 175
Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
        195                 200                 205

Met Gly Leu Ala Asn Ile Ser Val Leu Phe Gly Phe Ile Asn Phe Phe
    210                 215                 220

Leu Trp Ala Gly Asn Cys Trp Phe Val Phe Lys Glu Thr Pro Trp His
225                 230                 235                 240

Gly Gln Gly Gln Asp Gln Gly Gln Thr Ser Pro Glu Ser Ala Ala
                245                 250                 255

Glu Gln Gly Ala Val Glu Lys Gln
            260

<210> SEQ ID NO 6
<211> LENGTH: 251
<212> TYPE: PRT
<213> ORGANISM: Xenopus laevis
<220> FEATURE:
<221> NAME/KEY: MISC_FEATURE
<222> LOCATION: (1)..(251)

<400> SEQUENCE: 6

Met Asp Arg Leu Gly Gly Leu Ala Gly Leu Lys Lys Asn Pro Phe
1               5                   10                  15

Ala Gly Leu Arg Trp Arg Arg Leu Glu Glu Pro Leu Gly Phe Ile Lys
            20                  25                  30

Leu Leu Glu Trp Leu Phe Ala Ile Phe Ala Phe Gly Ser Cys Gly Ser
        35                  40                  45

Tyr Ser Gly Glu Thr Ala Ala Thr Val Met Cys Lys Ser Glu Ala Asp
50                  55                  60

Thr Glu Ile Lys Leu Ile Ser Val Pro Phe Gly Tyr Pro Phe Arg Leu
65                  70                  75                  80

Tyr Arg Gln Arg Tyr Glu Met Pro Ala Cys Asp Asp Met Gly Arg Arg
                85                  90                  95

Ile Leu His Leu Thr Gly Asp Phe Ser Ala Pro Ala Glu Phe Phe Val
            100                 105                 110

Thr Met Gly Val Phe Ala Phe Leu Tyr Ala Met Phe Ala Leu Val Ile
        115                 120                 125

Tyr Leu Arg Phe His Glu Glu Tyr Thr Lys Ile Arg Arg Leu Pro Ile
    130                 135                 140

Val Asp Leu Cys Val Thr Gly Ala Phe Thr Phe Leu Trp Leu Val Ala
145                 150                 155                 160

Ala Ser Ala Trp Gly Lys Gly Leu Met Asp Val Lys Val Ala Thr Gln
                165                 170                 175

Pro Ser Ser Leu Val Ser Ser Met Pro Leu Cys Gln Met Glu Lys Ala
            180                 185                 190

Thr Cys Asn Ala Gly Ser Ser Pro Tyr Phe Ala Leu Ala Asn Ile Ser
        195                 200                 205

Val Leu Phe Gly Phe Leu Asn Phe Ile Ile Trp Ala Ala Asn Ile Trp
    210                 215                 220

Phe Val Phe Lys Glu Thr Thr Trp Ser Lys Lys Pro Ala Ser Lys Glu
225                 230                 235                 240

Glu Ser Ala Glu Arg Gly Glu Val Glu Asp His
                245                 250
```

```
<210> SEQ ID NO 7
<211> LENGTH: 254
<212> TYPE: PRT
<213> ORGANISM: Xenopus tropicalis
<220> FEATURE:
<221> NAME/KEY: MISC_FEATURE
<222> LOCATION: (1)..(254)

<400> SEQUENCE: 7
```

| Met | Asp | Arg | Glu | Gly | Gly | Leu | Ala | Gly | Leu | Gly | Lys | Lys | Asn | Pro | Leu |
|---|---|---|---|---|---|---|---|---|---|---|---|---|---|---|---|
| 1 | | | | 5 | | | | | 10 | | | | | 15 | |

| Ala | Gly | Leu | Arg | Trp | Arg | Arg | Leu | Glu | Glu | Pro | Leu | Gly | Phe | Ile | Lys |
|---|---|---|---|---|---|---|---|---|---|---|---|---|---|---|---|
| | | | 20 | | | | | 25 | | | | | 30 | | |

| Leu | Leu | Glu | Trp | Leu | Phe | Ala | Ile | Phe | Ala | Phe | Gly | Cys | Cys | Gly | Ser |
|---|---|---|---|---|---|---|---|---|---|---|---|---|---|---|---|
| | | 35 | | | | | 40 | | | | | 45 | | | |

| Tyr | Ser | Gly | Glu | Thr | Ala | Ala | Thr | Val | Met | Cys | Lys | Thr | Glu | Thr | Asp |
|---|---|---|---|---|---|---|---|---|---|---|---|---|---|---|---|
| | 50 | | | | | 55 | | | | | 60 | | | | |

| Ser | Asp | Thr | Glu | Ile | Lys | Leu | Ile | Ser | Val | Pro | Phe | Ala | Tyr | Pro | Phe |
|---|---|---|---|---|---|---|---|---|---|---|---|---|---|---|---|
| 65 | | | | | 70 | | | | | 75 | | | | | 80 |

| Arg | Leu | Tyr | Arg | Gln | Arg | Tyr | Glu | Met | Pro | Ala | Cys | Glu | Asp | Ile | Glu |
|---|---|---|---|---|---|---|---|---|---|---|---|---|---|---|---|
| | | | | 85 | | | | | 90 | | | | | 95 | |

| Arg | Arg | Ile | Leu | His | Leu | Thr | Gly | Asp | Phe | Ser | Ala | Pro | Ala | Glu | Phe |
|---|---|---|---|---|---|---|---|---|---|---|---|---|---|---|---|
| | | | 100 | | | | | 105 | | | | | 110 | | |

| Phe | Val | Thr | Met | Gly | Val | Phe | Ala | Phe | Leu | Tyr | Ser | Met | Phe | Ala | Leu |
|---|---|---|---|---|---|---|---|---|---|---|---|---|---|---|---|
| | | 115 | | | | | 120 | | | | | 125 | | | |

| Val | Val | Tyr | Leu | Arg | Phe | His | Glu | Glu | Tyr | Thr | Lys | Ile | Arg | Arg | Val |
|---|---|---|---|---|---|---|---|---|---|---|---|---|---|---|---|
| | 130 | | | | | 135 | | | | | 140 | | | | |

| Pro | Ile | Val | Asp | Leu | Cys | Val | Thr | Gly | Ala | Phe | Ala | Phe | Leu | Trp | Leu |
|---|---|---|---|---|---|---|---|---|---|---|---|---|---|---|---|
| 145 | | | | | 150 | | | | | 155 | | | | | 160 |

| Val | Ala | Ala | Ser | Ala | Trp | Gly | Lys | Gly | Leu | Met | Asp | Val | Lys | Val | Ala |
|---|---|---|---|---|---|---|---|---|---|---|---|---|---|---|---|
| | | | | 165 | | | | | 170 | | | | | 175 | |

| Thr | Gln | Pro | Ser | Asn | Leu | Val | Ser | Ser | Met | Pro | Leu | Cys | Gln | Met | Glu |
|---|---|---|---|---|---|---|---|---|---|---|---|---|---|---|---|
| | | | 180 | | | | | 185 | | | | | 190 | | |

| Lys | Ala | Thr | Cys | Asn | Ala | Gly | Ser | Gln | Pro | Tyr | Phe | Ala | Leu | Ala | Asn |
|---|---|---|---|---|---|---|---|---|---|---|---|---|---|---|---|
| | | 195 | | | | | 200 | | | | | 205 | | | |

| Ile | Ser | Val | Leu | Phe | Gly | Phe | Leu | Asn | Phe | Leu | Ile | Trp | Ala | Ala | Asn |
|---|---|---|---|---|---|---|---|---|---|---|---|---|---|---|---|
| | 210 | | | | | 215 | | | | | 220 | | | | |

| Val | Trp | Phe | Val | Phe | Lys | Glu | Thr | Thr | Leu | Ser | Asn | Lys | Pro | Ala | Ser |
|---|---|---|---|---|---|---|---|---|---|---|---|---|---|---|---|
| 225 | | | | | 230 | | | | | 235 | | | | | 240 |

| Lys | Glu | Glu | Ser | Ala | Glu | Arg | Gly | Glu | Val | Glu | Asp | His | Gln |
|---|---|---|---|---|---|---|---|---|---|---|---|---|---|
| | | | | 245 | | | | | 250 | | | | |

```
<210> SEQ ID NO 8
<211> LENGTH: 268
<212> TYPE: PRT
<213> ORGANISM: Gallus gallus
<220> FEATURE:
<221> NAME/KEY: MISC_FEATURE
<222> LOCATION: (1)..(268)

<400> SEQUENCE: 8
```

| Met | Cys | Met | Val | Ile | Phe | Ala | Pro | Leu | Phe | Ala | Ile | Phe | Ala | Phe | Ala |
|---|---|---|---|---|---|---|---|---|---|---|---|---|---|---|---|
| 1 | | | | 5 | | | | | 10 | | | | | 15 | |

| Thr | Cys | Gly | Gly | Tyr | Ser | Gly | Gly | Leu | Arg | Leu | Ser | Val | Asp | Cys | Ala |
|---|---|---|---|---|---|---|---|---|---|---|---|---|---|---|---|
| | | | 20 | | | | | 25 | | | | | 30 | | |

| Asn | Lys | Ser | Glu | Ser | Asp | Leu | Asn | Ile | Asp | Ile | Ala | Phe | Ala | Tyr | Pro |
|---|---|---|---|---|---|---|---|---|---|---|---|---|---|---|---|
| | | 35 | | | | | 40 | | | | | 45 | | | |

| Phe | Arg | Leu | His | Gln | Val | Asn | Phe | Asp | Ala | Pro | Thr | Cys | Glu | Gly | Lys |
|---|---|---|---|---|---|---|---|---|---|---|---|---|---|---|---|
| | 50 | | | | | 55 | | | | | 60 | | | | |

Arg Arg Glu Thr Leu Ser Leu Ile Gly Asp Phe Ser Ser Ser Ala Glu
 65                  70                  75                  80

Phe Phe Val Thr Ile Ala Val Phe Ala Phe Leu Tyr Ser Leu Ala Ala
                     85                  90                  95

Thr Val Val Tyr Ile Phe Phe Gln Asn Lys Tyr Arg Glu Asn Asn Arg
                100                 105                 110

Gly Pro Leu Ile Asp Phe Ile Val Thr Val Val Phe Ser Phe Leu Trp
            115                 120                 125

Leu Val Gly Ser Ser Ala Trp Ala Lys Gly Leu Ser Asp Val Lys Ile
        130                 135                 140

Ala Thr Asp Pro Asp Glu Val Leu Leu Leu Met Ser Ala Cys Lys Gln
145                 150                 155                 160

Gln Ser Asn Lys Cys Leu Pro Val Arg Ser Pro Val Met Ser Ser Leu
                165                 170                 175

Asn Thr Ser Val Val Phe Gly Phe Leu Asn Phe Ile Leu Trp Ala Gly
            180                 185                 190

Asn Ile Trp Phe Val Phe Lys Glu Thr Gly Trp His Ser Ser Gly Gln
        195                 200                 205

Arg His Ala Ala Asp Thr Met Glu Lys Gln Ser Ser Gly Tyr Asn Gln
210                 215                 220

Gly Gly Tyr Asn Gln Asp Ser Tyr Gly Pro Ala Gly Gly Tyr Asn Gln
225                 230                 235                 240

Pro Gly Ser Tyr Gly Gln Val Gly Asp Tyr Gly Gln Pro Gln Ser Tyr
                245                 250                 255

Gly Gln Ser Gly Pro Thr Ser Phe Ala Asn Gln Ile
                260                 265

<210> SEQ ID NO 9
<211> LENGTH: 265
<212> TYPE: PRT
<213> ORGANISM: Homo sapiens
<220> FEATURE:
<221> NAME/KEY: MISC_FEATURE
<222> LOCATION: (1)..(265)

<400> SEQUENCE: 9

Met Cys Met Val Ile Phe Ala Pro Leu Phe Ala Ile Phe Ala Phe Ala
1                   5                   10                  15

Thr Cys Gly Gly Tyr Ser Gly Gly Leu Arg Leu Ser Val Asp Cys Val
                20                  25                  30

Asn Lys Thr Glu Ser Asn Leu Ser Ile Asp Ile Ala Phe Ala Tyr Pro
            35                  40                  45

Phe Arg Leu His Gln Val Thr Phe Glu Val Pro Thr Cys Glu Gly Lys
        50                  55                  60

Glu Arg Gln Lys Leu Ala Leu Ile Gly Asp Ser Ser Ser Ser Ala Glu
 65                 70                  75                  80

Phe Phe Val Thr Val Ala Val Phe Ala Phe Leu Tyr Ser Leu Ala Ala
                     85                  90                  95

Thr Val Val Tyr Ile Phe Phe Gln Asn Lys Tyr Arg Glu Asn Asn Arg
                100                 105                 110

Gly Pro Leu Ile Asp Phe Ile Val Thr Val Val Phe Ser Phe Leu Trp
            115                 120                 125

Leu Val Gly Ser Ser Ala Trp Ala Lys Gly Leu Ser Asp Val Lys Val
        130                 135                 140

Ala Thr Asp Pro Lys Glu Val Leu Leu Leu Met Ser Ala Cys Lys Gln
145                 150                 155                 160

```
Pro Ser Asn Lys Cys Met Ala Ile His Ser Pro Val Met Ser Ser Leu
                165                 170                 175

Asn Thr Ser Val Val Phe Gly Phe Leu Asn Phe Ile Leu Trp Ala Gly
            180                 185                 190

Asn Ile Trp Phe Val Phe Lys Glu Thr Gly Trp His Ser Ser Gly Gln
        195                 200                 205

Arg Tyr Leu Ser Asp Pro Met Glu Lys His Ser Ser Ser Tyr Asn Gln
    210                 215                 220

Gly Gly Tyr Asn Gln Asp Ser Tyr Gly Ser Ser Ser Gly Tyr Ser Gln
225                 230                 235                 240

Gln Ala Ser Leu Gly Pro Thr Ser Asp Glu Phe Gly Gln Gln Pro Thr
                245                 250                 255

Gly Pro Thr Ser Phe Thr Asn Gln Ile
                260                 265

<210> SEQ ID NO 10
<211> LENGTH: 276
<212> TYPE: PRT
<213> ORGANISM: Homo sapiens
<220> FEATURE:
<221> NAME/KEY: MISC_FEATURE
<222> LOCATION: (1)..(276)

<400> SEQUENCE: 10

Met Cys Met Val Ile Phe Ala Pro His Asn Glu Glu Cys Lys Ser His
1               5                   10                  15

Phe His Leu Leu Phe Ala Ile Phe Ala Phe Ala Thr Cys Gly Gly Tyr
            20                  25                  30

Ser Gly Gly Leu Arg Leu Ser Val Asp Cys Val Asn Lys Thr Glu Ser
        35                  40                  45

Asn Leu Ser Ile Asp Ile Ala Phe Ala Tyr Pro Phe Arg Leu His Gln
    50                  55                  60

Val Thr Phe Glu Val Pro Thr Cys Glu Gly Lys Glu Arg Gln Lys Leu
65                  70                  75                  80

Ala Leu Ile Gly Asp Ser Ser Ser Ala Glu Phe Phe Val Thr Val
                85                  90                  95

Ala Val Phe Ala Phe Leu Tyr Ser Leu Ala Ala Thr Val Val Tyr Ile
            100                 105                 110

Phe Phe Gln Asn Lys Tyr Arg Glu Asn Asn Arg Gly Pro Leu Ile Asp
        115                 120                 125

Phe Ile Val Thr Val Val Phe Ser Phe Leu Trp Leu Val Gly Ser Ser
    130                 135                 140

Ala Trp Ala Lys Gly Leu Ser Asp Val Lys Val Ala Thr Asp Pro Lys
145                 150                 155                 160

Glu Val Leu Leu Leu Met Ser Ala Cys Lys Gln Pro Ser Asn Lys Cys
                165                 170                 175

Met Ala Ile His Ser Pro Val Met Ser Ser Leu Asn Thr Ser Val Val
            180                 185                 190

Phe Gly Phe Leu Asn Phe Ile Leu Trp Ala Gly Asn Ile Trp Phe Val
        195                 200                 205

Phe Lys Glu Thr Gly Trp His Ser Ser Gly Gln Arg Tyr Leu Ser Asp
    210                 215                 220

Pro Met Glu Lys His Ser Ser Ser Tyr Asn Gln Gly Gly Tyr Asn Gln
225                 230                 235                 240

Asp Ser Tyr Gly Ser Ser Ser Gly Tyr Ser Gln Gln Ala Ser Leu Gly
                245                 250                 255
```

```
Pro Thr Ser Asp Glu Phe Gly Gln Gln Pro Thr Gly Pro Thr Ser Phe
            260                 265                 270

Thr Asn Gln Ile
        275

<210> SEQ ID NO 11
<211> LENGTH: 265
<212> TYPE: PRT
<213> ORGANISM: Homo sapiens
<220> FEATURE:
<221> NAME/KEY: MISC_FEATURE
<222> LOCATION: (1)..(265)

<400> SEQUENCE: 11

Met Cys Met Val Ile Phe Ala Pro Leu Phe Ala Ile Phe Ala Phe Ala
1               5                   10                  15

Thr Cys Gly Gly Tyr Ser Gly Gly Leu Arg Leu Ser Val Asp Cys Val
            20                  25                  30

Asn Lys Thr Glu Ser Asn Leu Ser Ile Asp Ile Ala Phe Ala Tyr Pro
        35                  40                  45

Phe Arg Leu His Gln Val Thr Phe Glu Val Pro Thr Cys Glu Gly Lys
50                  55                  60

Glu Arg Gln Lys Leu Ala Leu Ile Gly Asp Ser Ser Ser Ala Glu
65                  70                  75                  80

Phe Phe Val Thr Val Ala Val Phe Ala Phe Leu Tyr Ser Leu Ala Ala
                85                  90                  95

Thr Val Val Tyr Ile Phe Phe Gln Asn Lys Tyr Arg Glu Asn Asn Arg
            100                 105                 110

Gly Pro Leu Ile Asp Phe Ile Val Thr Val Val Phe Ser Phe Leu Trp
        115                 120                 125

Leu Val Gly Ser Ser Ala Trp Ala Lys Gly Leu Ser Asp Val Lys Val
130                 135                 140

Ala Thr Asp Pro Lys Glu Val Leu Leu Leu Met Ser Ala Cys Lys Gln
145                 150                 155                 160

Pro Ser Asn Lys Cys Met Ala Ile His Ser Pro Val Met Ser Ser Leu
                165                 170                 175

Asn Thr Ser Val Val Phe Gly Phe Leu Asn Phe Ile Leu Trp Ala Gly
            180                 185                 190

Asn Ile Trp Phe Val Phe Lys Glu Thr Gly Trp His Ser Ser Gly Gln
        195                 200                 205

Arg Tyr Leu Ser Asp Pro Met Glu Lys His Ser Ser Tyr Asn Gln
210                 215                 220

Gly Gly Tyr Asn Gln Asp Ser Tyr Gly Ser Ser Gly Tyr Ser Gln
225                 230                 235                 240

Gln Ala Ser Leu Gly Pro Thr Ser Asp Glu Phe Gly Gln Gln Pro Thr
                245                 250                 255

Gly Pro Thr Ser Phe Thr Asn Gln Ile
            260                 265

<210> SEQ ID NO 12
<211> LENGTH: 265
<212> TYPE: PRT
<213> ORGANISM: Mus musculus
<220> FEATURE:
<221> NAME/KEY: MISC_FEATURE
<222> LOCATION: (1)..(265)

<400> SEQUENCE: 12
```

Met Cys Met Val Ile Phe Ala Pro Leu Phe Ala Met Phe Ala
1               5                   10                  15

Thr Cys Gly Gly Tyr Ser Gly Gly Leu Arg Leu Ser Val Asp Cys Val
            20                  25                  30

Asn Lys Thr Glu Ser Asn Leu Ser Ile Asp Ile Ala Phe Ala Tyr Pro
        35                  40                  45

Phe Arg Leu Gln Gln Val Thr Phe Glu Val Pro Thr Cys Glu Gly Lys
    50                  55                  60

Glu Gln Gln Lys Leu Ala Leu Val Gly Asp Ser Ser Ser Ala Glu
65                  70                  75                  80

Phe Phe Val Thr Val Ala Val Phe Ala Phe Leu Tyr Ser Leu Ala Ala
                85                  90                  95

Thr Val Val Tyr Ile Phe Phe Gln Asn Lys Tyr Arg Glu Asn Asn Arg
            100                 105                 110

Gly Pro Leu Ile Asp Phe Ile Val Thr Val Val Phe Ser Phe Leu Trp
            115                 120                 125

Leu Val Gly Ser Ser Ala Trp Ala Lys Gly Leu Ser Asp Val Lys Val
130                 135                 140

Ala Thr Asp Pro Lys Glu Val Leu Leu Leu Met Ser Ala Cys Lys Gln
145                 150                 155                 160

Pro Ser Asn Lys Cys Met Ala Val His Ser Pro Val Met Ser Ser Leu
                165                 170                 175

Asn Thr Ser Val Val Phe Gly Phe Leu Asn Phe Ile Leu Trp Ala Gly
            180                 185                 190

Asn Ile Trp Phe Val Phe Lys Glu Thr Gly Trp His Ser Ser Gly Gln
        195                 200                 205

Arg Tyr Leu Ser Asp Pro Met Glu Lys His Ser Ser Ser Tyr Asn Gln
210                 215                 220

Gly Arg Tyr Asn Gln Glu Ser Tyr Gly Ser Ser Gly Gly Tyr Ser Gln
225                 230                 235                 240

Gln Ala Asn Leu Gly Pro Thr Ser Asp Glu Phe Gly Gln Gln Pro Ser
                245                 250                 255

Gly Pro Thr Ser Phe Asn Asn Gln Ile
            260                 265

<210> SEQ ID NO 13
<211> LENGTH: 255
<212> TYPE: PRT
<213> ORGANISM: Mus musculus
<220> FEATURE:
<221> NAME/KEY: MISC_FEATURE
<222> LOCATION: (1)..(255)

<400> SEQUENCE: 13

Phe Asp Arg Ser Leu Asn Arg Thr Arg Gly Phe Ser Ala Ala Gly Gly
1               5                   10                  15

Ala Ala Arg Arg Thr Glu Pro Pro Arg Ala Arg Ala Ala Pro Pro
            20                  25                  30

Arg Pro Ser Pro Pro Ala Trp Ser Pro Ala Cys Pro Arg Pro Arg Ala
            35                  40                  45

Arg Arg Pro Gln Arg Pro Arg Ala Pro Arg Ser Leu Pro Ala Arg Glu
    50                  55                  60

Ser Asn Pro Cys Thr Ala Pro Arg Arg Ala Ser Met Ser Ser Thr Glu
65                  70                  75                  80

Ser Pro Gly Arg Thr Ser Asp Lys Ser Pro Arg Gln Gln Val Asp Arg
                85                  90                  95

```
Leu Leu Leu Gly Leu Arg Trp Gln Arg Leu Glu Glu Pro Leu Gly Phe
            100                 105                 110

Ile Lys Val Leu Gln Trp Leu Phe Ala Ile Phe Ala Phe Gly Ser Cys
            115                 120                 125

Gly Ser Tyr Ser Gly Glu Thr Gly Ala Leu Val Leu Cys Asn Asn Glu
            130                 135                 140

Ala Lys Asp Val Ser Ser Ile Ile Val Leu Phe Gly Tyr Pro Phe Arg
145                 150                 155                 160

Leu Tyr Gln Val Gln Tyr Glu Met Pro Leu Cys Asp Gln Asp Ser Thr
                165                 170                 175

Ser Lys Thr Met Asn Leu Met Gly Asp Phe Ser Ala Pro Ala Glu Phe
            180                 185                 190

Phe Val Thr Leu Gly Ile Phe Ser Phe Phe Tyr Thr Met Ala Ala Leu
            195                 200                 205

Val Ile Tyr Leu Arg Phe His Lys Leu Tyr Thr Glu Asn Lys Arg Phe
            210                 215                 220

Pro Leu Val Val Ser Glu Pro Trp Pro Arg Gly Ile Gly Pro Ile Asn
225                 230                 235                 240

Val Arg Asp Gly Gly Ala Ile Lys Ser Asn Ser Phe Pro Glu Ser
                245                 250                 255

<210> SEQ ID NO 14
<211> LENGTH: 285
<212> TYPE: PRT
<213> ORGANISM: Mus musculus
<220> FEATURE:
<221> NAME/KEY: MISC_FEATURE
<222> LOCATION: (1)..(285)

<400> SEQUENCE: 14

Met Asp Pro Val Ser Gln Val Ala Ser Ala Gly Thr Phe Arg Ala Leu
1               5                   10                  15

Lys Glu Pro Leu Ala Phe Leu Arg Ala Leu Glu Leu Leu Phe Ala Met
            20                  25                  30

Phe Ala Phe Ala Thr Cys Gly Gly Tyr Ser Gly Gly Leu Arg Leu Ser
            35                  40                  45

Val Asp Cys Val Asn Lys Thr Glu Ser Asn Leu Ser Ile Asp Ile Ala
50                  55                  60

Phe Ala Tyr Pro Phe Arg Leu Gln Gln Val Thr Phe Glu Val Pro Thr
65                  70                  75                  80

Cys Glu Gly Lys Glu Gln Gln Lys Leu Ala Leu Val Gly Asp Ser Ser
                85                  90                  95

Ser Ser Ala Glu Phe Phe Val Thr Val Ala Val Phe Ala Phe Leu Tyr
            100                 105                 110

Ser Leu Ala Ala Thr Val Val Tyr Ile Phe Phe Gln Asn Lys Tyr Arg
            115                 120                 125

Glu Asn Asn Arg Gly Pro Leu Ile Asp Phe Ile Val Thr Val Val Phe
            130                 135                 140

Ser Phe Leu Trp Leu Val Gly Ser Ser Ala Trp Ala Lys Gly Leu Ser
145                 150                 155                 160

Asp Val Lys Val Ala Thr Asp Pro Lys Glu Val Leu Leu Leu Met Ser
                165                 170                 175

Ala Cys Lys Gln Pro Ser Asn Lys Cys Met Ala Val His Ser Pro Val
            180                 185                 190

Met Ser Ser Leu Asn Thr Ser Val Val Phe Gly Phe Leu Asn Phe Ile
            195                 200                 205
```

```
Leu Trp Ala Gly Asn Ile Trp Phe Val Phe Lys Glu Thr Gly Trp His
            210                 215                 220

Ser Ser Gly Gln Arg Tyr Leu Ser Asp Pro Met Glu Lys His Ser Ser
225                 230                 235                 240

Ser Tyr Asn Gln Gly Arg Tyr Asn Gln Glu Ser Tyr Gly Ser Ser Gly
            245                 250                 255

Gly Tyr Ser Gln Gln Ala Asn Leu Gly Pro Thr Ser Asp Glu Phe Gly
            260                 265                 270

Gln Gln Pro Ser Gly Pro Thr Ser Phe Asn Asn Gln Ile
            275                 280                 285

<210> SEQ ID NO 15
<211> LENGTH: 390
<212> TYPE: PRT
<213> ORGANISM: Mus musculus
<220> FEATURE:
<221> NAME/KEY: MISC_FEATURE
<222> LOCATION: (1)..(390)

<400> SEQUENCE: 15

Met Ser Ser Thr Glu Ser Pro Gly Arg Thr Ser Asp Lys Ser Pro Arg
1               5                   10                  15

Gln Gln Val Asp Arg Leu Leu Gly Leu Arg Trp Gln Arg Leu Glu
            20                  25                  30

Glu Pro Leu Gly Phe Ile Lys Val Leu Gln Trp Leu Phe Ala Ile Phe
            35                  40                  45

Ala Phe Gly Ser Cys Gly Ser Tyr Ser Gly Thr Gly Ala Leu Val
        50                  55                  60

Leu Cys Asn Asn Glu Ala Lys Asp Val Ser Ser Ile Ile Val Leu Phe
65                  70                  75                  80

Gly Tyr Pro Phe Arg Leu Tyr Gln Val Gln Tyr Glu Met Pro Leu Cys
                85                  90                  95

Asp Gln Asp Ser Thr Ser Lys Thr Met Asn Leu Met Gly Asp Phe Ser
            100                 105                 110

Ala Pro Ala Glu Phe Phe Val Thr Leu Gly Ile Phe Ser Phe Phe Tyr
            115                 120                 125

Thr Met Ala Ala Leu Val Ile Tyr Leu Arg Phe His Lys Leu Tyr Thr
        130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175

Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
        195                 200                 205

Met Gly Leu Ala Asn Leu Ser Val Leu Phe Gly Phe Ile Asn Phe Phe
    210                 215                 220

Leu Trp Ala Gly Asn Cys Trp Phe Val Phe Lys Glu Thr Pro Trp His
225                 230                 235                 240

Gly Gln Gly Gln Asp Gln Gly Gln Gly Pro Ser Gln Glu Ser Ala Ala
            245                 250                 255

Glu Gln Gly Ala Val Glu Lys Gln Leu Ser Ser Leu His Leu Pro Thr
        260                 265                 270

Pro Gln Leu Asp Gly Thr Leu Ser Ala Pro Ala Ser Thr Gly Pro
            275                 280                 285
```

-continued

```
Pro Pro Leu Pro Leu Pro Pro Ala Pro Pro Leu Pro Pro Pro Thr
        290                 295                 300

Pro Arg Pro Pro Ser Phe Trp Thr Leu Arg Phe Glu Arg Met Asp Gly
305                 310                 315                 320

Trp Ala Ser Ala Val Gly Asn Leu Gly Arg Pro Pro Leu Ala Ser Tyr
                325                 330                 335

Pro Ser Ser Cys Trp Gly Ser Lys Arg Gln Asp Leu Ser Ala Ser Cys
            340                 345                 350

Leu Leu Pro Gly Ala Glu Ala Ser Tyr Leu Gly Lys Leu Thr Gly Asn
        355                 360                 365

Leu Ala Ala Glu Phe Cys Val Glu Gly Pro Val Ile Leu Trp His
    370                 375                 380

Pro Ser Ile Thr Gly Ile
385                 390

<210> SEQ ID NO 16
<211> LENGTH: 341
<212> TYPE: PRT
<213> ORGANISM: Mus musculus
<220> FEATURE:
<221> NAME/KEY: MISC_FEATURE
<222> LOCATION: (1)..(341)

<400> SEQUENCE: 16

Arg Leu Phe Asp Arg Ser Leu Asn Arg Thr Arg Gly Phe Ser Ala Ala
1               5                   10                  15

Gly Gly Ala Ala Arg Arg Thr Glu Pro Pro Arg Ala Arg Ala Ala Ala
            20                  25                  30

Pro Pro Arg Pro Ser Pro Pro Ala Trp Ser Pro Ala Cys Pro Arg Pro
        35                  40                  45

Arg Ala Arg Arg Pro Gln Arg Pro Arg Ala Pro Arg Ser Leu Pro Ala
    50                  55                  60

Arg Glu Ser Asn Pro Cys Thr Ala Pro Arg Ala Ser Met Ser Ser
65                  70                  75                  80

Thr Glu Ser Pro Gly Arg Thr Ser Asp Lys Ser Pro Arg Gln Gln Val
                85                  90                  95

Asp Arg Leu Leu Leu Gly Leu Arg Trp Gln Arg Leu Glu Glu Pro Leu
            100                 105                 110

Gly Phe Ile Lys Val Leu Gln Trp Leu Phe Ala Ile Phe Ala Phe Gly
        115                 120                 125

Ser Cys Gly Ser Tyr Ser Gly Glu Thr Gly Ala Leu Val Leu Cys Asn
    130                 135                 140

Asn Glu Ala Lys Asp Val Ser Ser Ile Ile Val Leu Phe Gly Tyr Pro
145                 150                 155                 160

Phe Arg Leu Tyr Gln Val Gln Tyr Glu Met Pro Leu Cys Asp Gln Asp
                165                 170                 175

Ser Thr Ser Lys Thr Met Asn Leu Met Gly Asp Phe Ser Ala Pro Ala
            180                 185                 190

Glu Phe Phe Val Thr Leu Gly Ile Phe Ser Phe Phe Tyr Thr Met Ala
        195                 200                 205

Ala Leu Val Ile Tyr Leu Arg Phe His Lys Leu Tyr Thr Glu Asn Lys
    210                 215                 220

Arg Phe Pro Leu Val Asp Phe Cys Val Thr Val Ser Phe Thr Phe Phe
225                 230                 235                 240

Trp Leu Val Ala Ala Ala Trp Gly Lys Gly Leu Thr Asp Val Lys
                245                 250                 255
```

```
Gly Ala Thr Arg Pro Ser Ser Leu Thr Ala Ala Met Ser Val Cys His
            260                 265                 270

Gly Glu Glu Ala Val Cys Ser Ala Gly Ala Thr Pro Ser Met Gly Leu
            275                 280                 285

Ala Asn Leu Ser Val Leu Phe Gly Phe Ile Asn Phe Leu Trp Ala
            290                 295                 300

Gly Asn Cys Trp Phe Val Phe Lys Glu Thr Pro Trp His Gly Gln Gly
305                 310                 315                 320

Gln Asp Gln Gly Gln Gly Pro Ser Gln Glu Ser Ala Ala Glu Gln Gly
            325                 330                 335

Ala Val Glu Lys Gln
            340

<210> SEQ ID NO 17
<211> LENGTH: 272
<212> TYPE: PRT
<213> ORGANISM: Homo sapiens
<220> FEATURE:
<221> NAME/KEY: MISC_FEATURE
<222> LOCATION: (1)..(272)

<400> SEQUENCE: 17

Met Ser Ser Thr Glu Ser Ala Gly Arg Thr Ala Asp Lys Ser Pro Arg
1               5                   10                  15

Gln Gln Val Asp Arg Leu Leu Val Gly Leu Arg Trp Arg Arg Leu Glu
            20                  25                  30

Glu Pro Leu Gly Phe Ile Lys Val Leu Gln Trp Leu Phe Ala Ile Phe
            35                  40                  45

Ala Phe Gly Ser Cys Gly Ser Tyr Ser Gly Glu Thr Gly Ala Met Val
        50                  55                  60

Arg Cys Asn Asn Glu Ala Lys Asp Val Ser Ser Ile Ile Val Ala Phe
65                  70                  75                  80

Gly Tyr Pro Phe Arg Leu His Arg Ile Gln Tyr Glu Met Pro Leu Cys
                85                  90                  95

Asp Glu Glu Ser Ser Ser Lys Thr Met His Leu Met Gly Asp Phe Ser
            100                 105                 110

Ala Pro Ala Glu Phe Phe Val Thr Leu Gly Ile Phe Ser Phe Phe Tyr
            115                 120                 125

Thr Met Ala Ala Leu Val Ile Tyr Leu Arg Phe His Asn Leu Tyr Thr
130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175

Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
            195                 200                 205

Met Gly Leu Ala Asn Ile Ser Val Leu Phe Gly Phe Ile Asn Phe Phe
        210                 215                 220

Leu Trp Ala Gly Asn Cys Trp Phe Val Phe Lys Glu Thr Pro Trp His
225                 230                 235                 240

Gly Gln Gly Gln Gly Gln Asp Gln Asp Gln Asp Gln Asp Gln Gly Gln
                245                 250                 255

Gly Pro Ser Gln Glu Ser Ala Ala Glu Gln Gly Ala Val Glu Lys Gln
            260                 265                 270
```

<210> SEQ ID NO 18
<211> LENGTH: 143
<212> TYPE: PRT
<213> ORGANISM: Homo sapiens
<220> FEATURE:
<221> NAME/KEY: MISC_FEATURE
<222> LOCATION: (1)..(143)

<400> SEQUENCE: 18

```
Met Ala Ala Leu Val Ile Tyr Leu Arg Phe His Asn Leu Tyr Thr Glu
1               5                   10                  15

Asn Lys Arg Phe Pro Leu Val Asp Phe Cys Val Thr Val Ser Phe Thr
            20                  25                  30

Phe Phe Trp Leu Val Ala Ala Ala Trp Gly Lys Gly Leu Thr Asp
        35                  40                  45

Val Lys Gly Ala Thr Arg Pro Ser Ser Leu Thr Ala Ala Met Ser Val
    50                  55                  60

Cys His Gly Glu Glu Ala Val Cys Ser Ala Gly Ala Thr Pro Ser Met
65                  70                  75                  80

Gly Leu Ala Asn Ile Ser Val Leu Phe Gly Phe Ile Asn Phe Phe Leu
                85                  90                  95

Trp Ala Gly Asn Cys Trp Phe Val Phe Lys Glu Thr Pro Trp His Gly
            100                 105                 110

Gln Gly Gln Gly Gln Asp Gln Asp Gln Asp Gln Asp Gln Gly Gln Gly
        115                 120                 125

Pro Ser Gln Glu Ser Ala Ala Glu Gln Gly Ala Val Glu Lys Gln
    130                 135                 140
```

<210> SEQ ID NO 19
<211> LENGTH: 265
<212> TYPE: PRT
<213> ORGANISM: Bos taurus
<220> FEATURE:
<221> NAME/KEY: MISC_FEATURE
<222> LOCATION: (1)..(265)

<400> SEQUENCE: 19

```
Met Cys Met Val Ile Phe Ala Pro Leu Phe Ala Ile Phe Ala Phe Ala
1               5                   10                  15

Thr Cys Gly Gly Tyr Ser Gly Gly Leu Arg Leu Ser Val Asp Cys Ala
            20                  25                  30

Asn Lys Thr Glu Ser Asp Leu Ser Ile Asp Val Ala Phe Ala Tyr Pro
        35                  40                  45

Phe Arg Leu His Gln Val Thr Phe Glu Val Pro Thr Cys Glu Gly Lys
    50                  55                  60

Glu Arg Gln Lys Val Ser Leu Ile Gly Asp Ser Ser Ser Ser Ala Glu
65                  70                  75                  80

Phe Phe Val Thr Val Ala Val Phe Ala Phe Leu Tyr Ser Leu Ala Ala
                85                  90                  95

Thr Val Val Tyr Ile Phe Phe Gln Asn Lys Tyr Arg Glu Asn Asn Arg
            100                 105                 110

Gly Pro Leu Ile Asp Phe Ile Val Thr Val Phe Ser Phe Leu Trp
        115                 120                 125

Leu Val Gly Ser Ser Ala Trp Ala Lys Gly Leu Ser Asp Val Lys Val
    130                 135                 140

Ala Thr Asp Pro Lys Glu Val Leu Leu Leu Met Ser Ala Cys Lys Gln
145                 150                 155                 160

Pro Ser Asn Lys Cys Thr Ala Val His Ser Pro Val Met Ser Ser Leu
```

```
                    165                 170                 175
Asn Thr Ser Val Val Phe Gly Phe Leu Asn Phe Ile Leu Trp Ala Gly
            180                 185                 190

Asn Ile Trp Phe Val Phe Lys Glu Thr Gly Trp His Ser Ser Ser Gln
        195                 200                 205

Arg Tyr Leu Ser Asp Pro Met Glu Lys His Ser Ser Ser Tyr Asn Arg
    210                 215                 220

Gly Gly Tyr Asn Gln Asp Ser Tyr Gly Ser Ser Gly Tyr Asn Gln
225                 230                 235                 240

Gln Ala Ser Leu Gly Pro Ser Ser Asp Glu Phe Gly Gln Gln Ser Ala
            245                 250                 255

Ala Pro Ala Ser Phe Thr Asn Gln Met
        260                 265

<210> SEQ ID NO 20
<211> LENGTH: 265
<212> TYPE: PRT
<213> ORGANISM: Rattus norvegicus
<220> FEATURE:
<221> NAME/KEY: MISC_FEATURE
<222> LOCATION: (1)..(265)

<400> SEQUENCE: 20

Met Cys Met Val Ile Phe Ala Pro Leu Phe Ala Ile Phe Ala Phe Ala
1               5                   10                  15

Thr Cys Gly Gly Tyr Ser Gly Gly Leu Arg Leu Ser Val Asp Cys Val
            20                  25                  30

Asn Lys Thr Glu Ser Asn Leu Ser Ile Asp Ile Ala Phe Ala Tyr Pro
        35                  40                  45

Phe Arg Leu His Gln Val Thr Phe Glu Val Pro Thr Cys Glu Gly Lys
    50                  55                  60

Glu Arg Gln Lys Leu Ala Leu Val Gly Asp Ser Ser Ser Ser Ala Glu
65                  70                  75                  80

Phe Phe Val Thr Val Ala Val Phe Ala Phe Leu Tyr Ser Leu Ala Ala
                85                  90                  95

Thr Val Val Tyr Ile Phe Phe Gln Asn Lys Tyr Arg Glu Asn Asn Arg
            100                 105                 110

Gly Pro Leu Ile Asp Phe Ile Val Thr Val Val Phe Ser Phe Leu Trp
        115                 120                 125

Leu Val Gly Ser Ser Ala Trp Ala Lys Gly Leu Ser Asp Val Lys Val
130                 135                 140

Ala Thr Asp Pro Lys Glu Val Leu Leu Leu Met Ser Ala Cys Lys Gln
145                 150                 155                 160

Pro Ser Asn Lys Cys Met Ala Val His Ser Pro Val Met Ser Ser Leu
                165                 170                 175

Asn Thr Ser Val Val Phe Gly Phe Leu Asn Phe Ile Leu Trp Ala Gly
            180                 185                 190

Asn Ile Trp Phe Val Phe Lys Glu Thr Gly Trp His Ser Ser Gly Gln
        195                 200                 205

Arg Tyr Leu Ser Asp Pro Met Glu Lys His Ser Ser Ser Tyr Asn Gln
    210                 215                 220

Gly Gly Tyr Asn Gln Asp Ser Tyr Gly Ser Ser Gly Tyr Ser Gln
225                 230                 235                 240

Gln Ala Ser Leu Gly Pro Thr Ser Asp Glu Phe Gly Gln Gln Pro Ser
            245                 250                 255

Gly Pro Thr Ser Phe Asn Asn Gln Ile
```

<210> SEQ ID NO 21
<211> LENGTH: 1666
<212> TYPE: DNA
<213> ORGANISM: Xenopus tropicalis
<220> FEATURE:
<221> NAME/KEY: misc_feature
<222> LOCATION: (1)..(1666)

<400> SEQUENCE: 21

| | | | | | |
|---|---|---|---|---|---|
| gtaacttaat | taagttgcgg | aaatatcagt | aatcaaactg | atacagattt | ttagtcatat | 60 |
| ttacagaata | tccagaaaca | atattgtgtc | agtggtacaa | atttacagaa | agcctgtctg | 120 |
| cataaaacaa | atactatata | catttaatga | actagattta | tagattgtaa | agctgtaaga | 180 |
| gagaggaaac | ggtaggtaca | gaaaaaaagt | aacaggttta | cagaagctgg | tcatcaggag | 240 |
| gaacagacac | actcccttca | cttggatact | tgagcccttc | tgttcagacg | actgagttcc | 300 |
| agccacttac | ccttggacac | ccttaaataa | ggaccatgtc | aacagcagtt | tcctcctcaa | 360 |
| cgatggacag | agagggggc | cttgcaggac | ttggcaagaa | gaacccactg | gctggtctac | 420 |
| gctggaggag | gttagaggag | ccattgggat | tcattaagtt | actggaatgg | ctgtttgcta | 480 |
| tatttgcctt | tggatgttgt | gggtcataca | gtggagagac | agcagcaact | gtcatgtgca | 540 |
| agacagagac | ggactcagac | acagaaataa | agctcatctc | agttcccttt | gcatacccat | 600 |
| tcaggctgta | tcgccagcgc | tatgagatgc | cagcttgtga | agatatagaa | aggcgtattc | 660 |
| tccacttgac | aggggatttc | tcagcccccg | cagagttctt | tgttaccatg | ggagtctttg | 720 |
| cattcctata | ctctatgttt | gcactggtcg | tctatctgcg | cttccacgaa | gaatacacca | 780 |
| aaatccgccg | agtgccaatt | gtggatttgt | gcgtgactgg | tgcctttgcc | tttttgtggc | 840 |
| ttgtggcagc | ttcagcttgg | gggaaaggac | tgatggatgt | gaaggtggcc | actcaacctt | 900 |
| ccaaccttgt | ctcttcaatg | cctctgtgcc | aaatggaaaa | agcaacatgc | aatgctggct | 960 |
| ctcaaccata | ttttgcactt | gctaacattt | ctgtgctctt | tggctttctg | aatttcctta | 1020 |
| tctgggctgc | caatgtatgg | tttgtgttta | aagagaccac | attgagtaat | aaacctgcct | 1080 |
| ccaaagagga | atctgcagag | cgtggagagg | ttgaagacca | ccagtgatac | ctggcaaaca | 1140 |
| aattcctggg | tttccaacat | caactcttcc | tcctgaaatt | ctagaaatga | gccctctcct | 1200 |
| ttaccaggct | tcaaattatc | attatgatct | tttatttttt | gccctaacac | tgtccactct | 1260 |
| ttcagtgaat | atgagtaata | ttccaaaaac | ataccagtat | acagaggtgc | ttattaaaac | 1320 |
| tgcttaatgt | agggtttatt | tgaatcatat | ttaatacagc | ccagcatata | gcgtatttta | 1380 |
| tgtacgagta | acccaatttg | tacctaacca | tagacacaaa | taaaaaagca | gggttgagct | 1440 |
| ttttataatg | ctgtttataa | cagtatttat | ttttaaatat | gtgccctact | gtataggaca | 1500 |
| gtactgatcc | ataatatcct | ttcttttgga | attgcctcct | gtcctgtaac | cttaataacc | 1560 |
| tttctcacct | gtccacagta | agatgaccca | tctatctcca | gtgtctctgg | tgctatttat | 1620 |
| taaataaaaa | taaatactct | acaaaaaaaa | aaaaaaaaa | aaaaaa | | 1666 |

<210> SEQ ID NO 22
<211> LENGTH: 3779
<212> TYPE: DNA
<213> ORGANISM: Homo sapiens
<220> FEATURE:
<221> NAME/KEY: misc_feature
<222> LOCATION: (1)..(3779)

<400> SEQUENCE: 22

```
aaggtgcccg gcgagcggag aaagggagca gaggggcgg gaggagggtt cgggagcgca    60
cgccacgtga cccggcggcc aagttcgctg cgagtttgac agaagtttga atccgagtcg   120
ggggctttct gctgccggcg gggcaccgcg gcggccgcag cctctgagag cacgaacagc   180 agcgccccg cgtcccagcc agccagccag ccagactgga ctccggccca ccgacggccg    240
ctcgcgctcc ggccccgctc gcctgctctg ccccggacct gcagctcccc gctccccgc    300 cgtgtccgcc gcctcccggc cagagagcca agccaccacg ccgcgcccag cgctcgccgc    360
gccagcatgt cctcgaccga gagcgccggc cgcacggcgg acaagtcgcc gcgccagcag    420 gtggaccgc tactcgtggg gctgcgctgg cggcggctgg aggagccgct gggcttcatc      480
aaagttctcc agtggctctt tgctattttc gccttcgggt cctgtggctc ctacagcggg    540
gagacaggag caatggttcg ctgcaacaac gaagccaagg acgtgagctc catcatcgtt    600
gcatttggct atcccttcag gttgcaccgg atccaatatg agatgcccct ctgcgatgaa   660
gagtccagct ccaagaccat gcacctcatg ggggacttct ctgcacccgc cgagttcttc   720 gtgaccttg gcatcttttc cttcttctat accatggctg ccctagttat ctacctgcgc     780
ttccacaacc tctacacaga gaacaaacgc ttcccgctgg tggacttctg tgtgactgtc    840
tccttcacct tcttctggct ggtagctgca gctgcctggg gcaagggcct gaccgatgtc   900
aagggggcca cacgaccatc cagcttgaca gcagccatgt cagtgtgcca tggagaggaa    960
gcagtgtgca gtgccggggc cacgccctct atgggcctgg ccaacatctc cgtgctcttt   1020
ggctttatca acttcttcct gtgggccggg aactgttggt ttgtgttcaa ggagaccccg   1080
tggcatggac agggccaggg ccaggaccag gaccaggacc aggaccaggg ccaggtccc    1140 agccaggaga gtgcagctga gcagggagca gtggagaagc agtaagcagc cccccacctg   1200
gctattcccg aactggacag cacctcttca accacctccg gcttccagga cctttctctt   1260
cctcctcctc caattcccct cccccatcat tctggtcttt gagctttgag acgatgggca   1320
ggcatcagct gttggaaacc tgggcagccc tctcagtggc ttcctatcct ccttcttgct   1380
ggagccatga atggcaggag ctcagtgctt cttgtgcagt gcctggaccc aggtatctta   1440 cttgggtct tacttgtacc cttacagtct ctgagaacca gcctctgctg caggtgaggg   1500 ttggggcag gaaaccagtg tctgagact ggttcctagc agccaccttt ctgtcaacct   1560
gtccggcttc aacaatatta ggggaaggg aaatcagcta gtagccttcc cctctggtcc   1620
cttgtgtgga ggccccaata gtggtttggc gacccctcct cagtggctgt catctagtcc   1680
ctgcgtctga tctccagtca tcccatgact cagtgtgcct tccactgtct tctctggcct   1740
ctgcctgccc acagaatcca ccatgtgtga accagagagg tccaccagcc tagaaaacag   1800
cccttcagag ggtcctgatg aggccttcct ggactcagct gggagcaaga taaattgcaa   1860
ctgagttgca gcttcaagaa agtaaagcca gtaagcttgc tggcagaatc aatttcttct   1920 atccctcaa tcctcccacc caccaggctg ggcactttc caccaacact ctaaactcta    1980
ctttagaaac gccctatctt cctccctgtc ctccttcttg gtctcacact tgggactcaa   2040
aaatgtggag tcaggacctg cctcctaatc cccttacttc tctgtccatc tcccttcccc   2100
agcatcgtgc atctgaggca tttgagatcc ttttttgaagt ctgtccaggc cttccttta   2160 ttcctgtggg gccagacagg ggcttaggaa gggccaaagg accatcatga ggctaagttg   2220
ccccagagcc ccaggatgga tgggcccatt ttttccttat tccctgctca gttttttccc   2280
ctgctccttc tctagtcctt cttcatatt tctccttctc atcttgaaaa caggatgttc     2340
cctcttccct tgctgtccca tttctcccct gtgtccttat ttctcccagt ctctatcccc   2400
```

| | |
|---|---|
| tctcaagtcc agggcaggcc gatgctattg gtgcttcttc actttgggac ccagttccat | 2460 |
| atttgtcttt agtgtatatc ctcttcctga tacctccttc agtccctctc tgggcccaa | 2520 |
| ggctgagaat cagtgttaac tgggtaagga tcatttgctt cctacccagc tcaatctgcc | 2580 |
| ctggccatag gcttcccag ggaaggaaga agagggaaga atccgaccac tttccaatcc | 2640 |
| agtgccaatt ggcccactaa gcatcctaaa ggtgaatgtg ccctgtgcca atctctcctc | 2700 |
| aggactgagt caaccccctt caacctcctc acctctctaa acaccatcca tagtaacatg | 2760 |
| tgcattactg gggtacctag gagtcaggac ttttgacttc aggccagtca tttcctcccg | 2820 |
| atggggaaag ggtgagattt acatcccaa atgcttgagt ccctcagtga aagaattagt | 2880 |
| ttttgtttgt ttgtttaaga ttttggggaa gagatttgag gaggaaagaa aggagatggg | 2940 |
| gtgagagggt ttttaagtct gaaactctct gtcatgagct gtccccatgg ttactcaagg | 3000 |
| acaagggggg acagttttgc ctacagctcc agagacacag agaacaaagg ggtgaccttc | 3060 |
| attttttcttc aagccggcct ctgtgggggt ctgtgagcag cttctactgg atctttgttt | 3120 |
| ggattctgtg tctgtatta taatttattt gaaatgtgct gggtagtgtt ctcatttggg | 3180 |
| ggctgaagtt agcaactggg ccttcagcta gggaaagcag ttgcgggcag ggggtggggg | 3240 |
| gagattatat tcactcctgc caaggactcc cagcccagga ctctctttag agcaaggaag | 3300 |
| cctcgttctc tttcttctca agaggctctc ttgttctcca tcaggagagc cttgatttag | 3360 |
| gctacggcct cactctctat ggccacccta agaggaaagg ctacttcacc tcattacctc | 3420 |
| cagagggctg gcagggcca agtgcctcat aggactcatg ttctctccaa ccagggctgg | 3480 |
| catcactgct ttgcaaagtg gggcctgagg tagaagaagg tgtctggttt ctccagctgc | 3540 |
| tgtaggaggc taatgggcag ggtacttgcc cttgtccca ctagactcta acccagcacc | 3600 |
| agggtgccca cctaggacct ttcctggaca tgagtttcct tcactatcat agtcatgagc | 3660 |
| ctcctacttc tgggattgca gatcaggggt gggggagaa tgttgcatgt tgttttctgg | 3720 |
| tgcttgttat tatatatttg aataaacagt gctgcaagta cttgccatga aggatctga | 3779 |

<210> SEQ ID NO 23
<211> LENGTH: 636
<212> TYPE: DNA
<213> ORGANISM: Homo sapiens
<220> FEATURE:
<221> NAME/KEY: misc_feature
<222> LOCATION: (1)..(636)
<223> OTHER INFORMATION: variant sypl2

<400> SEQUENCE: 23

| | |
|---|---|
| ggctaagtgg ctttttgggta tcccttcagg ttgcaccgga tccaatatga gatgcccctc | 60 |
| tgcgatgaag agtccagctc caagaccatg cacctcatgg gggacttctc tgcacccgcc | 120 |
| gagttcttcg tgacccttgg catctttttcc ttcttctata ccatggctgc cctagttatc | 180 |
| tacctgcgct tccacaacct ctacacagag aacaaacgct tcccgctggt ggacttctgt | 240 |
| gtgactgtct ccttcacctt cttctggctg gtagctgcag ctgcctgggg caagggcctg | 300 |
| accgatgtca agggggccac acgaccatcc agcttgacag cagccatgtc agtgtgccat | 360 |
| ggagaggaag cagtgtgcag tgccggggcc acgccctcta gggcctggc caacatctcc | 420 |
| gtggtgagac ctgtggccac tgcaggaagc agcaccagcc tgctgcccca ggcctgtccc | 480 |
| agctagcagg tcctgaaagg aaagagaggg tgtcccagag ctggtgtccc ctgcacctgg | 540 |
| agctggtgcc ctcactgcgc ttcatgctgg ctgctggctc ctggctgacc ctgagaggac | 600 |
| attttgggat gagggggaacc caaaagccac ttagcc | 636 |

<210> SEQ ID NO 24
<211> LENGTH: 3403
<212> TYPE: DNA
<213> ORGANISM: Rattus norvegicus
<220> FEATURE:
<221> NAME/KEY: misc_feature
<222> LOCATION: (1)..(3403)

<400> SEQUENCE: 24

| | | | | | |
|---|---|---|---|---|---|
| gcggggcagc | gcggcggaca | gagcctccga | gagcgcgagc | agcagcgccc | ccacgaccca | 60 |
| gcccgccagc | ctggagcccg | gcctgccac | ggccgcgagc | ccgccgcccc | cagcgccccc | 120 |
| gcgcgccccg | cagcctcccg | gccagggagt | cgaaccccg | cactgcgccc | cgacgcgcca | 180 |
| gcatgtcctc | gacggagagc | cccggccgca | cctcggacaa | gtctccgcgc | agcaggtgg | 240 |
| accgcctgct | cctggggctg | cgctggcagc | gcctggagga | gccgctgggc | ttcatcaaag | 300 |
| ttctccagtg | gctctttgct | attttcgcct | tcgggtcctg | cggctcttac | agcggggaga | 360 |
| cgggagcctt | ggttcgctgc | aacaacgacc | ccaaggacgt | gagctccatc | attgttttgt | 420 |
| tcggctatcc | cttcaggttg | taccaggtcc | agtatgagat | gcctctctgt | gatgaggaat | 480 |
| ccacatccaa | aaccatgaac | ctcatgggag | acttctctgc | ccccgccgag | ttctttgtga | 540 |
| cccttggcat | cttttccttc | ttctatacaa | tggctgccct | ggtcatctac | ctgcgcttcc | 600 |
| acaaagtcta | cacggagaac | aaacgcttcc | cattggtgga | tttctgtgtg | accgtctctt | 660 |
| tcaccttctt | ttggctggtt | gctgccgctg | cctggggcaa | gggcttgact | gatgtcaaag | 720 |
| gggccacacg | gccatccagc | ctgactgcag | ccatgtctgt | gtgccatgga | gaggaggcag | 780 |
| tgtgcagtgc | tggggccacg | ccctctatgg | ggctggctaa | catctctgtg | ctctttggct | 840 |
| ttatcaactt | cttcctgtgg | gctggaaact | gttggtttgt | gttcaaagag | accccatggc | 900 |
| acggacaagg | ccaggaccag | ggccagggcc | ccagccagga | gagtgcagca | gaacagggag | 960 |
| cggtggagaa | gcagtaagca | gccctcatct | gcctactccc | caactggaca | tggacagcac | 1020 |
| cttctcatct | cctccagctt | ctacaggacc | ttcttcctcc | tcctcctccc | ttaccccatc | 1080 |
| actctggact | tgagatttg | agagaatgga | tgggtaggca | tcagctgttg | gtaacctggg | 1140 |
| cagaccccca | ctggctatcc | ctcatcctgc | tggggcagcc | aatggcagga | tctccgtgct | 1200 |
| tcttgtccgc | tgcctggagt | tgggcatctt | gctcgggcaa | gtcagctggc | aaccttgccc | 1260 |
| tgattcccgt | gtggagggcc | caccagtgac | tttgtgacat | ccctcggtag | ctgtcatcta | 1320 |
| atctgtatcc | tatctctagc | cctcccagag | ctcactgtgc | tccccaatct | cctctctggc | 1380 |
| ctctgtccat | agctctcacc | acgtgtgaag | cagggagacc | cattaccta | ccgaaggtcc | 1440 |
| ctctaggggt | ccacgtgaga | cccggaccca | gtgggagagg | atagagttgc | ctattgcagc | 1500 |
| accaaggaag | aaagtcagga | aagttgctgg | cagaatacgt | tttctgtccc | ctcagccctc | 1560 |
| cctctccctc | agctgaaaca | ctttcagtag | tgccctacac | tccacttatt | catgaaaccc | 1620 |
| cttacacct | tctccttctc | agccttggtt | ttgtctcaca | cttcggaaac | aagatggaat | 1680 |
| ggcttggaac | atttcccctt | cattttccca | tccccaccac | acctgtgggc | ccttctccct | 1740 |
| tccccaacct | tttggagatg | aggcatttaa | gatcttttca | aaagcctgcc | caggccttcc | 1800 |
| tttcattcct | gtgggctttg | ggagggcctg | aaggaccacc | ataaggctga | tgtgcccagg | 1860 |
| aatcccagga | catgaataca | cgggcccagt | tgtccccttac | tgtctgttca | ttttctcaag | 1920 |
| ccagctcctt | ttctagttct | ttcaaacctg | tccttcccat | cttaacaaag | agggttctct | 1980 |
| ctcctcatct | ctcacctcca | cacgtagcc | aggcccatc | ccttcccag | tcctgggcag | 2040 |
| cccgatgcta | ttggtgcttc | ttcacttcgg | gacccagttc | catatttgtc | tttggtgtgt | 2100 |

```
ctcctcttcc tgatacccc  ttcatcccct ttttgtcccc aaggccttag ggtaccaact    2160
gggtaaatgc catccgcctc ctacctagat caaaacccct tgatctaccc tggcagggtt    2220
gctcagggaa agtgaagaag gaagaaacca gccatttccc aatatagtgg caacgggccc    2280
acctaaatcc caaagatgaa tgtaccttgt gccaacctgt ccttaagaca cgatcaaccc    2340
tctccagccc ccttgcctct ctcaatgcta cccacatcaa gatgtattac ttgggtgccc    2400
agggctcaga atccttaact ctgggccatt catttcttct ttgggttaca atttccccac    2460
ccaacagaga agtatgatat ttacagacat tacagatgct cccaagccct tcagtaaaag    2520
aatttggaat ttttgttttc tgtttcagat tttagagaaa agatttgaga aggggaaaat    2580
ttgatgagga tgagaatgtt cctaaatctg aaactctcta tcctaagttg tcctcatggt    2640
tacttaagga caaggggag  agttttgcct acaactttag atatacaaag aacaaagggg    2700
tgaccatttt tcttcaagca agtccctgtg gggatctggg agcagcttct actcgaactg    2760
tgtttggatt ctgcgtccat atttataatt tatttgaact gtgatggata cagtgttctc    2820
atttagggcc taaggtagca actggcccat caactacttt agaaagggag ctgtccactc    2880
ccagtgagca ctcttactcc agagctctct ctagggttga gaaggctttt cttcagcaag    2940
agtctggcta tggccaaaag agccttaatt taggctatgg cctttctctc catggctgcc    3000
ctcagaggaa agaccagttc acctcattac ctccagggg  ctgggcagcc tgcgtgccaa    3060
gggcagctct gtcctcataa gactcatgtc ctctccaacc agggctggca ccagtacttt    3120
gtctagtcag gcctggacta ggagaaggtg tctggtttct ctagctatcg caggaggcca    3180
acaagcgggg aacttgccct ttgccctggt agactctgac catgtggaga tgaccatcta    3240
ggacctttct tagacatgag ttcccatcaa catcctgatg gtgggtctcc tacttctggg    3300
attgcagatt gagggcatgg ggagaatgtt gcatgttgtt ttgtggtgct tgttattaca    3360
cgtttgaata aacagtgctg cgaacagttg tcaagaagaa gcc                      3403

<210> SEQ ID NO 25
<211> LENGTH: 3247
<212> TYPE: DNA
<213> ORGANISM: Mus musculus

<400> SEQUENCE: 25
gcggggcagc gcggcggaca gagcctccga gagcgcgagc agcagcgccc ccacgaccca      60
gcccgccagc ctggagcccg gcctgcccac ggcctcgagc ccgccgcccc cagcgccccc     120
gcgccccacg cagcctcccg gccagggagt cgaacccttg cactgcgccc cgacgcgcca     180
gcatgtcctc gacggagagc cccggccgca cctcggacaa gtctccgcgc cagcaggtgg     240
accgcctgct cctggggctg cgctggcagc gcctggagga gccgctgggc ttcatcaaag     300
ttctccagtg gctctttgct attttcgcct tcgggtcctg cggctcttac agcggggaga     360
cgggagcctt ggttctctgc aacaacgaag ccaaggacgt gagctccatc attgttttgt     420
tcggctatcc cttcaggttg taccaggtcc agtatgagat gcctctctgt gatcaggact     480
ccacctccaa aaccatgaac ctcatgggag acttctctgc cccgccgag  ttctttgtga     540 cccttggcat cttttccttc ttctacacaa tggctgccct ggtcatctac ctgcgcttcc     600
acaaactcta cacagagaac aaacgcttcc cgttggtgga tttctgtgtg actgtctctt     660
tcaccttctt ttggctggtt gctgccgctg cctggggcaa gggcttgact gacgtcaaag     720
gggccacccg gccatccagc ctgactgcag ccatgtctgt gtgccatgga gaggaggcag     780
tgtgcagcgc cgggggccaca ccctctatgg ggctggctaa cctctctgtg ctctttggct     840
```

| | |
|---|---|
| ttatcaactt cttcctgtgg gctggaaact gttggtttgt gttcaaagag accccgtggc | 900 |
| acggacaagg ccaggaccag ggccagggcc ccagccagga gagtgcagcg gagcagggg | 960 |
| cagtggagaa gcagtaagca gccttcatct gcctactccc caactggacg gcaccttgtc | 1020 |
| agctcctcca gcttctacag gacctcctcc tcttcctctt cctcctgctc ctcctctccc | 1080 |
| tcctcctcca actcccttcc cccatcattc tggactttga gatttgagag aatggatggg | 1140 |
| tgggcatcag ctgttggtaa cctgggcaga cctccactgg cttcctatcc ctcatcctgc | 1200 |
| tgggcagca acggcagga tctcagtgct tcttgtctgc tgcctggact gaagcatctt | 1260 |
| acttggggaa gctgactggc aaccttgccc tgagttctgt gtggagggcc caccagtgat | 1320 |
| tttgtggcat ccctcaataa ctggcatcta atctgtatcc tatctctagc cctcccagag | 1380 |
| cccagtgtgc tcccaccatg tgtgaagcag ggagacccat tatcctatca gaggtccctc | 1440 |
| taagggtcca catgagaccc ggacccaatg ggagcagaga gagttgcaag tacattgcag | 1500 |
| caccaaggaa gaaagtgagg aaagttgctg gcagaataag ttttctgttc cctcagccct | 1560 |
| tcctttccct cagctggaac actttcggta gcaccctata caccacttac tcatgaaacc | 1620 |
| ccttactccc ttctccttct cggccttggt tttgtgggct ttgggagggc ctgaaggacc | 1680 |
| atcgtgacat gagatgccca ggagtcccgg acaaggata catgggccca cctgtccctt | 1740 |
| accgtctgtt cattttctca agccagcacc ttttctagtt ctttcaaacc tttctgtccc | 1800 |
| atctttacaa agagggttat ctgtccttgt ctctcgcctc catgcagtag ccaggcccca | 1860 |
| tccttcccca gtcctgggca gcccgatgct attggtgctt cttcatttcg ggacccagat | 1920 |
| ccatatttgt ctttggtgtg tctcctctcc ctgattcctc ctgtcatccc tctttgggcc | 1980 |
| cgaaggccag agggtaccaa ctgggcaaat gccatctgcc ttttacccag atcaaaaccc | 2040 |
| cttgatctac cctggcagta gggttgctta gggaaagatg ataaagaagg aagaaaccag | 2100 |
| ccgtttccca atttagtggc aattgtccca cttagcaccc caaagatgaa tgtaccttgt | 2160 |
| gccaacctgt cctcatgaca tgatcgaccc tctccaaccc ccttgccttc tcaatgcta | 2220 |
| cccacatcaa gatgtatttc ttggggggcc agggctcaga atccttaact ttgggctgtt | 2280 |
| catttcttct ttgggttaca attcccccac ccttcagagg aagtaggata tttacacact | 2340 |
| ttcagatgct cccgagccat tcagtaaaat aatttggaat ttttgttttc tgcttaagat | 2400 |
| tttagggaaa agatttaagg aggggaaaat ttgatgaggg tgagaatgat cctaaatctg | 2460 |
| aaactctcta tcctaagttg tccccatggt tacttaagga caagggagac agttttgcct | 2520 |
| ccagctccag aggtacaaag aacaaaagag tgaccatttt tcttcaaaca agtccctgtg | 2580 |
| gggatctggg agcagcttcg actcaaactg tgttttggatt ctgcgtctat atttataatt | 2640 |
| tatttgaact gtgacggata aagtgttctc atttggggcc caagttagca actggcccat | 2700 |
| caactacttt agagtaggag ttatccactc ccaccgagca ttcgtactcc agggctcgct | 2760 |
| ctagggttga aaaggctctt cctggcaaga gtctggctat ggccaagaga gtcttgattt | 2820 |
| aggctatggt ctttccatgg ccgccggaag aggaaagacc agttcacctc attacctcca | 2880 |
| gggggctggg cagcagtaag tgccaagggc agctctgtcc tcatgagact cgtgtcctct | 2940 |
| ccaaccaggg ctggcaccac cactttgcct agtcaggcct gaagcgggag aggtgtctgg | 3000 |
| tttctctagc tattgcagga ggccaacaag cagggaactt gcccttttgcc ctggtagact | 3060 |
| ttaccatgtg gagacgccta tccaggacct ttcttagaca tgagtcccct tcaacatcct | 3120 |
| gaccatgggc ctcctatttc tgggattgca gatcgaggat gtggggagaa tgttgcatgt | 3180 |
| tgttctgtgg tgcttgttac tacacatttg aataaacagt gctgcgaaca tttgccaaga | 3240 | agaagcc 3247

<210> SEQ ID NO 26
<211> LENGTH: 1897
<212> TYPE: DNA
<213> ORGANISM: Xenopus laevis
<220> FEATURE:
<221> NAME/KEY: misc_feature
<222> LOCATION: (1)..(1897)

<400> SEQUENCE: 26

```
gtgagaaggt gacagaggga gagaggaggg aggaggcaaa aagggcagaa agccaggggc      60
taagtgagtc tggggcacag gaacgagact ggatataagg gatacaaata tacaaccact     120
ttggcaggtt gcatgtgact taatgaagca gtagaaatat cttaaaattg tcagtaaata     180
acaaaaagga tattttagc cttatttaca gaatacccag agaacgatat tggaacagtg      240
ataccaaatt acagtaagca gttaaataag gacgtaactg cattacaaat agtagtaggt     300
acataaaaaa gtaacaggtt tacagaaact ggtcatcaag aggagccgac atactctctt     360
tacttggata cttgagccct tctgttcaga cttccagcca ctcacccgtg ggcaccttta     420
aacaaggacc atgtcaacag cagttccctc ctcaacgatg gacagattgg ggggccttgc     480
aggacttggc aagaagaacc catttgccgg actacgctgg aggaggttag aggagccatt     540
gggattcatt aagttgctgg aatggctgtt tgctatattt gcctttggaa gttgtgggtc     600
atacagtgga gagacagcag caactgtcat gtgcaagtca gaagcagaca cagaaataaa     660
gctaatttcg gttccctttg gatacccatt caggctgtat cgccaacgct atgagatgcc     720
agcttgtgac gatatggaaa ggcgtattct ccatctgaca ggggatttct ctgcccctgc     780
agagttcttt gtgacaatgg gagtctttgc attcctatac gccatgtttg cactggttat     840
ctatttacgt ttccatgaag aatacaccaa aatccgcaga ttgccaattg tggatttgtg     900
tgtgactggc gccttcacct ttttgtggct tgtggcagct tcagcttggg gaaaaggcct     960
gatggatgtg aagtggcta ctcaaccttc cagccttgtc tcatcaatgc ctctctgcca    1020
aatgaaaaaa gccacatgca atgctggctc ttcaccatat tttgcccttg ctaacatatc    1080
tgtgctcttt ggctttctga atttcattat ctgggctgcc aatatatggt ttgtgtttaa    1140
agagaccaca tggagtaaga aacctgcctc caaggaagaa tctgcagagc gtggagaggt    1200
tgaagaccac tagtgatacc tgacaaacat attcctgggt ttccaacaca tactcttacc    1260
ctactgaaat tctaggactg agtcccattc accttcttct ttaccaggct tcaaataatc    1320
aactgttcaa ttcttttatga ccttttatta tttaccctga cactgcccac atatagcgaa    1380
tatgattaat gttccaaaaa catacatagg tgcttataaa aaaagcttat tgtagggttg    1440
gttgcactgt atttaataca gcccagcata cagcatatat atgttacaat caggcctgga    1500
ctgggattca aaataggccc tggattttca agtatataga ggcagataca gcccccacca    1560
gcccatgact ttctttggaa tcttacgaaa gcccctctgg cattttgcca gaatctgcag    1620
attgccagtc tgggcctggt tacaataagt aacccagttt ataccaaacc gtaaacacaa    1680
atgaattaac gcagggttga attctttata atgcagtcta taacagtatt tattttttaaa    1740
tatgtgccct actgtaaagg acagtactga ttcatattat gctttctatt agaattgtct    1800
cctgtccttt tcaaagaaaa taacctttct cacctgtcca cagtgtctct ggtgctattt    1860
attaaataaa aacaaatatt ctaaaaaaaa aaaaaaa                              1897
```

<210> SEQ ID NO 27

```
<211> LENGTH: 223
<212> TYPE: DNA
<213> ORGANISM: Homo sapiens
<220> FEATURE:
<221> NAME/KEY: misc_feature
<222> LOCATION: (1)..(223)
<223> OTHER INFORMATION: HUMAN MG29 PROMOTER SEQUENCE

<400> SEQUENCE: 27
cagagtcttg gactgtcgcc agggctggag cggctcactg caacttccac ctcccgggtt        60
caagcaattc tcctcctgag tagctgggat tacacacatc accacacccg tgtattttta       120
gtagagacgg ggtttcacta tgttggccag ctcgaactcc tgactcgtga tcttctggcc       180
tcggcctccc aaatgcaggc gtgagccacc aagcctggcc aat                         223

<210> SEQ ID NO 28
<211> LENGTH: 38
<212> TYPE: RNA
<213> ORGANISM: Artificial Sequence
<220> FEATURE:
<223> OTHER INFORMATION: Synthetic shRNA sequence
<220> FEATURE:
<221> NAME/KEY: misc_feature
<222> LOCATION: (1)..(38)
<223> OTHER INFORMATION: shRNA

<400> SEQUENCE: 28
cugcaguggc gccgccugaa gucucugauu aauaguga                                38
```

COMPOSITIONS COMPRISING MG29 NUCLEIC ACIDS, POLYPEPTIDES, AND ASSOCIATED METHODS OF USE

CROSS-REFERENCE TO RELATED APPLICATIONS

Under 35 U.S.C. §119(e) this application claims the benefit of the following U.S. Provisional Patent Applications: Ser. No. 61/135,325 filed: Jul. 18, 2008, entitled: MG29 and Muscle Function in Stress and Disease; and Ser. No. 61/212,275 filed: Apr. 8, 2009, entitled: Compositions Comprising MG29 Nucleic Acids, Polypeptides and Associated Methods of Use, all of which are hereby incorporated by reference in their entirety for all purposes.

INCORPORATION BY REFERENCE

In compliance with 37 C.F.R. §1.52(e)(5), an electronic CRF of the sequence listing is filed herewith: file name: MG29_seqlist_ST25.txt; size 67 KB; created on: Jul. 14, 2009; using PatentIn-3.5, and Checker 4.4.0 is hereby incorporated by reference in its entirety. The data in the Computer Readable Form of the Sequence Listing submitted herewith contains no new matter, and is fully supported by the priority applications, U.S. Provisional Patent Applications Nos. 61/135,325; and 61/212,275.

STATEMENT REGARDING FEDERALLY SPONSORED RESEARCH

The U.S. Government has certain rights in this invention pursuant to the following grants: RO1-AG15556 awarded to Dr. Jianjie Ma by the United States National Institutes of Health (NIH).

FIELD OF THE INVENTION

This invention relates to recombinant nucleic acid and polypeptide compositions and methods of use thereof for the modulation of muscle function and treatment of disease.

BACKGROUND

The triad junction of skeletal muscle is comprised of a single invagination of the plasma membrane that plunges into the cytoplasm (the transverse-tubules or T-tubules) that is juxtaposed with two sections of the terminal cisternae of the sarcoplasmic reticulum (SR). Screening of an antibody library for novel proteins that localize to the triad junction by immunostaining identified proteins that are implicated in excitation-contraction (E-C) coupling and other aspects of $Ca^{2+}$ handling in skeletal muscle. One protein identified during the screening of this library was a novel transmembrane protein called, synaptophysin-like 2 protein (Sypl2) or mitsugumin 29 (MG29).

MG29 is nearly exclusively expressed in skeletal muscle fibers, although some minor levels of expression can be resolved in the kidney, and contains four transmembrane domains that allow the protein to localize at both the transverse (T-) tubular membrane and SR membranes of the triad junction. This subcellular distribution suggest MG29 may mediate communication between the T-tubular and junctional SR membrane. The protein structure of MG29 is homologous in amino acid sequence and shares characteristic structural features with the members of the synaptophysin family of transmembrane proteins essential for neurotransmitter release.

Synaptophysin was originally identified as an abundant and highly immunogenic membrane protein of small synaptic vesicles that is also found in dense-core chromaffin and neurosecretory granules. Synaptophysin and its homologues, synaptoporin (or synaptophysin II) and pantophysin, share a common transmembrane organization, with four membrane-spanning regions and cytoplasmic amino and carboxy termini.

A unique feature of synaptophysin is that it has an oligomeric structure, leading to the proposal that synaptophysin may be a component of the fusion pore that forms during neurotransmitter release. Moreover, Alder et al. have shown that antisense oligonucleotides complementary to the synaptophysin mRNA reduce $Ca^{2+}$-dependent glutamate secretion from *Xenopus* oocytes induced by injection of total brain mRNA. Microinjection of synaptophysin antibody into motor neurons blocked neuromuscular transmission. These data are consistent with synaptophysin being essential for neurotransmitter secretion. However, genetic approaches to identify the function of synaptophysin have not been successful; mutant mice lacking synaptophysin show a normal phenotype. This may reflect compensation by synaptoporin or other synaptophysin family members. Indeed, mice doubly deficient in synaptophysin and synaptogyrin display defects in synaptic plasticity.

Synaptophysin has been proposed to play a structural role in vesicle formation. Based on its high capacity to bind cholesterol, synaptophysin has been implicated in the generation of membrane curvature during synaptic vesicle biogenesis. Synaptophysin is also known to tightly interact with other proteins of the synaptic vesicle membrane, i.e. synaptobrevin and the vacuolar $H^+$-ATPase. These interactions are thought to regulate exocytotic membrane fusion at the level of the SNARE complex or fusion pore formation. The latter idea is supported by studies on yeast vacuole fusion that implicate the vacuolar ATPase directly participate in membrane fusion.

The similarities between MG29 and synaptophysin prompted an investigation into whether MG29 plays an important role in modulation of membrane structures in skeletal muscle. Skeletal muscles are among the most plastic tissue in nature, and normal muscle physiology requires the formation and maintenance of the complex membrane structures. Throughout development, aging and other processes including fatigue require constant adaptations of the skeletal muscle system, thus identification and characterization of genes and proteins involved with plasticity in skeletal muscle membrane structures is essential to understand muscle physiology, as well as treating and diagnosing pathologies related to muscle dysfunction. Accordingly, there exists an ongoing need for the development of pharmaceutical modulators of muscle function for the treatment of conditions related to muscle dysfunction.

SUMMARY

The invention relates to the surprising and unexpected discovery of genes, proteins, and processes involved in excitation-contraction (EC) coupling in muscle cells. In particular, The present invention provides nucleic acids encoding MG29 and/or MG29 receptor polypeptides and portions thereof (herein "MG29 polypeptides"), nucleic acids complementary to nucleic acids encoding MG29 and/or MG29 receptor polypeptides and portions thereof, vectors and/or host cells comprising the same, MG29 and/or MG29 receptor polypeptides and fusion proteins, antibodies or antigen-binding domains specific for an epitope of MG29, host cells and transgenic organisms in which the expression of an endogenous MG29 and/or MG29 receptor gene or exogenous MG29 and/or MG29 receptor transgene is modulated.

In additional aspects, the invention relates to diagnostic assays and methods of screening for chemical compounds that modulate the activity, transcription, and/or translation (i.e., expression) of MG29 and/or MG29 receptors, and methods of using the same.

In further aspects, the present invention also relates to compositions useful as therapeutics for treating and prevention of diseases and disorders related to muscle dysfunction. Therapeutic compositions of the invention comprise MG29 and MG29 receptor polypeptides and fusion proteins, nucleic acids encoding MG29 or MG29 receptor polypeptides, and nucleic acids complementary to nucleic acids encoding MG29 or MG29 receptors, including ribose-containing nucleic acids. This aspect of the invention also encompasses MG29 and MG29 receptor mutants, homologs, fragments, truncations, pseudopeptides, peptide analogs, and peptidomimetics.

In another aspect, the invention encompasses compounds that can modulate at least one of MG29 gene expression, protein level, and/or activity; and/or MG29 receptor gene expression, protein level, and/or activity. As described herein, MG29 is an important constituent of cellular structures and physiological processes critical for normal muscle function. As such, the targeting and modulating MG29 and/or MG29 receptor gene expression, polypeptide synthesis, activity or protein-protein interactions represents a novel therapeutic intervention for treating pathologies relating to muscle dysfunction, including, for example, sarcopenia, fatigue, as well as many others.

In certain additional aspects the invention relates to compositions and methods related to the diagnosis, treatment or amelioration of muscle related pathologies. In certain exemplary embodiments, the invention encompasses, for example, the administration of an effective amount of a therapeutic composition of the invention for the prevention and/or treatment of muscle related pathologies; including treatment and/or prevention of age-related deficiencies in muscle function that occur as a natural side-effect of the aging process (including sarcopenia); treatment and/or prevention of injury to any type of muscle tissue, such as for example, those occurring in subjects suffering from cardiovascular diseases and/or sports-related injuries; the treatment and/or prevention of muscular dystrophy, cardiac ischemia, heart failure, aging degeneration, and the like. In certain embodiments, the therapeutic composition comprises a nucleic acid, including interfering nucleic acids that modulates at least one of MG29 gene expression, protein level, and/or activity; and/or MG29 receptor gene expression, protein level, and/or activity; and/or a small molecule capable of modulating MG29 gene expression, protein level, and/or activity; and/or MG29 receptor gene expression, protein level, and/or activity.

In other embodiments, the invention relates to diagnostic compositions useful for diagnosing or monitoring a disease or condition related to muscle function comprising a nucleic acid that is complementary to or capable of hybridizing to at least a portion of an MG29 or MG29 receptor encoding nucleic acid, for example, an MG29 or MG29 receptor gene or mRNA.

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional objects and advantages are expressly included within the scope of the present invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

FIG. 2. Dose- and time-dependent activation of MG29 expression by doxycycline using transgenic system. (A) HEK293 cells were transfected with the MG29 cDNA transgene construct and treated with various doses of doxycycline. After 24 hours of exposure to doxycycline the cells were lysed for biochemical assays. Western blot for the Flag tag on the MG29 cDNA shows that MG29 expression can be induced in response to increasing doses of doxycycline. β-actin levels are provided as a control for gel loading. (B) HEK293 cells were transfected with the MG29 cDNA transgene construct and treated with 0.1 ug/mL doxycycline for various times. After the indicated times, the cells were lysed for Western blot analysis. A time dependence for the activation of MG29 expression could be observed with this transgenic system.

FIG. 5. Dose-dependent repression of gene expression by doxycycline using transgenic system. (A) HEK293 cells were co-transfected with a plasmid containing junctophillin-1 (mJP1) and the transgenic plasmid containing siRNA sequences that target the mJP1 cDNA. These cells were then treated with various doses of doxycycline. After 24 hours of exposure to doxycycline the cells were lysed Western blot for mJP1 expression. The blot shows that mJP1 expression can be repressed response to increasing doses of doxycycline. β-actin levels are provided as a control for gel loading. (B)

HEK293 cells were co-transfected with a plasmid containing junctophillin-2 (mJP2) and the transgenic plasmid containing siRNA sequences that target the mJP2 cDNA. These cells were then treated with various doses of doxycycline. After 24 hours of exposure to doxycycline the cells were lysed Western blot for mJP1 expression. The blot shows that mJP2 expression can be repressed response to increasing doses of doxycycline.

FIG. 6. MG29 protein expression is downregulated in aging and upregulated by exercise. (A) MG29 protein levels decrease in skeletal muscle as mice aged (image from Weisleder, et al., 2006, *J Cell Biol.*, 174:5, 639). (B) Mice were subjected to a single bout of treadmill exercise, then muscles were dissected and examined for MG29 expression at various timepoints after the cessation of exercise. There is an immediate increase in MG29 expression that continues and reaches a peak at 24 hours after exercise. MG29 levels begin to return to baseline as time progresses. Actin levels are provided as a control for loading variation.

FIG. 7. MG29 expression is controlled at the post-translational level in muscle cells. (A) C2C12 myogenic cells differentiated into myotubes and then harvested at different time points as shown. MG29 proteins levels were measured by Western blot using an anti-MG29 monoclonal antibody. No protein expression in observed in the C2C12 cells, while MG29 protein can be observed from HEK293 non-muscle cells that were transfected with pcDNA-MG29, an expression plasmid that contains the complete murine MG29 mRNA sequence, including the 3' UTR (+). (B) When the same cell samples are tested for MG29 mRNA expression by real-time PCR substantial levels of MG29 mRNA can be detected. This indicates that MG29 expression is controlled at the post-transcriptional level within muscle cells.

FIG. 8. 3' UTR in mouse and human MG29 mRNA considerably longer than average. The table (Mignone, et al. *Genome Biology* 2002, 3(3)) displays the average length of regions within a mouse or human mRNA. Numbers below the table display the length of each region in the mouse and human mRNAs. In both humans and mice, the 3' UTR for MG29 is much longer than the average length of a 3' UTR for these organisms.

Figure 9:
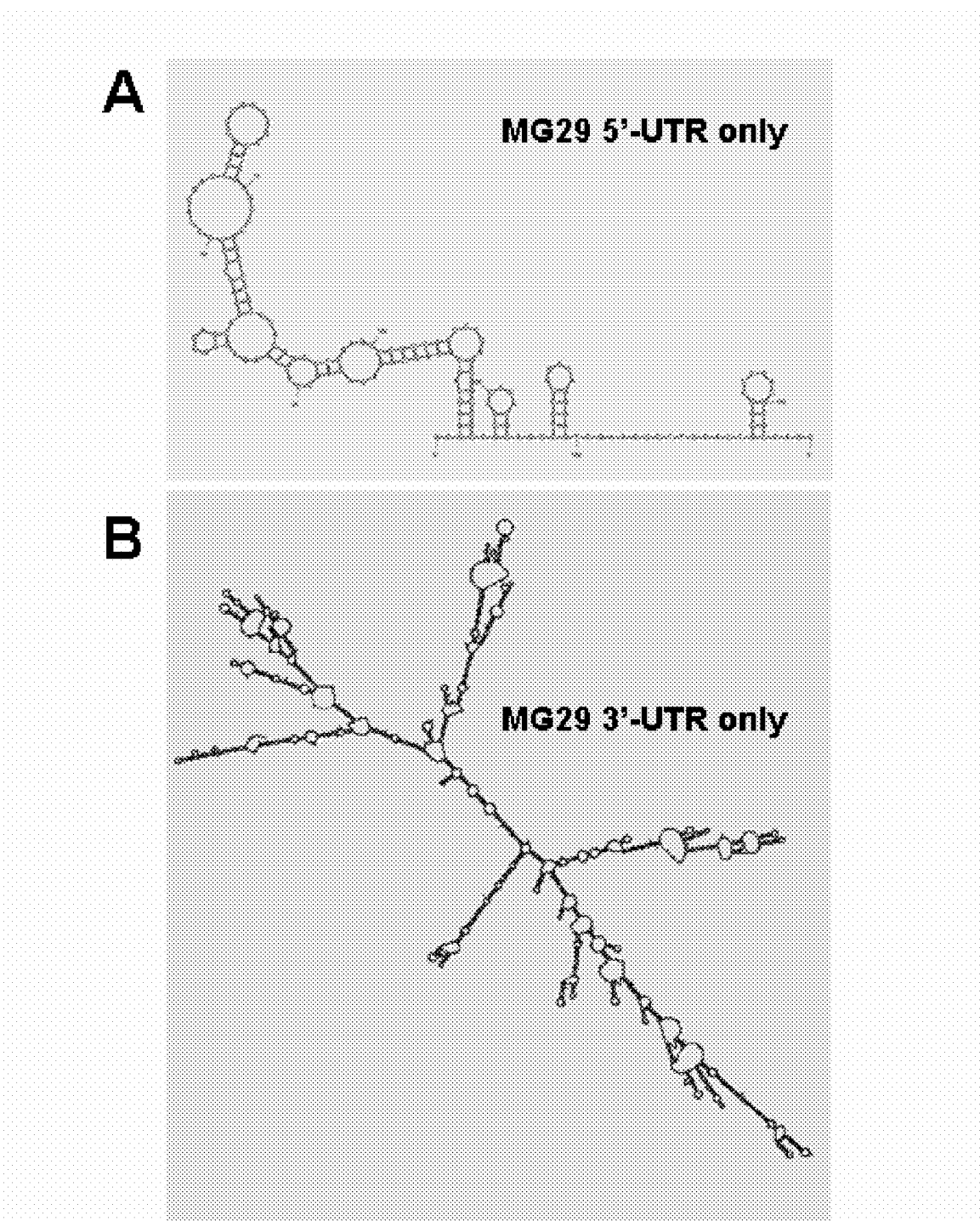

FIG. 9. Major secondary structure is present in the UTR regions of MG29. The sequence of the 5' and 3' UTR sequences were examined through bioinformatics approaches to resolve the secondary structure of these regions. While some hairpin structures are expected in the 5'UTR (A), the structure of the 3'UTR (B) is highly complex and provides multiple sites for binding of accessory factors that could affect the post-transcriptional regulation of MG29 gene expression.

Figure 10:
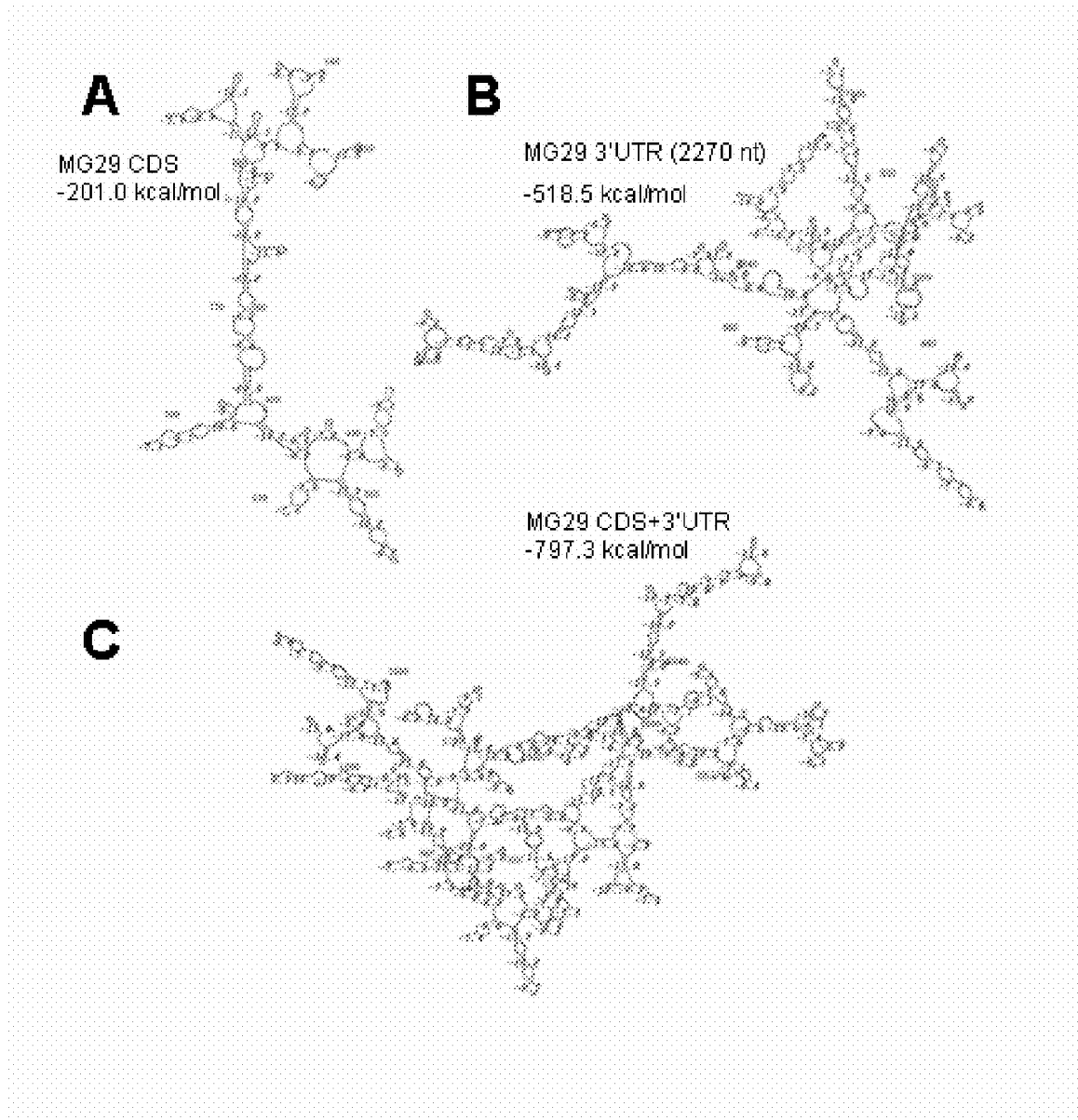

FIG. 10. The 3' UTR can greatly alter the characteristics of the mg29 mRNA. While the mg29 coding sequence itself (A) has a predicted free energy of −201.0 kcal/mol and a relatively simple secondary structure, the mg29 3' UTR (B) has a significant change in the free energy (−518.5 kcal/mol) and a more complex structure. This increased complexity and changes in the free energy is increased even further when the two sequences are combined (C), resulting in a free energy of −797.3 kcal/mol.

Figure 11:
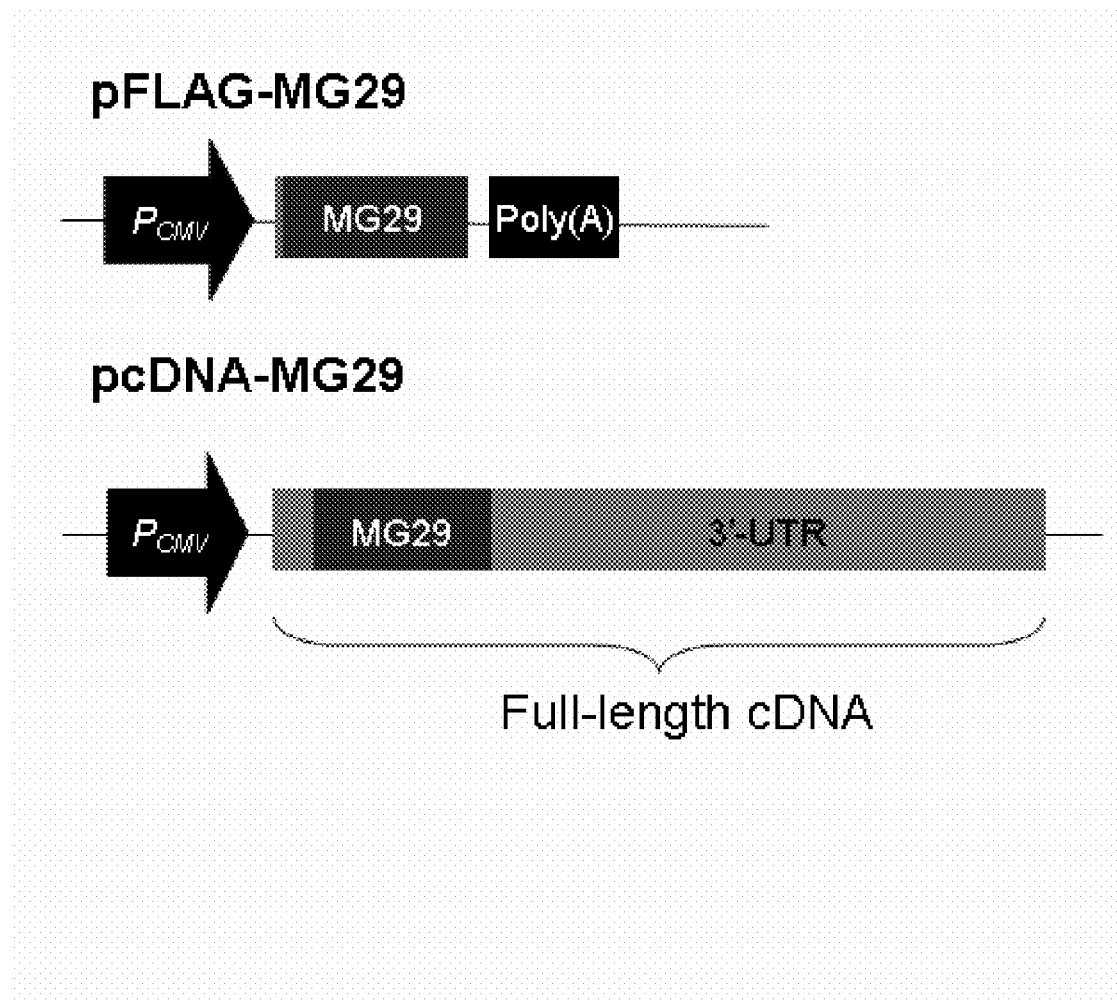

FIG. 11. Schematic diagram of recombinant plasmid vector constructs used in MG29 expression experiments: pFLAG-MG29 (containing no UTR) or pcDNA-MG29 (containing UTR). pFLAG-MG29 is an expression vector that contains only the coding sequence from the murine MG29 gene fused to a FLAG tag (DYKDDDDK). pcDNA-MG29 is a expression vector that contains the full length cDNA and both the 5' and 3' untranslated regions (UTR) of the murine MG29 mRNA. Note that both plasmids use the same promoter to drive expression of the expression cassette.

Figure 12:
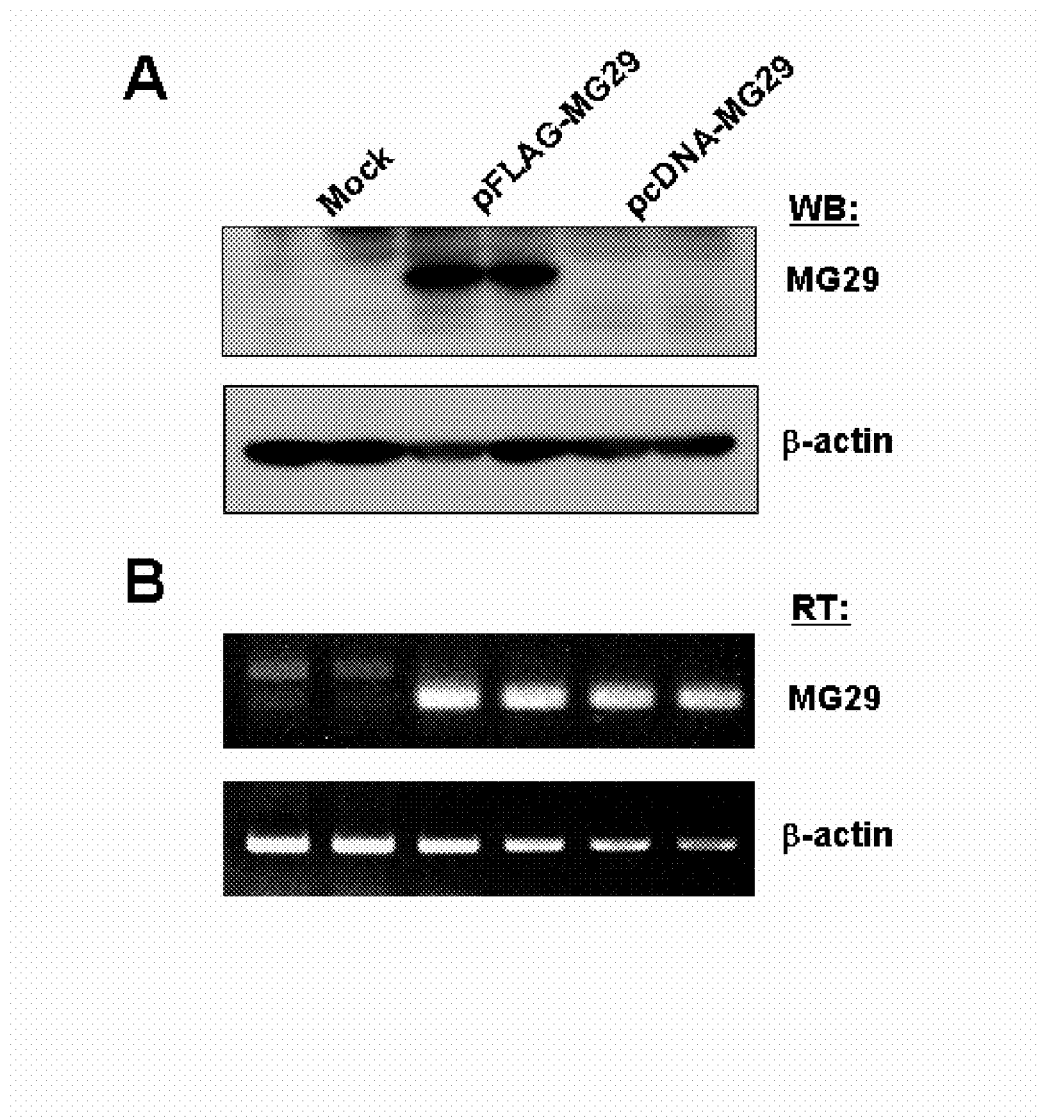

FIG. 12. UTR sequences are necessary for control of MG29 protein production in muscle cells. C2C12 cells were transfected with either pFLAG-MG29 (containing no UTR) or pcDNA-MG29 (containing UTR). Experiments were performed in duplicate with different wells loaded into separate lanes. Protein expression (A) was measured by Western blot (WB) and mRNA levels (B) were measured by semi-quantitative RTPCR (RT). While both plasmids could produce mRNA, only pFLAG-MG29 could produce protein expression under these conditions. This indicates that the sequence elements for post-transcriptional control of MG29 expression are present in the UTR sequences in the MG29 mRNA. β-actin levels are provided for a control for equivalent experimental conditions between samples.

Figure 13:
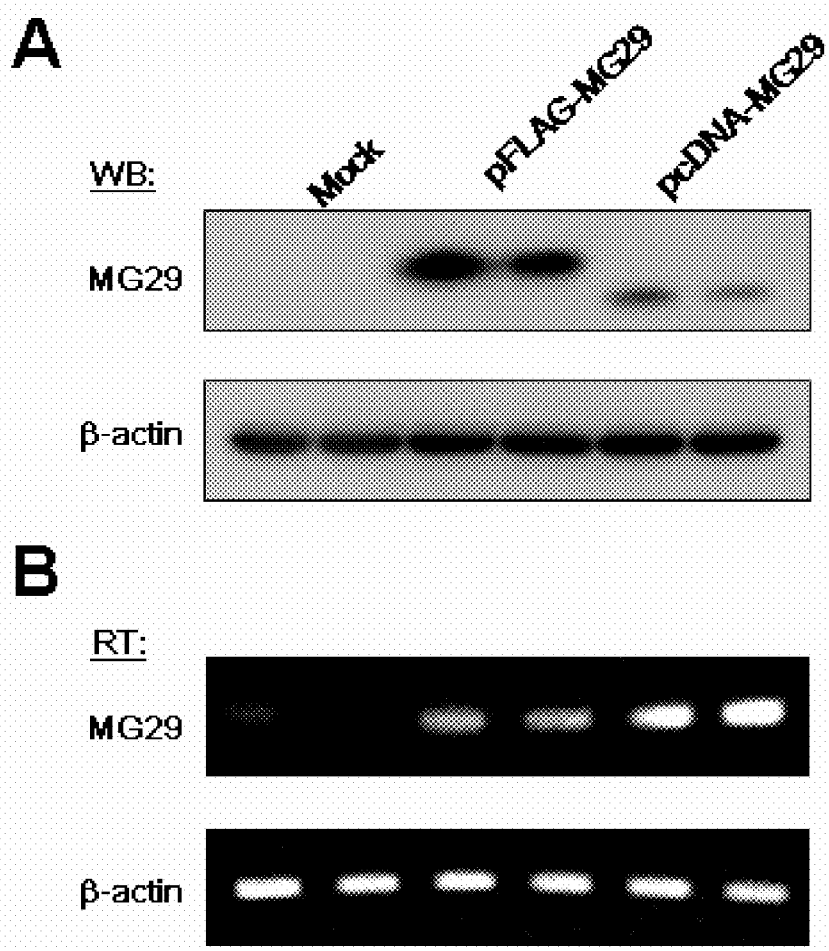

FIG. 13. Post-transcriptional regulation of MG29 expression is limited in non-muscle cells. HEK293 cells were transfected in the absence of Fetal Bovine Serum (FBS) with either pFLAG-MG29 (containing no UTR) or pcDNA-MG29 (containing UTR). Protein expression (A) was measured by Western blot (WB) and mRNA levels (B) were measured by semi-quantitative RTPCR (RT). While both constructs produced MG29 mRNA and protein, the presence of MG29 UTR sequence greatly reduced the amount of MG29 expression. β-actin levels are provided for a control for equivalent experimental conditions between samples.

Figure 14:
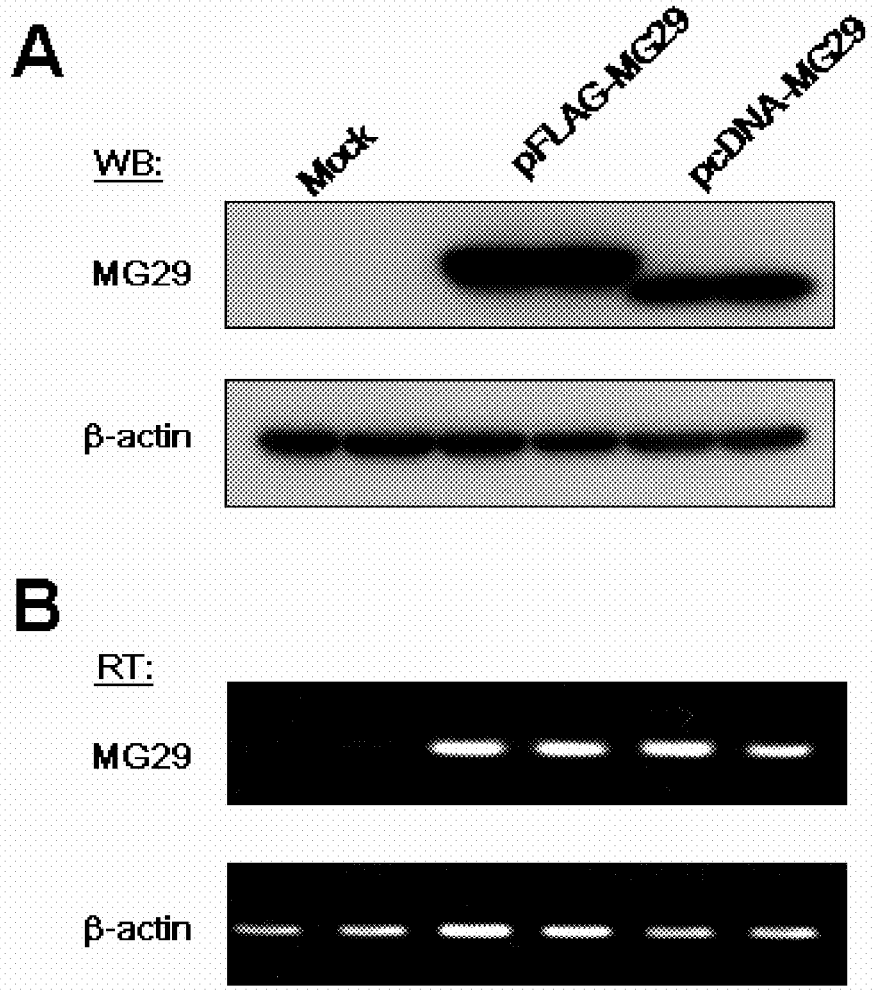

FIG. 14. Addition of FBS to the culture media can relieve inhibition of MG29 expression. HEK293 cells were transfected in the presence of FBS with either pFLAG-MG29 (containing no UTR) or pcDNA-MG29 (containing UTR). Protein expression (A) was measured by Western blot (WB) and mRNA levels (B) were measured by semi-quantitative RTPCR (RT). The addition of FBS in the culture media produced higher levels of MG29 protein in all cases, and greatly reduced the differences in gene expression between pFLAG-MG29 and pcDNA-MG29. This suggests that factors present in FBS can modulate the pathways that affect post-translational expression of MG29 expression. β-actin levels are provided for a control for equivalent experimental conditions between samples.

FIG. 15. Specific elements in the 3' UTR of the mg29 mRNA are essential for post-transcriptional regulation. (A) A series of deletion constructs were assembled of the 3' UTR of the full-length murine mg29 mRNA. These expression plasmids contained the MG29 coding sequence and various deletions of the 3' UTR. (B) These deletion constructs were transfected into C2C12 myoblasts cells and after 3 days the cells were lysed for analysis by Western blot. While the mg29 coding sequence (Fg-MG29) an express readily in C2C12 cells, the full-length (FL) mRNA does not produce MG29 protein in C2C12 cells. Deletion constructs F1 and F2 do not produce MG29 protein, however the F3 and F4 constructs can produce ample protein. This indicates that the specific region at the 3' end of the UTR of the mg29 mRNA is required for post-transcriptional regulation of the MG29 expression.

FIG. 16. Multiple consensus binding sites are located in the MG29 3' UTR. Computer database analysis reveals that the 3' UTR of the murine MG29 mRNA contains multiple binding sites for protein factors associated with stress-related post-transcriptional control of gene expression. For example, HuR sites regulate the stability and translation of mRNA in response to stress, such as oxidative stress. ARE (AU rich Element) are associated with mRNA destabilization. 15-LOX-DICE (15-LipOXygenase DIfferentiation Control Element) are bound by hnRNP E1 and K to inhibit initiation of translation.

Figure 17:
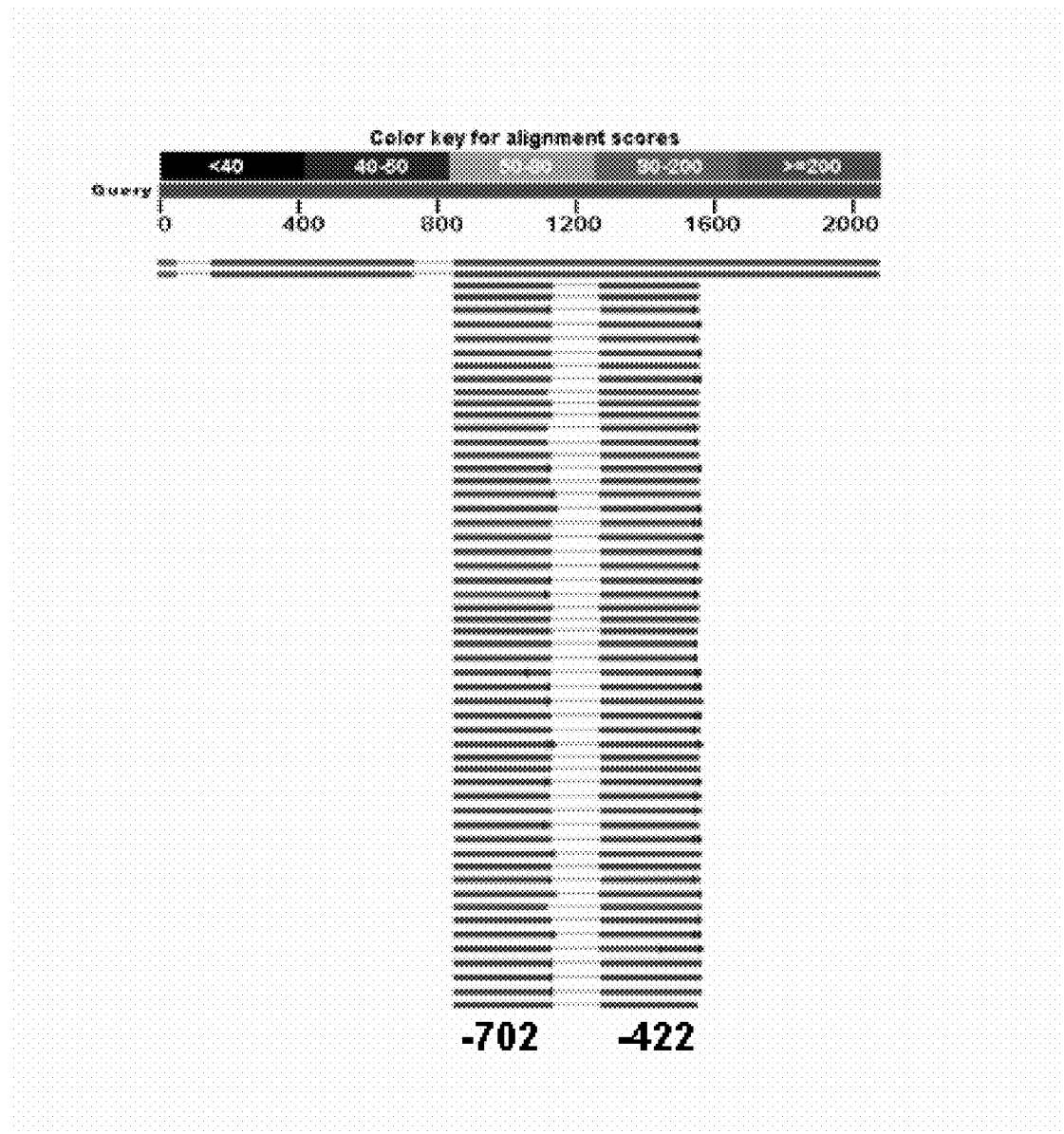

FIG. 17. The upstream sequence of the human MG29 gene contains a highly conserved region. The sequence 2 kb upstream of the transcription initiation site for the human MG29 gene was used for a BLAST search of the non-repetitive genomic database in GenBank. This search revealed a region at −702 to −422 from the transcription initiation site that was highly conserved with a number of primate species, including chimpanzee, marmoset and gorilla.

FIG. 18. Conserved region of human MG29 promoter contains consensus binding sites associated with muscle atrophy. The region at −702 to −422 from the transcription initiation site of the human MG29 gene was subjected to database analysis for consensus transcription factor binding sites (http://www.cbrc.jp/research/db/TFSEARCH.html). Several sites associated with control of muscle-specific gene expression we observed, including GATA, RUNX1, SREBP1, C/EBP and p300. RUNX1 is of particular interest as it has been directly linked to the progression of muscle atrophy similar to the sarcopenia observed in aged skeletal muscle.

DETAILED DESCRIPTION

Presently described are compositions and methods relating to the surprising and unexpected discovery that MG29 is an important structural and functional component in the excitation-contraction (E-C) coupling processes that governs muscle function and plasticity.

The following U.S. Provisional Patent Applications: Ser. No. 61/135,325 filed: Jul. 18, 2008, entitled: MG29 and Muscle Function in Stress and Disease; and Ser. No. 61/212,275 filed: Apr. 8, 2009, entitled: Compositions Comprising MG29 Nucleic Acids, Polypeptides and Associated Methods of Use, are hereby incorporated by reference in their entirety for all purposes.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In the case of conflict, the present specification, including definitions, will control. In addition, the materials, methods, and examples are illustrative only and not intended to be limiting.

The present invention describes compositions and methods which are surprisingly and unexpectedly beneficial for diagnosing, treating, and/or preventing muscle disease and dysfunction. While aging effects on muscle function have been associated with muscle fiber denervation, loss of motor units, and motor unit remodeling, functional alterations occur before significant muscle wasting becomes evident. Therefore, changes in E-C coupling machinery and intracellular Ca homeostasis may act as causative factors for, or adaptive responses to, muscle aging. Altered function of several triad junction proteins, including DHPR, calsequestrin and SERCA, have been shown to contribute to disrupted Ca homeostasis in aged skeletal muscle. Recently, the identification of molecular markers of muscle aging, and their contribution to aging-related muscle dysfunction has emerged as a major focus in E-C coupling studies and geriatric medical research in general.

Therefore, in a number of aspects, the invention restates to a number of important discoveries described herein that relate to MG29 function. For example, it has been observed that mg29 (−/−) knockout animals were not able to sustain physical activity for extended periods of time and run significantly less than wild type littermate controls. It was subsequently observed that muscle from mg29(−/−) mice fatigued to a greater extent, recovered to a lesser extent after fatigue and produced less force, even in the presence of caffeine, than wild type control mice.

Using biochemical assays, it was observed that the expression of MG29 is significantly decreased in aged skeletal muscle. Moreover, abnormalities of membrane ultrastructure around the triad junction were detected in skeletal muscle from both young mg29(−/−) and aged wt mice. For example, the t-tubule was swollen and sometimes missing from the A-I junction, and the SR networks were poorly formed with vacuolated and fragmented structures, leading to misalignment of triad junctions. Also, as described in detail below, the UTR sequences of the endogenous MG29 mRNA comprise a number of consensus sites for post-transcriptional regulation. Experimental observations indicate that the MG29 UTR sequence is, in fact, necessary for the post-transcriptional regulation of MG29 gene expression, revealing the UTR to be a target of the regulatory pathway in muscle that controls the expression of MG29. Accordingly, modulation of the post-transcriptional regulation of MG29 mRNA exists as another means of therapeutic intervention for diagnosing, treating and preventing muscle related pathologies.

Also described is a functional role of MG29 in calcium sparks. The elementary units of Ca release from SR in striated muscle cells are discreet, localized events known as Ca sparks. Ca sparks were first discovered in cardiac muscle as localized quantal Ca release events that originated from paracrystalline arrays of RyR channels on the SR surface, and therefore represent the elemental units of Ca-induced Ca release (CICR). The discovery of Ca sparks revolutionized our understanding of the physiology and pathophysiology of Ca signaling in cardiac and smooth muscles. Ever since the discovery of Ca sparks in cardiac muscle, investigators have had difficulty in detecting these localized Ca release events in intact adult mammalian skeletal muscle. Ca sparks were also soon detected in neonatal mammalian skeletal muscle where they were attributed to the activity of the type 3 RyR, an isoform highly expressed in skeletal muscle during fetal development. While rare observations of Ca sparks have been made in resting intact mammalian fibers, until recently, significant numbers of events were only observed in skeletal fibers whose sarcolemmal integrity was disrupted by various physical or chemical skinning methods. Because of these intrinsic difficulties with monitoring Ca spark signaling activity in intact mammalian muscle fibers, the cellular and molecular mechanisms underlying the regulation of Ca spark signaling in, and what information on the functional state of skeletal muscle can be determined using Ca sparks, remains largely unknown.

In certain aspects, the invention relates to isolated and recombinant nucleic acids encoding MG29 proteins or bioactive portions thereof, for example, a truncated portion encoding only the synaptophysin domain, or the MARVEL domain. As such, any embodiment of this aspect, the nucleic acids encoding MG29 proteins encompass deletions, substitutions, truncations, fusion proteins and the like. In an additional embodiment, the invention encompasses recombinant polypeptides comprising a first polypeptide domain having at least 30% homology to a human MG29 synaptophysin domain polypeptide ("synaptophysin-like domain"), and optionally a second polypeptide domain having at least 30% homology to a human MG29 MARVEL domain polypeptide ("MARVEL-like domain). In certain additional embodiments, the invention encompasses recombinant polypeptides in which the synaptophysin or synaptophysin-like domain is juxtaposed with a MARVEL domain or MARVEL-like domain. Recombinant polypeptides of the invention may also comprise a fusion protein domain, and/or an amino acid linking sequences inserted between polypeptide domains, which allows, for example, for steric flexibility and/or comprises consensus sequence for enzymatic modification (e.g., phosphorylation, protease cleavage, ubiquination, or the like). The recombinant polypeptides can be constructed using standard molecular biological techniques for manipulation of DNA sequences; some of which are described in greater detail below.

For example, in certain aspects, the invention encompasses an isolated or recombinant nucleic acid encoding polypeptides formed by expressing genes or cDNA constructs formed by combining nucleotides encoding amino acid or peptide components from other members of the MG29 family, for example, those specified in TABLES 1 and 2. The nucleic acids encoding the respective amino acid or peptide domains can be cloned from any desired parental gene and combined into a single contiguous nucleic acid using standard molecular biological techniques. Also, because it is generally recognized that evolutionarily conserved amino acid sequences will function similarly, it is within the abilities of those skilled in the art to generate additional proteins in accordance with the instant teachings, and to assess the ability of the recombinant proteins to facilitate E-C coupling and muscle plasticity without undue experimentation. As such, recombinant proteins assembled from the domains of the MG29 family members, for example, those identified above, is expressly contemplated as being within the scope of the invention.

As used herein, "derivatives" are compositions formed from the native compounds either directly, by modification, or by partial substitution. As used herein, "analogs" are compositions that have a structure similar to, but not identical to, the native compound.

The term "about" as it is used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. For example, in accordance with the above, the phrase "about" is normally used to encompass values within the standard deviation or standard error.

As described above, in certain aspects the present invention relates to nucleic acids, and the polypeptides encoded from nucleic acids of the invention, which, alone or in combination with other components, can modulate muscle physiology, including E-C coupling. The invention also relates to compositions, for example, polypeptides, nucleic acids encoding cytoplasmic, nuclear, membrane bound, and secreted polypeptides; as well as vectors, antibodies, recombinant proteins, pseudopeptides, fusion proteins, chemical compounds, host cells, transgenic animals, and methods for producing the same.

Biopolymers

By "nucleotide" is meant a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Eckstein et al., International PCT Publication No. WO 92/07065; Usman et al., International PCT Publication No. WO 93/15187; Uhlman & Peyman, supra all are hereby incorporated by reference herein).

By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra).

As used herein, the term "nucleic acid" is intended to include DNA molecules (e.g., cDNA or genomic DNA), RNA molecules, analogs of DNA or RNA, including locked nucleic acids and peptide nucleic acids, and derivatives thereof.

By "down-regulate" it is meant that the expression of the gene, or level of RNAs or equivalent RNAs encoding one or more proteins, or activity of one or more proteins, such as MG29 or MG29 receptor polypeptide genes, is reduced below that observed in the absence of the nucleic acid molecules of the invention.

By "up-regulate" is meant that the expression of the gene, or level of RNAs or equivalent RNAs encoding one or more protein subunits, or activity of one or more protein subunits, such as MG29 or MG29 receptor, is greater than that observed in the absence of the nucleic acid molecules of the invention. For example, the expression of a gene, can be increased in order to treat, prevent, ameliorate, or modulate a pathological condition caused or exacerbated by an absence or low level of gene expression.

By "modulate" is meant that the expression of the gene, or level of RNAs or equivalent RNAs encoding one or more proteins, or activity of one or more proteins is up-regulated or down-regulated, such that the expression, level, or activity is greater than or less than that observed in the absence of the nucleic acid molecules of the invention.

By "gene" it is meant a nucleic acid that encodes RNA, for example, nucleic acid sequences including but not limited to a segment encoding a polypeptide.

"Complementarity" refers to the ability of a nucleic acid to form hydrogen bond(s) with another RNA sequence by either traditional Watson-Crick base pairing or other non-traditional types.

By "RNA" is meant a molecule comprising at least one ribonucleotide residue. By "ribonucleotide" or "2'-OH" is meant a nucleotide with a hydroxyl group at the 2' position of a D-ribo-furanose moiety.

By "homology" is meant the nucleotide sequence of two or more nucleic acid molecules is partially or completely identical. In certain embodiments the homolgous nucleic acid has 30%, 40%, 50%, 60%, 70%, 80%, 90%, or 95% homology to an MG29 nucleic acid, for example, at least one of SEQ ID NOs.: 20-26.

By "vectors" is meant any nucleic acid-based technique used to deliver a desired nucleic acid, for example, bacterial plasmid, viral nucleic acid, HAC, BAC, and the like.

The biopolymer compositions encompassed by the invention are collectively and interchangeably referred to herein as "MG29 nucleic acids", "MG29 receptor nucleic acids", "MG29 polynucleotides", or "MG29 receptor polynucleotides", respectively, and the corresponding encoded polypeptides are referred to as "MG29 polypeptides", MG29 receptor polypeptides", "MG29 proteins", or "MG29 receptor proteins", respectively. Unless expressly indicated otherwise, it is contemplated that these terms are to be construed broadly to include bioactive portions, fragments, deletions or substitutions, truncations, gene fusions at the amino or carboxy terminal or both, and combinations thereof. Also, unless indicated otherwise, "MG29" and "MG29 receptor" are used generally to refer to any related and/or derived biopolymers as explicitly, implicitly, or inherently described herein. As used herein, the term "MG29 receptor" or the like, encompasses proteins that bind to the MG29 polypeptide and/or the MG29 mRNA or gene. As used herein, the terms "nucleic acid" or "gene" may also encompass the 5' UTR, 3' UTR, promoter sequences, enhancer sequences, intronic and exonic DNA of the gene as well as the mRNA or cDNA sequence.

In another embodiment, the invention encompasses an isolated or recombinant nucleic acid encoding an MG29 polypeptide as described above, or as set forth in SEQ ID NOs.: 1-19, and/or a homolog, or fragment thereof, wherein the polypeptide facilitates muscle function.

In additional aspects, the invention relates to methods of administering to an individual an effective amount of a nucleic acid encoding an MG29 and/or MG29 receptor polypeptide, for example, MG29 and/or an MG29 homolog, fragment, and derivative thereof, for the treatment and/or prevention of a muscle related pathology or condition in vitro, in vivo or ex vivo. As demonstrated herein, the MG29 polypeptides of the invention are capable of regulating a variety of processes in muscle and muscle cells, and can provide an effective therapeutic approach against a number of disorders that involve compromised muscle function. In certain embodiments, the cell comprises, for example, a skeletal muscle or cardiac muscle cell.

In an additional aspect, the invention relates to methods of treating and/or preventing a muscle related disease or pathological condition comprising administering to an individual an effective amount of a composition comprising a nucleic acid encoding an MG29 and/or MG29 receptor polypeptide, homolog, fragment or derivative thereof, in combination with a pharmaceutically acceptable carrier, wherein the composition is effective in treating and/or preventing said muscle-related pathology or condition. In certain embodiments, the muscle-related pathology or condition includes fatigue, atrophy, cachexia, sarcopenia, muscular dystrophy, cardiac ischemia, heart failure, age-related fatigue or degeneration, COPD, wound healing, channelopathies, or any combination thereof.

In any of the methods described herein, the nucleic acids or polypeptides of the invention may be delivered or administered in any pharmaceutically acceptable form, and in any pharmaceutically acceptable route as described in further detail below. For example, compositions comprising nucleic acids and/or polypeptides of the invention can be delivered systemically or administered directly to a cell or tissue for the treatment and/or prevention of cell membrane damage. In certain additional embodiments, the nucleic acids and/or polypeptides of the invention comprise a carrier moiety that improves bioavailability, increases the drug half-life, targets the therapeutic to a particular cell or tissue type or combination thereof.

In additional aspects, the invention comprises methods of modulating the protein expression, activity, or transcription of MG29 and/or an MG29 receptor. In certain embodiments, the method comprises administering a recombinant nucleic acid encoding an MG29 polypeptide or an MG29 receptor to a cell or tissue, in vitro, ex vivo, or in vivo. As discussed in detail below, the recombinant nucleic acid may be cistronic; i.e., comprise the desired coding sequence within a sing open reading frame (ORF); or it may contain one or more intronic sequences. In certain other embodiments, the method comprises administering a recombinant nucleic acid that is capable of hybridizing specifically to a nucleic acid that encodes an MG29 and/or MG29 receptor polypeptide, to a cell or tissue, in vitro, ex vivo, or in vivo. The recombinant nucleic acid may also be incorporated into a vector nucleic acid, for example, a plasmid, viral vector, artificial chromosome or the like. In additional embodiments, a vector comprising a recombinant MG29 or MG29 receptor encoding nucleic acid is contemplated. The nucleic acids of the invention may also contain one or more transcription or replication regulatory elements, selectable markers or translation modifying sequences operably linked to the coding nucleic acid.

In an aspect, the invention provides an isolated nucleic acid encoding an MG29 polypeptide having at least 30%, 40%, 50%, 60%, 70%, 80%, 90% or 100% identity to any of the nucleic acids disclosed in SEQ ID NOS: 20-26. In certain embodiments, the isolated nucleic acid molecules of the invention will hybridize under stringent conditions to a nucleic acid sequence complementary to a nucleic acid molecule that includes a protein-coding sequence of a MG29 nucleic acid sequence. The invention also includes an isolated nucleic acid that encodes an MG29 polypeptide, or a fragment, homolog, analog, fusion protein, pseudopeptide, peptidomimetic or derivative thereof. For example, the nucleic acid can encode a polypeptide at least 30%, 40%, 50%, 60%, 70%, 80%, 90% or 100% identity to a polypeptide comprising the amino acid sequences of SEQ ID NOS: 1-19. The nucleic acid can be, for example, a genomic DNA fragment or a cDNA molecule that includes the nucleic acid sequence of any of SEQ ID NOS: 20-26.

In another aspect, the invention includes a method of detecting the presence of an MG29 or MG29 receptor nucleic acid or polypeptide in a sample. In the method, a sample is contacted with a detectable agent (e.g., nucleic acid probe, an antibody or small molecule) that selectively binds to the target nucleic acid or polypeptide, respectively, under conditions allowing for formation of a complex between the agent and the nucleic acid or polypeptide. The complex is then detected, if present, thereby identifying the MG29 or MG29 receptor nucleic acid or polypeptide, within the sample. The methods of invention can also be used to identify specific cell or tissue types based on their expression of an MG29 or MG29 receptor nucleic acid or polypeptide.

In certain other embodiments the invention includes nucleic acids encoding fusion proteins comprising a "tag" or indicator portion and an MG29 or MG29 receptor portion, as well as the cognate fusion proteins. In certain aspects the tag or indicator portion can be a peptide adapted for purification purposes, for example, FLAG tag, 6×His tag, Maltose-Binding Protein (MBP) tag, or the like. In other aspects, the tag peptide comprises a peptide adapted for providing a signal such as an antibody epitope or a fluorescent peptide. Still other aspects include the fusion of the MG29 or MG29 receptor with a peptide that is adapted for mediating subcellular localization or translocation across a cellular membrane, for example, a TAT fusion protein from the HIV virus To facilitate cell penetration or a modified cellular localization tag to couple MG29 or MG29 receptor to particular cellular organelles.

In addition, the invention relates to nucleic acids, including interfering nucleic acids targeting MG29 or MG29 receptor nucleic acids. For example, the present invention features a nucleic acid molecule, such as a decoy RNA, dsRNA, siRNA, shRNA, microRNA, aptamer, and/or antisense nucleic acid molecules, which down regulates expression of a sequence encoding an MG29 or MG29 receptor proteins. In another embodiment, a nucleic acid molecule of the invention has an endonuclease activity or is a component of a nuclease complex, and cleaves RNA having an MG29 or MG29 receptor nucleic acid sequence. In any of the interfering nucleic acid embodiments, the nucleic acid molecule comprises between 12 and 100 bases complementary to an RNA having an MG29 or MG29 receptor nucleic acid sequence. In another embodiment, the nucleic acid molecule comprises between 14 and 24 bases complementary to an RNA having an MG29 or MG29 receptor nucleic acid sequence. In any embodiment described herein, the nucleic acid molecule can be synthesized chemically according to methods well known in the art. A number of references describe useful methods and approaches for generating RNAs including: 6900187, 6383808, 7101991, 7285541, 7368436, 7022828; which are incorporated herein by reference.

By "antisense nucleic acid", it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop or hairpin, and/or an antisense molecule can bind such that the antisense molecule forms a loop or hairpin. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol, 40, 1-49, which are incorporated herein by reference in their entirety. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

Long double-stranded RNAs (dsRNAs; typically >200 nt) can be used to silence the expression of target genes in a variety of organisms and cell types (e.g., worms, fruit flies, and plants). Upon introduction, the long dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effector step). Cleavage of cognate RNA takes place near the middle of the region bound by the siRNA strand. In mammalian cells, introduction of long dsRNA (>30 nt) initiates a potent antiviral response, exemplified by nonspecific inhibition of protein synthesis and RNA degradation. The mammalian antiviral response can be bypassed, however, by the introduction or expression of siRNAs.

Injection and transfection of dsRNA into cells and organisms has been the main method of delivery of siRNA. And while the silencing effect lasts for several days and does appear to be transferred to daughter cells, it does eventually diminish. Recently, however, a number of groups have developed expression vectors to continually express siRNAs in transiently and stably transfected mammalian cells. (See, e.g., Brummelkamp T R, Bernards R, and Agami R. (2002). A system for stable expression of short interfering RNAs in mammalian cells. Science 296:550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. Nature Biotechnol. 20:505-508; Sui G, Soohoo C, Affar E-B, Gay F, Shi Y, Forrester W C, and Shi Y. (2002). A DNA vector-based RNAi technology to suppress gene expression in mammalian cells. Proc. Natl. Acad. Sci. USA 99(6):5515-5520; Yu J-Y, DeRuiter SL, and Turner D L. (2002). RNA interference by expression of short-interfering RNAs and hairpin RNAs in mammalian cells. Proc. Natl. Acad. Sci. USA 99(9):6047-6052, which are herein incorporated by reference in their entirety).

By "double stranded RNA" or "dsRNA" is meant a double stranded RNA that matches a predetermined gene sequence that is capable of activating cellular enzymes that degrade the corresponding messenger RNA transcripts of the gene. These dsRNAs are referred to as short intervening RNA (siRNA) and can be used to inhibit gene expression (see for example Elbashir et al., 2001, Nature, 411, 494-498; and Bass, 2001, Nature, 411, 428-429). The term "double stranded RNA" or "dsRNA" as used herein refers to a double stranded RNA molecule capable of RNA interference "RNAi", including short interfering RNA "siRNA" see for example Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914.

Oligonucleotides (eg; antisense, GeneBlocs) are synthesized using protocols known in the art as described in Caruthers et al., 1992, Methods in Enzymology 211, 3 19, Thompson et al., International PCT Publication No. WO 99/54459, Wincott et al., 1995, Nucleic Acids Res. 23, 2677 2684, Wincott et al., 1997, Methods Mol. Bio., 74, 59, Brennan et al, 1998, Biotechnol Bioeng., 61, 33 45, and Brennan, U.S. Pat. No. 6,001,311. All of these references are incorporated herein by reference. In a non-limiting example, small scale syntheses are conducted on a 394 Applied Biosystems, Inc. synthesizer. Alternatively, the nucleic acid molecules of the present invention can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

In one embodiment the invention relates to a method for treating or preventing a muscle related pathology or condition by up-regulating the expression, transcription and/or activity of a gene encoding an MG29 or MG29 receptor polypeptide. In one embodiment, inhibition or down-regulation with a nucleic acid molecule preferably is below that level observed in the presence of an inactive or attenuated molecule that is able to bind to the same site on the target RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of MG29 or MG29 receptor genes with the nucleic acid molecule of the instant invention is greater in the presence of the nucleic acid molecule than in its absence.

In certain aspects, the invention relates to diagnostic oligonucleotides and diagnostic oligonucleotide set(s), for which a correlation exists between the health status of an individual, and the individual's expression of RNA or protein products corresponding to the nucleotide sequence. In some instances, only one oligonucleotide is necessary for such detection. Members of a diagnostic oligonucleotide set may be identified by any means capable of detecting expression or a polymorphism of RNA or protein products, including but not limited to differential expression screening, PCR, RT-PCR, SAGE analysis, high-throughput sequencing, microarrays, liquid or other arrays, protein-based methods (e.g., western blotting, proteomics, mass-spectrometry, and other methods described herein), and data mining methods, as further described herein.

In the context of the invention, nucleic acids and/or proteins are manipulated according to well known molecular biology techniques. Detailed protocols for numerous such procedures are described in, e.g., in Ausubel et al. Current Protocols in Molecular Biology (supplemented through 2000) John Wiley & Sons, New York ("Ausubel"); Sambrook et al. Molecular Cloning—A Laboratory Manual (2nd Ed.), Vol. 1-3, Cold Spring Harbor Laboratory, Cold Spring Harbor, N.Y., 1989 ("Sambrook"), and Berger and Kimmel Guide to Molecular Cloning Techniques, Methods in Enzymology volume 152 Academic Press, Inc., San Diego, Calif. ("Berger").

The description below of the various aspects and embodiments is provided with reference to the exemplary nucleic acids of the invention. However, the various aspects and embodiments are also directed to genes which encode homologs, orthologs, and paralogs of other MG29 or MG29 receptor proteins, and genes, and includes all isoforms, splice variants, and polymorphisms. Those additional genes can be analyzed for target sites using the methods described for MG29 or MG29 receptor nucleic acids or genes. Thus, the inhibition and the effects of such inhibition of the other genes can be performed as described herein.

Certain aspects of the invention encompass methods of detecting gene expression or polymorphisms with one or more DNA molecules wherein the one or more DNA molecules has a nucleotide sequence which detects expression of a gene corresponding to the oligonucleotides depicted in the Sequence Listing (See TABLES 1 and 2). In one format, the oligonucleotide detects expression of a gene that is differentially expressed. The gene expression system may be a candidate library, a diagnostic agent, a diagnostic oligonucleotide set or a diagnostic probe set. The DNA molecules may be genomic DNA, RNA, protein nucleic acid (PNA), cDNA or synthetic oligonucleotides. Following the procedures taught herein, one can identify sequences of interest for analyzing gene expression or polymorphisms. Such sequences may be predictive of a disease state. Polymorphisms have been identified that correlate with disease severity. (See, Zhong et al., Simultaneous detection of microsatellite repeats and SNPs in the macrophage migration inhibitory factor gene by thin-film biosensor chips and application to rural field studies. *Nucleic Acids Res.* 2005 Aug. 2; 33(13):e121; Donn et al., A functional promoter haplotype of macrophage migration inhibitory factor is linked and associated with juvenile idiopathic arthritis. *Arthritis Rheum.* 2004 May; 50(5):1604-10; all of which are incorporated herein by reference in their entirety for all purposes.). As one of ordinary skill will comprehend, the MG29 gene polymorphisms associated with muscle disorders, and hence useful as diagnostic markers according to the methods of the invention, may appear in any of the nucleic acid regions of the MG29 gene or regulatory regions. Techniques for the identification and monitoring of polymorphisms are known in the art and are discussed in detail in U.S. Pat. No. 6,905,827 to Wohlgemuth, which is incorporated herein by reference in its entirety for all purposes.

The nucleic acid molecules of the instant invention, individually, or in combination or in conjunction with other drugs, can be used to treat diseases or conditions discussed above. For example, the subject can be treated, or other appropriate cells can be treated, as is evident to those skilled in the art, individually or in combination with one or more drugs under conditions suitable for the treatment.

In another aspect, the invention includes pharmaceutical compositions that include therapeutically- or prophylactically-effective amounts of a therapeutic and a pharmaceutically-acceptable carrier. The therapeutic can be a nucleic acid, e.g., a MG29 or MG29 receptor nucleic acid, for example, a peptide nucleic acid, a cDNA, or RNA, such as for example, a small inhibitory RNA; a polypeptide comprising a portion of MG29 or MG29 receptor; or an antibody specific for a MG29 or MG29 receptor polypeptide. In a further aspect, the invention includes, in one or more containers, a therapeutically- or prophylactically-effective amount of this pharmaceutical composition. Also included in the invention is an oligonucleotide, e.g., an oligonucleotide which includes at least 6 contiguous nucleotides of an MG29 or MG29 receptor nucleic acid or a complement of said oligonucleotide.

The nucleic acid molecules of the present invention can be modified extensively to enhance stability by modification with nuclease resistant groups, for example, 2'-amino, 2'-C-allyl, 2'-fluoro, 2'-O-methyl, 2'-H (for a review see Usman and Cedergren, 1992, TIBS 17, 34; Usman et al., 1994, Nucleic Acids Symp. Ser. 31, 163).

While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized. The reduction in the concentration of these linkages should lower toxicity resulting in increased efficacy and higher specificity of these molecules.

Nucleic acid molecules having chemical modifications that maintain or enhance activity are provided. Such nucleic acid is also generally more resistant to nucleases than unmodified nucleic acid. Nucleic acid molecules are preferably resistant to nucleases in order to function as effective intracellular therapeutic agents. Improvements in the chemical synthesis of RNA and DNA (Wincott et al., 1995 Nucleic Acids Res. 23, 2677; Caruthers et al., 1992, Methods in Enzymology 211, 3-19 (incorporated by reference herein) have expanded the ability to modify nucleic acid molecules by introducing nucleotide modifications to enhance their nuclease stability as described above. The use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules and/or other chemical or biological molecules). The treatment of subjects with nucleic acid molecules can also include combinations of different types of nucleic acid molecules.

In one embodiment, the invention features modified nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, Nucleic Acid Analogues: Synthesis and Properties, in Modern Synthetic Methods, VCH, 331 417, and Mesmaeker et al., 1994, Novel Backbone Replacements for Oligonucleotides, in Carbohydrate Modifications in Antisense Research, ACS, 24 39. These references are hereby incorporated by reference herein. Various modifications to nucleic acid (e.g., antisense and ribozyme) structure can be made to enhance the utility of these molecules. For example, such modifications can enhance shelf-life, half-life in vitro, bioavailability, stability, and ease of introduction of such oligonucleotides to the target site, including e.g., enhancing penetration of cellular membranes and conferring the ability to recognize and bind to targeted cells.

Administration of Nucleic Acid Molecules. Methods for the delivery of nucleic acid molecules are described in Akhtar et al., 1992, Trends Cell Bio., 2, 139; and Delivery Strategies for Antisense Oligonucleotide Therapeutics, ed. Akhtar, 1995 which are both incorporated herein by reference. Sullivan et al., PCT WO 94/02595, further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by a incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. For a comprehensive review on drug delivery strategies including CNS delivery, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400.

The molecules of the instant invention can be used as pharmaceutical agents. Pharmaceutical agents prevent, inhibit the occurrence, or treat (alleviate a symptom to some extent, preferably all of the symptoms) a disease state in a subject. A number of useful nucleic acid-based therapeutic approaches are known and discussed in Patil et al., *AAPS Journal*, 2005; 7(1):E61-77, which is incorporated by reference in its entirety.

The negatively charged polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

Nucleic acid molecules of the invention can also be administered in the form of suppositories, e.g., for rectal administration of the drug or via a catheter directly to the bladder itself. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols. Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle. The amount of active ingredient that can be combined with the carrier materials to produce a single dosage form varies depending upon the host treated and the particular mode of administration. Dosage unit forms generally contain between from about 1 mg to about 5000 mg of an active ingredient. It is understood that the specific dose level for any particular patient or subject depends upon a variety of factors including the activity of the specific compound employed, the age, body weight, general health, sex, diet, time of administration, route of administration, and rate of excretion, drug combination and the severity of the particular disease undergoing therapy.

Alternatively, certain of the nucleic acid molecules of the instant invention can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591 5; Kashani-Sabet et al., 1992, Antisense Res. Dev., 2, 3 15; propulic et al., 1992, J. Virol., 66, 1432 41; Weerasinghe et al., 1991, J. Virol., 65, 5531 4; Ojwang et al., 1992, Proc. Natl. Acad. Sci. USA, 89, 10802 6; Chen et al., 1992, Nucleic Acids Res., 20, 4581 9; Sarver et al., 1990 Science, 247, 1222 1225; Thompson et al, 1995, Nucleic Acids Res., 23, 2259; Good et al., 1997, Gene Therapy, 4, 45; all of these references are hereby incorporated in their totalities by reference herein). Those skilled in the art realize that any nucleic acid can be expressed in eukaryotic cells from the appropriate DNA/RNA vector.

In one aspect the invention features an expression vector comprising a nucleic acid sequence encoding at least one of the nucleic acid molecules of the instant invention. The nucleic acid sequence encoding the nucleic acid molecule of the instant invention is operably linked in a manner which allows expression of that nucleic acid molecule.

Transcription of the nucleic acid molecule sequences are driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743 7; Gao and Huang 1993, Nucleic Acids Res., 21, 2867 72; Lieber et al., 1993, Methods Enzymol., 217, 47 66; Zhou et al., 1990, Mol. Cell. Biol., 10, 4529 37). All of these references are incorporated by reference herein. Several investigators have demonstrated that nucleic acid molecules, such as ribozymes expressed from such promoters can function in mammalian cells (e.g. Kashani-Sabet et al., 1992, Antisense Res. Dev., 2, 3 15; Ojwang et al., 1992, Proc. Natl. Acad. Sci. USA, 89, 10802 6; Chen et al, 1992, Nucleic Acids Res., 20, 4581 9; Yu et al., 1993, Proc. Natl. Acad. Sci. USA, 90, 6340 4; L'Huillier et al., 1992, EMBO J., 11, 4411 8; Lisziewicz et al., 1993, Proc. Natl. Acad. Sci. U.S.A., 90, 8000 4; Thompson et al., 1995, Nucleic Acids Res., 23, 2259; Sullenger & Cech, 1993, Science, 262, 1566).

In another aspect the invention features an expression vector comprising nucleic acid sequence encoding at least one of the nucleic acid molecules of the invention, in a manner which allows expression of that nucleic acid molecule. The expression vector comprises in one embodiment; a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule.

In another embodiment, an isolated nucleic acid molecule of the invention comprises a nucleic acid molecule that is a complement of the nucleotide sequence of an MG29 nucleic acid. As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect.

As used herein, "fragments" are defined as sequences of at least 6 (contiguous) nucleic acids or at least 4 (contiguous) amino acids, a length sufficient to allow for specific hybridization in the case of nucleic acids or for specific recognition of an epitope in the case of amino acids, and are at most some portion less than a full length sequence.

Derivatives or analogs of the nucleic acids or proteins of the invention include, but are not limited to, molecules comprising regions that are substantially homologous to the nucleic acids or proteins of the invention, in various embodiments, by at least about 30%, 40%, 50%, 60%, 70%, 80%, 90%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993. Nucleic acid derivatives and modifications include those obtained by gene replacement, site-specific mutation, deletion, insertion, recombination, repair, shuffling, endonuclease digestion, PCR, subcloning, and related techniques.

"Homologs" can be naturally occurring, or created by artificial synthesis of one or more nucleic acids having related sequences, or by modification of one or more nucleic acid to produce related nucleic acids. Nucleic acids are homologous when they are derived, naturally or artificially, from a common ancestor sequence (e.g., orthologs or paralogs). If the homology between two nucleic acids is not expressly described, homology can be inferred by a nucleic acid comparison between two or more sequences. If the sequences demonstrate some degree of sequence similarity, for example, greater than about 30%, 40%, 50%, 60%, 70%, 80%, or 90% at the primary amino acid structure level, it is concluded that they share a common ancestor. For purposes of the present invention, genes are homologous if the nucleic acid sequences are sufficiently similar to allow recombination and/or hybridization under low stringency conditions.

As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA.

Furthermore, one of ordinary skill will recognize that "conservative mutations" also include the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

Descriptions of the molecular biological techniques useful to the practice of the invention including mutagenesis, PCR, cloning, and the like include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989, and CURRENT PROTOCOLS IN MOLECULAR BIOLOGY, F. M. Ausubel et al., eds., Current Protocols, a joint venture between Greene Publishing Associates, Inc. and John Wiley & Sons, Inc.; Berger, Sambrook, and Ausubel, as well as Mullis et al., U.S. Pat. No. 4,683,202 (1987); PCR PROTOCOLS A GUIDE TO METHODS AND APPLICATIONS (Innis et al. eds), Academic Press, Inc., San Diego, Calif. (1990) (Innis); Arnheim & Levinson (Oct. 1, 1990) C&EN 36-47.

In yet another embodiment, a nucleic acid of the invention is expressed in mammalian cells using a mammalian expression vector. For suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

A polynucleotide can be a DNA molecule, a cDNA molecule, genomic DNA molecule, or an RNA molecule. A polynucleotide as DNA or RNA can include a sequence wherein T (thymidine) can also be U (uracil). If a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

In any of the embodiments, the nucleic acids encoding an MG29 or MG29 receptor can be present as: one or more naked DNAs; one or more nucleic acids disposed in an appropriate expression vector and maintained episomally; one or more nucleic acids incorporated into the host cell's genome; a modified version of an endogenous gene encoding the components of the complex; one or more nucleic acids in combination with one or more regulatory nucleic acid sequences; or combinations thereof. The nucleic acid may optionally comprise a linker peptide or fusion protein component, for example, His-Tag, FLAG-Tag, Maltose Binding Protein (MBP)-Tag, fluorescent protein, GST, TAT, an antibody portion, a signal peptide, and the like, at the 5' end, the 3' end, or at any location within the ORF.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

Any of the embodiments described herein, can be achieved using standard molecular biological and genetic approaches well known to those of ordinary skill in the art.

In a further aspect, the invention includes methods of producing a polypeptide by expressing, in a cell, an endogenous or exogenous MG29 or MG29 receptor nucleic acid. If desired, the polypeptide can then be recovered. In still another aspect, the invention includes a method of producing a polypeptide by culturing a cell that contains an endogenous nucleic acid encoding an MG29 or MG29 receptor nucleic acid, disposed upstream or downstream of an exogenous regulatory element, for example, a promoter, enhancer or repressor sequence. In certain embodiments, the exogenous regulatory element is incorporated into a host cell's genome through homologous recombination, strand break or mismatch repair mechanisms which are widely known in the art.

In a further aspect, the invention provides a method for modulating the activity or expression of an MG29 or MG29 receptor polypeptide, by contacting a cell sample that includes the MG29 or MG29 receptor polypeptide with a compound that binds to the MG29 or MG29 receptor polypeptide, an MG29 or MG29 receptor RNA binding protein, and/or an MG29 or MG29 receptor protein interactor in an amount sufficient to modulate the activity of said polypeptide. The compound can be, e.g., a small molecule, such as a nucleic acid, peptide, polypeptide, peptidomimetic, carbohydrate, lipid or other organic (carbon containing) or inorganic molecule, as further described herein.

In certain additional aspects, the invention relates to a composition comprising an isolated or recombinant polypeptide of the invention in combination with a pharmaceutically acceptable carrier. Certain embodiments of this aspect comprise therapeutic compositions comprising polypeptides of the invention, for example, MG29, in combination with a pharmaceutically acceptable carrier, wherein the therapeutic composition is administered systemically, and wherein the systemically administered composition is effective as a treatment for diseases that involve skeletal muscle.

In an additional aspect, the invention relates to compositions comprising a polypeptide of the invention in combination with at least one other agent, which is capable of modulating muscle function. In certain embodiment, the agent acts synergistically, via direct or indirect interaction with the polypeptide of the invention, to facilitate muscle function or ameliorate a muscle-related or other pathology. In additional embodiments, therapeutics of the invention may comprise one or more biologically active ingredients such as, Analgesics, Antacids, Antianxiety Drugs, Antiarrhythmics, Antibacterials, Antibiotics, Anticoagulants and Thrombolytics, Anticonvulsants, Antidepressants, Antidiarrheals, Antiemetics, Antifungals, Antihistamines, Antihypertensives, Anti-Inflammatories, Antineoplastics, Antipsychotics, Antipyretics, Antivirals, Barbiturates, Beta-Blockers, Bronchodilators, Cold Cures, Corticosteroids, Cough Suppressants, Cytotoxics, Decongestants, Diuretics, Expectorants, Hormones, Hypoglycemics (Oral), Immunosuppressives, Laxatives, Muscle Relaxants, Sedatives, Sex Hormones, Sleeping Drugs, Tranquilizer, Vitamins or a combination thereof.

In yet another aspect, the invention can be used in a method to identify the cellular receptors and downstream effectors of the invention by any one of a number of techniques commonly employed in the art. These include but are not limited to the two-hybrid system, affinity purification, co-precipitation with antibodies or other specific-interacting molecules.

As used herein, the term "MG29 antagonist" or "MG29 receptor antagonist", and the like is used generally to refer to an agent capable of direct or indirect inhibition of MG29 expression, translation, and/or activity; or MG29 receptor expression, translation, and/or activity. As used herein, the term "MG29 agonist" or "MG29 receptor agonist" is used generally to refer to an agent capable of direct or indirectly increasing MG29 expression, translation, and/or activity; or MG29 receptor expression, translation, and/or activity.

In an additional aspect, the invention relates to an isolated or recombinant MG29 polypeptide or polypeptide complex. MG29 polypeptides have the ability to interact (e.g., bind non-covalently) and form complexes with itself as well as with a number other cellular proteins. In an embodiment of this aspect the invention comprises an isolated or recombinant MG29 polypeptide, homolog, fragment, or derivative thereof, in combination with at least one other polypeptide (e.g., an MG29 receptor), wherein the combination forms a protein complex, and wherein the complex is useful as a therapeutic for improving muscle function, a diagnostic marker for determining the physiological condition or function of muscle, and/or as a tool for screening for compounds that modulate muscle function via an agonist or antagonist interaction with the complex. The invention further comprises a method of treating or preventing a muscle-related pathology comprising administering to a cell an effective amount of an isolated or recombinant MG29 polypeptide in a protein complex with at least one other protein, wherein the complex is capable of improving muscle function. The polypeptides of the complex can be formed, for example, using a peptide synthesizer according to standard methods; or by expressing each polypeptide in a single cell; or separately in a cell or cell lysate system and then isolating and purifying the polypeptide.

Also included in the invention are substantially purified MG29 polypeptides having a sequence as set forth in SEQ ID NOs: 1-19 or a functional portion thereof. In certain embodiments, the MG29 polypeptides of the invention include an amino acid sequence that is substantially identical to the amino acid sequence of a human MG29 polypeptide (SEQ ID NO.:3).

The invention also features antibodies that immunoselectively-bind to MG29, polypeptides, fragments, homologs, analogs, pseudopeptides, peptidomimetics or derivatives thereof. As such, in other embodiments, the invention pertains to isolated nucleic acid molecules that encode MG29 polypeptide binding proteins, antibody polypeptides, or biologically active portions thereof.

The term "antibody" as used herein refers to immunoglobulin molecules and immunologically active portions of immunoglobulin (Ig) molecules, i.e., molecules that contain an antigen-binding site that specifically binds (immunoreacts with) an antigen, comprising at least one, and preferably two, heavy (H) chain variable regions (abbreviated herein as VH), and at least one and preferably two light (L) chain variable regions (abbreviated herein as VL). Such antibodies include, but are not limited to, polyclonal, monoclonal, chimeric, single chain, Fab, Fab' and F(ab')2 fragments, and an Fab expression library. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies can be prepared from the intact polypeptide or fragments containing peptides of interest as the immunizing agent. A preferred antigenic polypeptide fragment is 15-100 contiguous amino acids. In one embodiment, the peptide is located in a non-transmembrane domain of the polypeptide, e.g., in an extracellular or intracellular domain. An exemplary antibody or antibody fragment binds to an epitope that is accessible from the extracellular milieu and that alters the functionality of the protein. In certain embodiments, the present invention comprises antibodies that recognize and are specific for one or more epitopes of MG29, and/or MG29 receptor protein, variants, portions and/or combinations thereof. In alternative embodiments antibodies of the invention may target and interfere with the MG29/MG29 receptor interaction.

The preparation of monoclonal antibodies is well known in the art; see for example, Harlow et al., Antibodies: A Laboratory Manual, page 726 (Cold Spring Harbor Pub. 1988), U.S. Pat. Nos. 6,331,415 to Cabilly; 6,407,213 and 6,639,055 to Carter; 6,562,622; 6,693,176; 6,881,557; 5,807,715 to Morrison; 5,225,539 to Winter; 5,585,089, 5,693,761, 6,180, 370, and 7,022,500 to Queen; 20070202105 to Doyle, all of which are incorporated herein by reference. Monoclonal antibodies can be obtained by injecting mice or rabbits with a composition comprising an antigen, verifying the presence of antibody production by removing a serum sample, removing the spleen to obtain B lymphocytes, fusing the lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by techniques well known in the art.

In other embodiments, the antibody can be recombinantly produced, e.g., produced by phage display or by combinatorial methods. Phage display and combinatorial methods can be used to isolate recombinant antibodies that bind MG29 polypeptides or MG29 binding proteins or fragments thereof (as described in, e.g., Ladner et al. U.S. Pat. No. 5,223,409; Fuchs et al. (1991) Bio/Technology 9:1370-1372; Hay et al. (1992) Hum Antibod Hybridomas 3:81-85; Huse et al. (1989) Science 246:1275-1281; Clackson et al. (1991) Nature 352: 624-628; Gram et al. (1992) PNAS 89:3576-3580. Human monoclonal antibodies can also be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855). A therapeutically useful antibody to the components of the complex of the invention or the complex itself may be derived from a "humanized" or "superhumanized" monoclonal antibody. Humanized monoclonal antibodies are produced by transferring mouse complementarity determining regions (CDRs) from heavy and light variable chains of the mouse immunoglobulin into a human variable domain, then substituting human residues into the framework regions of the murine counterparts.

The use of antibody components derived from humanized monoclonal antibodies obviates potential problems associated with immunogenicity of murine constant regions. Techniques for producing humanized monoclonal antibodies can be found in Jones et al., Nature 321: 522, 1986 and Singer et al., J. Immunol. 150: 2844, 1993; Wu T. T. and Kabat, E. A. (1970) J. Exp. Med., 132: 211-250; and Johnson G., Wu, T. T. and Kabat, E. A. (1995) In Paul, S. (ed.), Antibody Engineering Protocols. Humana Press, pp. 1-15, which are incorporated herein by reference. The antibodies can also be derived from human antibody fragments isolated from a combinatorial immunoglobulin library; see, for example, Barbas et al., Methods: A Companion to Methods in Enzymology 2, 119, 1991. In addition, chimeric antibodies can be obtained by splicing the genes from a mouse antibody molecule with appropriate antigen specificity together with genes from a human antibody molecule of appropriate biological specificity; see, for example, Takeda et al., Nature 314: 544-546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies. Single chain antibodies are formed by linking the heavy and light chain fragments of the Fv region via an amino acid bridge, resulting in a single chain polypeptide. Antibody fragments that recognize specific epitopes, e.g., extracellular epitopes, can be generated by techniques well known in the art. Such fragments include Fab fragments produced by proteolytic digestion, and Fab fragments generated by reducing disulfide bridges. When used for immunotherapy, the monoclonal antibodies, fragments thereof, or both may be unlabelled or labeled with a therapeutic agent. These agents can be coupled directly or indirectly to the monoclonal antibody by techniques well known in the art, and include such agents as drugs, radioisotopes, lectins and toxins.

The dosage ranges for the administration of monoclonal antibodies are large enough to produce the desired effect, and will vary with age, condition, weight, sex, age and the extent of the condition to be treated, and can readily be determined by one skilled in the art. Dosages can be about 0.1 mg/kg to about 2000 mg/kg. The monoclonal antibodies can be administered intravenously, intraperitoneally, intramuscularly, and/or subcutaneously.

In certain embodiments of the invention, at least one epitope encompassed by the antigenic peptide is a region of an MG29 polypeptide or MG29 binding protein that is located on the surface of the protein, e.g., a hydrophilic region. A hydrophobicity analysis of the protein sequence will indicate which regions of a polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824-3828; Kyte and Doolittle 1982, J. Mol. Biol. 157: 105-142, each incorporated herein by reference in their entirety. Antibodies that are specific for one or more domains within an antigenic protein, or derivatives, fragments, analogs or homologs thereof, are also provided herein. A protein of the invention, or a derivative, fragment, analog, homolog or ortholog thereof, may be utilized as an immunogen in the generation of antibodies that immunospecifically bind these protein components.

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, J. Mol. Biol. 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology, 10:779-783 (1992)); Lonberg et al. (Nature, 368: 856-859 (1994)); Morrison (Nature, 368:812-13 (1994)); Fishwild et al, (Nature Biotechnology, 14:845-51 (1996)); Neuberger (Nature Biotechnology, 14:826 (1996)); and Lonberg and Huszar (Intern. Rev. Immunol., 13:65-93 (1995)).

Human antibodies may additionally be produced using transgenic nonhuman animals which are modified so as to produce fully human antibodies rather than the animal's endogenous antibodies in response to challenge by an antigen. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 500 mg/kg body weight. Common dosing frequencies may range, for example, from twice daily to once a week.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

ELISA Assay

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., Fab or F(ab)2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques intracavity, or transdermally, alone or with effector cells.

Host Cells

As used in herein "cell" is used in its usual biological sense, and does not refer to an entire multicellular organism. The cell can, for example, be in vivo, in vitro or ex vivo e.g., in cell culture, or present in a multicellular organism, including, e.g., birds, plants and mammals such as primates, humans, cows, sheep, apes, monkeys, swine, dogs, mice, rats, and cats. The cell can be prokaryotic (e.g., bacterial cell) or eukaryotic (e.g., mammalian or plant cell). The term "host cell" includes a cell that might be used to carry a heterologous or exogenous nucleic acid, or expresses a peptide or protein encoded by a heterologous or exogenous (i.e., foreign) nucleic acid. A host cell can contain genes that are not found within the native (non-transformed) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the invention.

Transformation of a host cell with recombinant DNA may be carried out by conventional techniques as are well known to those skilled in the art. By "transformation" is meant a permanent or transient genetic change induced in a cell following introduction, modification, and/or extraction of nucleic acid material, for example, DNA or RNA.

Where the host is prokaryotic, such as $E.\ coli$, competent cells which are capable of DNA uptake can be prepared from cells harvested after exponential growth phase and subsequently treated by the $CaCl_2$ method by procedures well known in the art. Alternatively, $MgCl_2$, RbCl, liposome, or liposome-protein conjugate can be used. Transformation can also be performed after forming a protoplast of the host cell or by electroporation. These examples are not limiting on the present invention; numerous techniques exist for transfecting host cells that are well known by those of skill in the art and which are contemplated as being within the scope of the present invention.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. The eukaryotic cell may be a yeast cell (e.g., *Saccharomyces cerevisiae*) or may be a mammalian cell, including a human cell. For long-term, high-yield production of recombinant proteins, stable expression is preferred.

In another aspect, the invention encompasses a host cell comprising any MG29 and/or MG29 receptor nucleic acid of the invention. In certain embodiments, the host cell comprises a vector that contains a recombinant MG29 and/or a MG29 receptor nucleic acid; or a nucleic acid complementary to an MG29 or MG29 receptor encoding nucleic acid; or an exogenous or recombinant promoter modulating expression of endogenous MG29 or MG29 receptor gene.

In another aspect, the invention encompasses transgenic organisms, for example, a mouse, which contains at least one recombinant MG29 or MG29 receptor allele; or comprising an MG29 or MG29 receptor transgene; or comprising a vector containing a recombinant MG29 or MG29 receptor nucleic acid; or comprising an MG29 or MG29 receptor nucleic acid or nucleic acid precursor that is complementary to an MG29 or MG29 receptor encoding nucleic acid or portion thereof. In certain embodiments, the transgenic organism may comprise the recombinant MG29 or MG29 receptor nucleic acid operably linked to an inducible promoter/enhancer, and/or a tissue specific promoter, for example, a muscle specific promoter.

In yet another aspect, the invention includes a method for determining the presence of or predisposition to a disease associated with a muscle-related pathology or muscle dysfunction in a subject (e.g., a human subject). The method comprises detecting the genotype of an MG29 or MG29 receptor gene by treating a tissue sample from an individual with a detectable probe specific for an MG29 or MG29 receptor polymorphism or mutation, and detecting the formation of a probe/target complex, wherein formation of a complex is indicative of the presence of a particular genotype. Alternatively, measuring the amount of MG29 or MG29 receptor nucleic acid or polypeptide in a test sample from the subject and comparing the amount of the polypeptide in the test sample to the amount of MG29 or MG29 receptor nucleic acid or polypeptide present in a control sample. An alteration in the level in the test sample as compared to the control sample indicates the presence of or predisposition to a disease in the subject. Preferably, the predisposition includes, e.g., the diseases and disorders disclosed above and/or other pathologies and disorders of the like. Also, the expression levels of the new polypeptides of the invention can be used in a method to screen for various disorders as well as to determine the stage of particular disorders.

In another aspect, the invention relates to a method for diagnosing or monitoring disorder or disease or progression comprising detecting for the presence of a nucleotide polymorphism in an MG29 or MG29 receptor gene, associated with a disease, through the detection of the presence of an MG29 or MG29 receptor nucleic aid, protein or both; the transcription of an MG29 or MG29 receptor nucleic aid, protein or both; or expression level of an MG29 or MG29 receptor nucleic aid, protein or both.

In an embodiment, the invention comprises a method for screening for agents that modulate at least one of MG29 or MG29 receptor activity, protein levels, or gene expression comprising providing a cell or tissue; measuring for the amount of at least one of endogenous MG29 or MG29 receptor activity, protein level, or gene expression to establish a control value; contacting a test agent to the cell or tissue; measuring or detecting the activity of at least one of MG29 or MG29 receptor, amount of MG29 or MG29 receptor protein, or amount of MG29 or MG29 receptor gene expression to establish a test value; and comparing the control value to the test value, wherein an observed change between the test and control values indicates an agent capable of modulating at least one of MG29 or MG29 receptor activity, protein levels, or gene expression in the cell or tissue.

The invention further includes a method for screening for a modulator of disorders or syndromes including, e.g., the diseases and disorders disclosed above and/or other pathologies and disorders of the like. The method includes contacting a test compound with an MG29 or MG29 receptor nucleic acid or polypeptide, and determining if the test compound binds to said MG29 or MG29 receptor nucleic acid or polypeptide. Binding of the test compound to the MG29 or MG29 receptor nucleic acid or polypeptide indicates the test compound is a modulator of activity, transcription, translation or of latency or predisposition to the aforementioned disorders or syndromes.

In still additional aspects, the invention relates to methods of screening for compounds that modulate muscle function by contacting at least one of MG29 or MG29 receptor nucleic acid or polypeptide a combination thereof, with a test compound; and measuring the binding of the test compound, and/or the effects on muscle function (e.g., E-C coupling, Ca++ movement, contraction strength, fatigue, or the like).

Libraries of potential compounds are widely known and readily available that could be used in the methods of the invention. Furthermore, the techniques useful for measuring the binding of agents to MG29 or MG29 receptor polypeptides, the amount of MG29 or MG29 receptor protein, and/or the level of MG29 or MG29 receptor gene transcription and/or translation are described herein. Additional methods useful for practicing the invention are routinely used and can be adapted for use in the claimed methods using routine experimentation for the art.

Stem Cell Applications

In another aspect, the present invention encompasses therapeutic methods utilizing host cells, and stem cells modified according to the methods of the invention, which can be used in transplantation and/or adoptive cellular therapeutic approaches. In one embodiment of this aspect, a stem cell, for example, a muscle stem cell is isolated from a host, wherein the stem cell is capable of differentiating into a myocyte, and wherein the isolated stem cell is modified such that it demonstrates a modulated, for example, enhanced, MG29 or MG29 receptor activity, MG29 or MG29 receptor gene expression, or modulated MG29 or MG29 receptor signalling. In a preferred embodiment, the stem cell is contacted with an agent, for example, an MG29 or MG29 receptor polypeptide, MG29 or MG29 receptor nucleotide or agent that enhances the MG29 or MG29 receptor signalling cascade in muscle cells. The modified stem cell can then be cultured in vitro, and subsequently administered to an individual in need thereof.

A variety of methods are know for the isolation, culture and manipulation of stem cells capable of differentiation into skeletal muscle. See, for example, Stavropoulos M. E., et al. Curr Protoc Stem Cell Biol. 2009 June; Chapter 1: Unit 1F.8.; Shabbir A., et al. Transplantation. 2009 May 15; 87(9):1275-82; Lee A. S., et al. Stem Cells. 2009 May; 27(5):1098-108; Rudnicki M. A., Cold Spring Harb Symp Quant Biol. 2008; 73:323-31; Scime A., et al. Front Biosci. 2009 Jan. 1; 14:3012-23; Tanaka K. K., et al., Cell Stem Cell. 2009 Mar. 6; 4(3):217-25; Schabort E. J., et al., Stem Cells Dev. 2009 July-August; 18(6):813-30; Cerletti M., et al. Cold Spring Harb Symp Quant Biol. 2008; 73:317-22; Fan J., et al. Tissue Eng Part B Rev. 2009 March; 15(1):75-86; Collins C. A., et al. Methods Mol. Biol. 2009; 482:319-30; Quintero A. J., et al. Clin Sports Med. 2009 January; 28(1): 1-11; Okada M., et al. J Am Coll Cardiol. 2008 Dec. 2; 52(23):1869-80; Lagha M., et al. Cold Spring Harb Symp Quant Biol. 2008; 73:307-15; Luchessi A. D., et al. J Cell Physiol. 2009 March; 218(3):480-9.

Methods of Treatment

In certain additional aspects the invention relates to compositions and methods related to the treatment of muscle-related pathologies and conditions. In certain exemplary embodiments, the invention encompasses, for example, the administration of an effective amount of a therapeutic composition of the invention to an individual for the treatment and/or prevention of muscle-related pathologies and conditions; treatment and/or prevention of age-related muscle dysfunction; treatment and/or prevention of injury to any type of muscle tissue, such as those occurring in subjects suffering from cardiovascular diseases and/or sports-related injuries; the treatment and/or prevention of muscular dystrophy, sarcopenia, muscle fatigue, including age-related muscle fatigue and muscle fatigue due to exercise or exertion, muscle atrophy including age-related muscle degeneration and fatigue, cardiac ischemia, cachexia, heart failure, aging degeneration, COPD, or any combination thereof.

Also within the scope of the invention is the use of a therapeutic of the invention in the manufacture of a medicament for treating or preventing muscle-related pathologies or conditions, disorders or syndromes including, e.g., sarcopenia, muscle fatigue or atrophy, COPD, cardiovascular disease, cardiomyopathy, diabetes mellitus, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, hypercoagulation, hemophilia, ulcers, wounds, lesions, cuts, abrasions, oxidative damage, age-related tissue degeneration, surgically related lesions, burns, muscle weakness, muscle atrophy, connective tissue disorders, idiopathic thrombocytopenic purpura, heart failure, secondary pathologies caused by heart failure and hypertension, hypotension, angina pectoris, myocardial infarction, tuberous sclerosis, scleroderma, transplantation, autoimmune disease, lupus erythematosus, viral/bacterial/parasitic infections, multiple sclerosis, autoimmune disease, allergies, immunodeficiencies, graft versus host disease, asthma, emphysema, ARDS, inflammation and modulation of the immune response, viral pathogenesis, aging-related disorders, Th1 inflammatory diseases such as rheumatoid arthritis, multiple sclerosis, inflammatory bowel diseases, AIDS, wound repair, heart attacks, heart failure, muscular dystrophy, bed sores, diabetic ulcers, oxidative damage, and tissue damage such as sinusitis or mucositis, wrinkles, eczema or dermatitis, dry skin, obesity, endocrine disorders, anorexia, bulimia, renal artery stenosis, interstitial nephritis, glomerulonephritis, polycystic kidney disease, systemic, renal tubular acidosis, IgA nephropathy, nephrological diseases, hypercalcemia, Lesch-Nyhan syndrome, Von Hippel-Lindau (VHL) syndrome, trauma, regeneration (in vitro and in vivo), Hirschsprung's disease, Crohn's Disease, appendicitis, endometriosis, laryngitis, psoriasis, actinic keratosis, acne, hair growth/loss, alopecia, pigmentation disorders, myasthenia gravis, alpha-mannosidosis, beta-mannosidosis, other storage disorders, peroxisomal disorders such as zellweger syndrome, infantile refsum disease, rhizomelic chondrodysplasia (chondrodysplasia punctata, rhizomelic), and hyperpipecolic acidemia, osteoporosis, muscle disorders, urinary retention, Albright Hereditary Osteoeodystrophy, ulcers, Alzheimer's disease, stroke, Parkinson's disease, Huntington's disease, cerebral palsy, epilepsy, Lesch-Nyhan syndrome, multiple sclerosis, ataxia-telangiectasia, behavioral disorders, addiction, anxiety, pain, neuroprotection, Stroke, Aphakia, neurodegenerative disorders, neurologic disorders, developmental defects, conditions associated with the role of GRK2 in brain and in the regulation of chemokine receptors, encephalomyelitis, anxiety, schizophrenia, manic depression, delirium, dementia, severe mental retardation and dyskinesias, Gilles de la Tourette syndrome, leukodystrophies, cancers, breast cancer, CNS cancer, colon cancer, gastric cancer, lung cancer, melanoma, ovarian cancer, pancreatic cancer, kidney cancer, colon cancer, prostate cancer, neuroblastoma, and cervical cancer, Neoplasm; adenocarcinoma, lymphoma; uterus cancer, benign prostatic hypertrophy, fertility, control of growth and development/differentiation related functions such as but not limited maturation, lactation and puberty, reproductive malfunction, and/or other pathologies and disorders of the like.

In certain aspects, the modulation of muscle function, for example, MG29 or MG29 receptor activity is accomplished by, for example, the use of or modulation of MG29 or MG29 receptor nucleic acids or polypeptides, and/or MG29 or MG29 receptor nucleic acid or polypeptide binding partners, i.e., modulation of factors that bind to MG29 or MG29 receptor nucleic acids and/or MG29 or MG29 receptor polypeptides, and inhibit, attenuate or neutralize their biological activities, such as at least one MG29 RNA binding protein, for example, HuR, ARE, and/or LOX-DICE; and/or at least one MG29 gene transcription factor, for example, GATA, RUNX1, SREBP1, C/EBP, and/or p300; using inhibitory RNAs, antibodies, pseudopeptides, peptide analogs or peptidomimetics, or small molecules that bind and inhibit one or more target nucleic aids or polypeptides.

For example, the compositions of the present invention will have efficacy for treatment of patients suffering from the diseases and disorders disclosed above and/or other pathologies and disorders of the like. The polypeptides can be used as immunogens to produce antibodies specific for the invention, and as vaccines. They can also be used to screen for potential agonist and antagonist compounds. In addition, a cDNA encoding synaptophysin-like proteins of the invention, for example, MG29, may be useful in gene therapy when administered to a subject in need thereof. By way of non-limiting example, the compositions of the present invention will have efficacy for treatment of patients suffering from the diseases and disorders disclosed above and/or other pathologies and disorders of the like.

In a further aspect, the invention includes a method of treating or preventing a pathological condition associated with a disorder in a mammal by administering to the subject an MG29 or MG29 receptor polypeptide, nucleic acid encoding an MG29 or MG29 receptor polypeptide, or a polypeptide-specific antibody to a subject (e.g., a human subject), in an amount sufficient to alleviate or prevent the pathological condition. In preferred embodiments, the disorder, includes, e.g., the diseases and disorders disclosed above and/or other pathologies and disorders of the like.

Furthermore, due to the muscle-specific nature of the expression of the endogenous MG29 gene, the invention encompasses methods for the treatment and/or prevention of any type of muscle or vascular cell/tissue injury, for example, tissue injury that occurs as a result of cardiovascular disease, for example, myocardial infarction; or rigorous physical activity, for example, sports-related injuries, comprising administering an effective amount of the therapeutic of the invention to a subject in need thereof.

Kits

In another aspect the present invention provides a kit comprising a suitable container, a composition of the invention disposed therein, and instructions for its use. A further object of the present invention is to provide a kit comprising a suitable container, a therapeutic of the invention in a pharmaceutically acceptable form disposed therein, and instructions for its use. Also disclosed according to the present invention is a kit or system utilizing any one of the methods, selection strategies, materials, or components described herein. Exemplary kits according to the present disclosure will optionally, additionally include instructions for performing methods or assays, packaging materials, one or more containers which contain an assay, a device or system components, or the like.

Formulation

The therapeutic compositions of the invention comprise, in certain embodiments, for example, a nucleic acid encoding an MG29 or MG29 receptor polypeptide, an MG29 or MG29 receptor nucleic acid; a nucleic acid that binds a nucleic acid encoding an MG29 or MG29 receptor polypeptide; an MG29 or MG29 receptor encoding nucleic acid; an MG29 or MG29 receptor peptide analog, pseudopeptide or peptidomimetic based thereon; a small molecule modulator of MG29 or MG29 receptor or a MG29 or MG29 receptor protein-protein interaction; or a MG29-specific antibody or biologically-active derivatives or fragments thereof. As described herein, MG29 plays an important role in normal muscle function. Therefore, targeting the expression and/or activity of these nucleic acids, polypeptides, and homologs thereof will allow for a novel treatment of various acute and chronic diseases and conditions related to muscle dysfunction and degeneration.

In any aspect of the invention, the therapeutic composition of the invention can be in any pharmaceutically acceptable form and administered by any pharmaceutically acceptable route, for example, the therapeutic composition can be administered as an oral dosage, either single daily dose or unitary dosage form, for the treatment of a muscle damage due to a myocardial infarction, sclerotic lesion, or muscle tear due to sports-related activity to promote the regeneration and repair of the damaged muscle tissue. Such pharmaceutically acceptable carriers and excipients and methods of administration will be readily apparent to those of skill in the art, and include compositions and methods as described in the USP-NF 2008 (United States Pharmacopeia/National Formulary), which is incorporated herein by reference in its entirety.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The active compounds will generally be formulated for parenteral administration, e.g., formulated for injection via the intravenous, intraarthricular, intrathecal, intramuscular, sub-cutaneous, intra-lesional, or even intraperitoneal routes. The preparation of an aqueous composition that contains a cancer marker antibody, conjugate, inhibitor or other agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

A pharmacological composition or formulation refers to a composition or formulation in a form suitable for administration, e.g., systemic administration, into a cell or subject, preferably a human. By "systemic administration" is meant in vivo systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

Preparations for administration of the therapeutic of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

By pharmaceutically acceptable formulation is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly (DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies, including CNS delivery of nucleic acid molecules include material described in Boado et al., 1998, J. Pharm. Sci., 87, 1308-1315; Tyler et al, 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058. All these references are hereby incorporated herein by reference.

The invention also features the use of the composition comprising surface-modified liposomes containing poly (ethylene glycol) lipids (PEG-modified, or long-circulating liposomes or stealth liposomes). Nucleic acid molecules of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The compounds, nucleic acid molecules, polypeptides, and antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

An effective amount, pharmaceutically effective dose, therapeutically effective amount, or pharmaceutically effective amount is that dose required to prevent, inhibit the occurrence, or treat (alleviate a symptom to some extent, preferably all of the symptoms) of a disease state or pathological condition. The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the negatively charged polymer. In addition, effective amounts of the compositions of the invention encompass those amounts utilized in the examples to facilitate the intended or desired biological effect.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated in conventional manner.

Excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or acetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions suitable for injectable use include sterile aqueous solutions (where water soluble) or dispersions and sterile powders for the extemporaneous preparation of sterile injectable solutions or dispersion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. For intravenous administration, suitable carriers include physiological saline, bacteriostatic water, Cremophor™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For administration to non-human animals, the therapeutic compositions of the invention can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water. The composition can also be administered to a subject in combination with other therapeutic compounds to increase the overall therapeutic effect. The use of multiple compounds to treat an indication can increase the beneficial effects while reducing the presence of side effects.

ILLUSTRATIVE EXAMPLES

With Reference to the Drawings

Mitsugumin 29 (MG29)
Isolation of a Muscle Specific Synaptophysin-Related Protein The triad junction of skeletal muscle is comprised of a single invagination of the plasma membrane that plunges into the cytoplasm (the transverse-tubules or T-tubules) that is juxtaposed with two sections of the terminal cisternae of the sarcoplasmic reticulum (SR). Given the importance of the triad junction in induction of muscle contraction, it is not surprising that screening of this antibody library for novel proteins that localize to the triad junction by immunostaining has identified other proteins that regulate excitation-contraction (E-C) coupling and other aspects of Ca++handling in skeletal muscle. One of the most significant proteins identified during the screening of this library is mitsugumin29 (MG29), a novel member of the syanptophysin family of transmembrane proteins.

MG29 is nearly exclusively expressed in skeletal muscle fibers, although some minor levels of expression can be resolved in the kidney, and contains four transmembrane domains that allow the protein to localize at both the transverse (T-) tubular membrane and SR membranes of the triad junction. This subcellular distribution suggest MG29 may mediate communication between the T-tubular and junctional SR membrane. The protein structure of MG29 is homologous in amino acid sequence and shares characteristic structural features with the members of the synaptophysin family, a family of proteins essential for neurotransmitter release.

Synaptophysin: Synaptic Formation, Release and Biogenesis

Synaptophysin was originally identified as an abundant and highly immunogenic membrane protein of small synaptic vesicles that is also found in dense-core chromaffin and neurosecretory granules. Synaptophysin and its homologues, synaptoporin (or synaptophysin II) and pantophysin, share a common transmembrane organization, with four membrane-spanning regions and cytoplasmic amino and carboxy termini.

A unique feature of synaptophysin is that it have an oligomeric structure leading to the idea that synaptophysin may be a component of the fusion pore that forms during neurotransmitter release. Moreover, Alder et al. have shown that antisense oligonucleotides complementary to the synaptophysin 2+mRNA reduce $Ca^{2+}$ dependent glutamate secretion from *Xenopus* oocytes induced by injection of total brain mRNA. Microinjection of synaptophysin antibody into motor neurons blocked neuromuscular transmission. These data are consistent with synaptophysin being essential for neurotransmitter secretion. However, genetic approaches to identify the function of synaptophysin have not been successful; mutant mice lacking synaptophysin show a normal phenotype. This may reflect compensation by synaptoporin or other synaptophysin family members. Indeed, mice doubly deficient in synaptophysin and synaptogyrin display defects in synaptic plasticity.

Synaptophysin has been proposed to play a structural role in vesicle formation. Based on its high capacity to bind cholesterol, synaptophysin has been implicated in the generation of membrane curvature during synaptic vesicle biogenesis. Synaptophysin is also known to tightly interact with other proteins of the synaptic vesicle membrane, i.e. synaptobrevin and the vacuolar $H^+$ATPase. These interactions are thought to regulate exocytotic membrane fusion at the level of the SNARE complex or fusion pore formation. The latter idea is supported by studies on yeast vacuole fusion that implicate the vacuolar ATPase directly participate in membrane fusion.

The similarities between MG29 and synaptophysin suggest that MG29 may play an important role in modulation of membrane structures in skeletal muscle. Skeletal muscles are among the most plastic tissue in nature, and normal muscle physiology requires the formation and maintenance of the complex membrane structures. Throughout development, aging and other processes including fatigue require constant adaptations of the skeletal muscle system, thus identification and characterization of genes and proteins involved with plasticity in skeletal muscle membrane structures is essential to understand muscle physiology. Thus, structurally MG29 might be seen as a counterpart of synaptophysin in skeletal muscle biogenesis.

MG29 as a sentinel against aging-related dysfunction of Ca homeostasis in skeletal muscle Aging effects on muscle function have been associated with muscle fiber denervation, loss of motor units, and motor unit remodeling. Since functional alterations occur before significant muscle wasting becomes evident, changes in E-C coupling machinery and intracellular Ca homeostasis may act as causative factors for, or adaptive responses to, muscle aging. Altered function of several triad junction proteins, including DHPR, calsequestrin, and SERCA, have been shown to contribute to disrupted Ca homeostasis in aged skeletal muscle. It has been suggested that cumulative uncoupling of the VICR process may be part of the causative and/or adaptive changes during muscle aging. Identification of molecular markers of muscle aging, and their contribution to aging-related muscle dysfunction, has recently emerged as a major focus in E-C coupling studies and geriatric medical research in general.

Extending our initial discovery of Ca sparks in healthy young muscle, we have identified a phenotypic change of Ca spark signaling in aged skeletal muscle. It appears that the plastic nature of Ca sparks in young muscle is compromised in aged skeletal muscle where the duration of the Ca spark response is diminished and cannot be restimulated by additional rounds of osmotic stress. Compromised Ca spark signaling in aged muscle may be linked to the changes in t-tubule/SR membrane structure and/or modification of the SR Ca release machinery, perhaps resulting from aging-related alterations in protein expression.

Using biochemical assays, we found that the expression of MG29 is significantly decreased in aged skeletal muscle. MG29 is essential for maintenance of membrane structure and Ca signaling in skeletal muscle. Abnormalities of membrane ultrastructure around the triad junction were detected in skeletal muscle from both young mg29(–/–) and aged wt mice: the t-tubule was swollen and sometimes missing from the A-I junction, and the SR networks were poorly formed with vacuolated and fragmented structures, leading to misalignment of triad junctions.

In addition to the parallel changes in the membrane structure in young mg29–/– and aged wt muscle, several additional studies suggest that MG29 can be used as a molecular marker for muscle aging. First, the mg29(–/–) mice display muscle weakness at age 6 months or younger, which resembles the atrophic phenotype of aged wt mice. Second, store-operated Ca++entry (SOCE) in aged muscle is significantly down-regulated, which is similar to the dysfunctional properties of SOCE identified in mg29(–/–) neonatal and adult muscles. Third, there appears to be a common phenomenon of segregated Ca releasable pools that exhibit differential sensitivity to EC-coupling in both mg29(–/–) and aged muscle. Our studies illustrate that a segregated Ca pool that cannot be mobilized by the physiological VICR mechanism may exist in both young mg29(–/–) and aged wt muscle fibers. Fourth, we identified a loss of plastic Ca spark signaling in young mg29(–/–) muscles, in a fashion very similar to that seen in aged skeletal muscle. Identification of the compromised Ca sparks signaling and segregated intracellular Ca release may provide unique targets for future therapeutic interventions against the effects of aging on muscle performance.

Discovery of a Role of MG29 in Muscle Fatigue

Considering the extent of disruption to the triad junction membrane ultrastructure in mg29(−/−) animals, the lack of an identifiable function phenotype in non-stressed animals was surprising. We then reasoned that since physiological responses are modified under conditions of stress we needed to investigate the response of mg29(−/−) animals and their muscles under such conditions. Initially, we tested the in vivo response of the whole animal to stress induced by treadmill running exercise. We found that the knockout animals were not able to sustain physical activity for extended periods of time and run significantly less than wild type littermate controls. These studies gave us the initial clues that MG29 was a physiologically relevant molecule with direct roles in muscle performance, particular during increased physical activity. Since physical inactivity may lead to a number of chronic-degenerative diseases, reduced muscle function and muscle wasting, we next investigated the role of MG29 in muscle fatigue.

Muscle fatigue is broadly defined as the decline in ability of a muscle to create force, due to either repetitive or continued activity. Fatigue is a phenomenon experienced by all animals and is thought to be part of a biological control process that limited extended muscle contraction to minimize damage produced by overexertion. Some of the current theories of the cellular mechanisms underlying muscle fatigue include: a) disruption of the effective communication between the T-tubules and $Ca^{2+}$ release from the SR, b) changes in the concentration of sodium or other ions in muscle cell that leads to failure of action potential propagation. c) reactive oxygen species (ROS)/metabolites theory suggests increased muscle activity leads to a net increase in superoxide, hydrogen peroxide and free radicals that can directly modify protein function. This theory is sometimes expanded into a broader concept that postulates that the overall accumulation of metabolites such as ROS, inorganic phosphate, ADP, AMP, etc, buildup during fatigue and cause both a decrease in the amount of $Ca^{2+}$ release from the SR and functional inhibition of the myosin-actin interaction. d) fatiguing stimulation leads to a rise in intracellular $Ca^{2+}$, inducing $Ca^{2+}$ activated proteases and subsequent cleavage of essential E-C coupling related proteins.

While the mechanism at work is not clearly defined, a consensus view in muscle physiology research is that optimal muscle performance revolves around the maintenance of intracellular $Ca^{2+}$ homeostasis, as inadequate $Ca^{2+}$ release from the SR leads to decreased force output. During fatigue, this deficient $Ca^{2+}$ release process could result from improper coupling between the T-tubules and ryanodine receptors (RyR) on the SR membrane, a reduction of the SR $Ca^{2+}$ content, direct modification of RyR function and compromised store-operated $Ca^{2+}$ entry (SOCE).

We investigated the fatigability properties of skeletal muscles from the mg29(−/−) mice using and ex vivo muscle contractility assay and we found that they fatigued to a greater extent, recovered to a lesser extent after fatigue and produced less force, even in the presence of caffeine, than wild type control mice. These findings clearly suggest that E-C coupling in mg29(−/−) skeletal muscle is disrupted. This difference in fatiguing characteristics between muscles from mg29(−/−) and wild type mice was significantly reduced when $Ca^{2+}$ was removed from the extracellular medium and/or when extracellular $Ca^{2+}$ entry was pharmacologically blocked, implicating extracellular $Ca^{2+}$ entry as a major factor in the decreased fatigue resistance in mg29(−/−) muscle.

Extending our initial discovery of Ca sparks in healthy young muscle, we have identified a phenotypic change of Ca spark signaling in aged skeletal muscle. It appears that the plastic nature of Ca sparks in young muscle is compromised in aged skeletal muscle where the duration of the Ca spark response is diminished and cannot be restimulated by additional rounds of osmotic stress. One can expect that compromised Ca spark signaling in aged muscle may be linked to the changes in t-tubule/SR membrane structure and/or modification of the SR Ca release machinery, perhaps resulting from aging-related alterations in protein expression. Using biochemical assays, we found that the expression of MG29 is significantly decreased in aged skeletal muscle (see FIG. 6A). MG29 is essential for maintenance of membrane structure and Ca signaling in skeletal muscle.

Abnormalities of membrane ultrastructure around the triad junction were detected in skeletal muscle from both young mg29(−/−) and aged wt mice: the t-tubule was swollen and sometimes missing from the A-I junction, and the SR networks were poorly formed with vacuolated and fragmented structures, leading to misalignment of triad junctions. Our results indicate that agents, which are capable of modulating the expression and/or activity of MG29 can be useful for the treatment of muscle fatigue, including age-related muscle fatigue as well as muscle fatigue that results due to exercise or exertion or a pathological condition that results in chronic muscle weakness (herein collectively, "muscle fatigue").

Inducible Control of MG29 Expression Transgenic Mice

Figure 1:
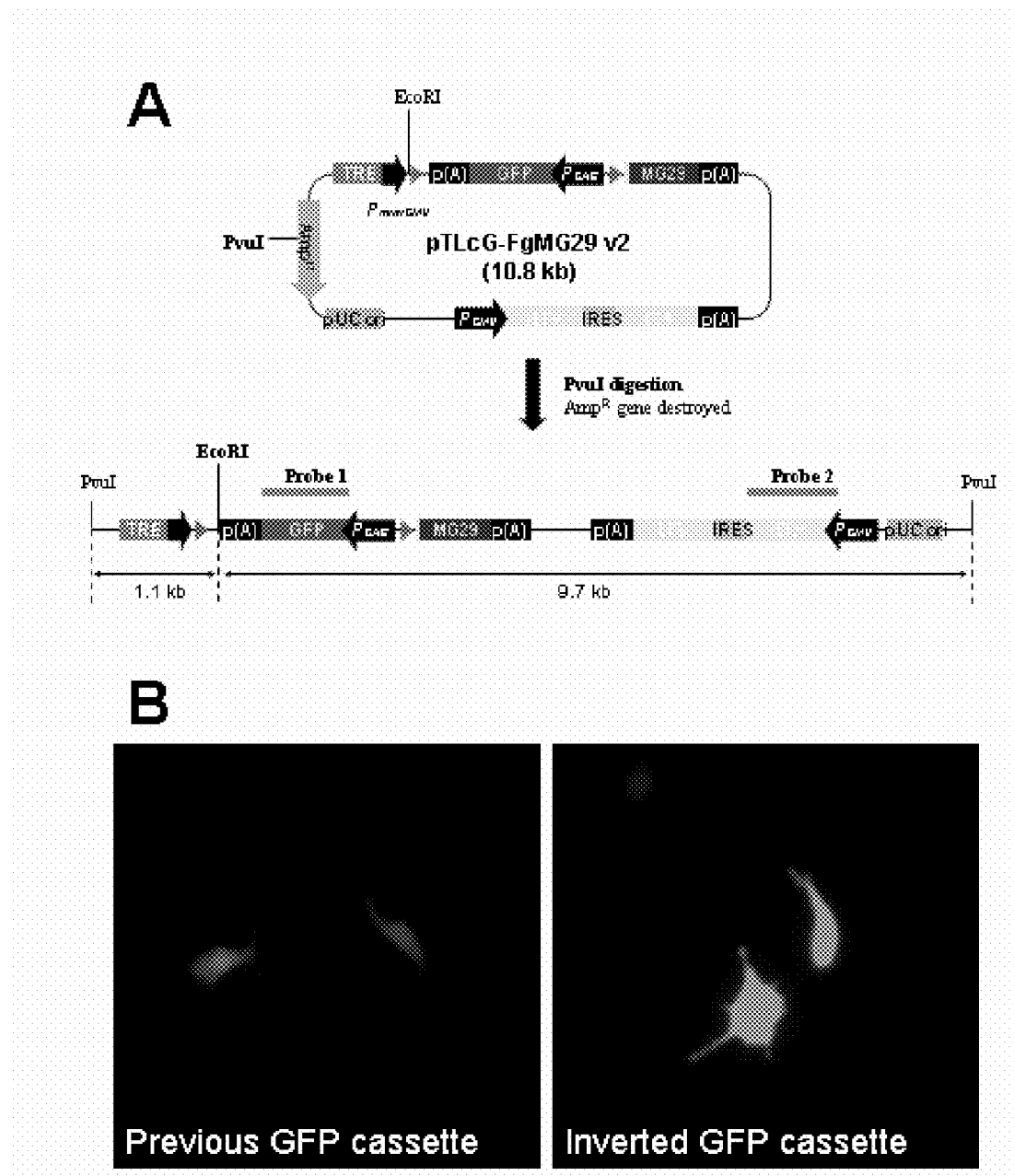
FIG. 1. (A) Novel transgenic system to produce regulated control of MG29 expression. The schematic diagram presents the sequence elements that comprise the transgenic construct that can be used to control expression of various cDNAs, in this case the MG29 cDNA. Resulting transgenic animals can be identified using the detailed probe sequences. Probe 1 targets GFP and is 720 bp long, while Probe 2 targets the rtTA sequence and is 1008 bp long. Genotyping would be done by Southern blot on genomic DNA digested with EcoRI restriction enzyme. (B) Inversion of the GFP cassette relative to the remaining construct results in a significant increase in the fluorescent signal produced when transfected into HEK293 cells (right) when compared to previous versions (left).

To determine if we could control the expression of MG29 at the level of a whole organisms we produced transgenic mice that overexpress MG29 specifically within skeletal muscle under control of an inducible promoter system. We have designed a novel transgenic approach where a dual tetracycline(tet)-inducible system is used to control MG29 expression (FIG. 1A). The transgenic construct contains the mouse mg29 cDNA under the control of a tet responsible minimal CMV promoter. This regulated promoter contains a tet-repressor response element (TRE) that can be bound by either the tet-repressor (tTS)92 and tet-transactivator (rtTA) 93 proteins that are constitutively expressed on a bi-cistronic mRNA under control of a CMV promoter. In the absence of tet, tTS will bind the TRE and inhibit transcription. Once tet is provided in the mouse water supply, tTS disassociates from the TRE and now rtTA can bind to the TRE, allowing robust transcription of mg29 cDNA. The muscle specific nature of this construct is provided by the addition of a GFP cassette flanked by loxP sites between the TRE promoter and the mg29 cDNA. This GFP expression cassette is inverted relative to the rest of the transgenic construct to increase the level of GFP expression (FIG. 1B). The presence of this cassette, and its orientation that positions to cassette promoter in the opposite direction of tet-regulated minimal CMV promoter, will guarantee that MG29 expression will not occur during the generation of founder animals. By breeding these founder lines with αSK-actin(ASKA)-Cre mice94 (obtained from Jackson Laboratories) muscle specific expression is achieved by adding doxycycline, a stable tet analog, to the water supply. Doxycycline will relieve tTS inhibition and induce rtTA activation of MG29 expression.

This transgenic system has the advantage of allowing a tailored, dose dependent regulation of MG29 expression in skeletal muscle, allowing us to more effectively resolve the extent that age-related decrease in MG29 contribute to the complex phenotype of aging. Testing this recombinant system in transfected HEK293 cells we find that the MG29 expression can be controlled by the addition of doxycycline in a dose-dependent manner (FIG. 2A). The timing of gene expression induction can also be tightly regulated by this approach (FIG. 2B). There is an additional advantage that activation of this transgene is reversible, thus we can induce transgene expression, allow remodeling of the triad junction complex and then inhibit the transgene expression. Furthermore, the mg29 cDNA in this system can be replaced with the cDNA for another gene to further expand the utility of this inducible expression system for a variety of applications.

Figure 3:
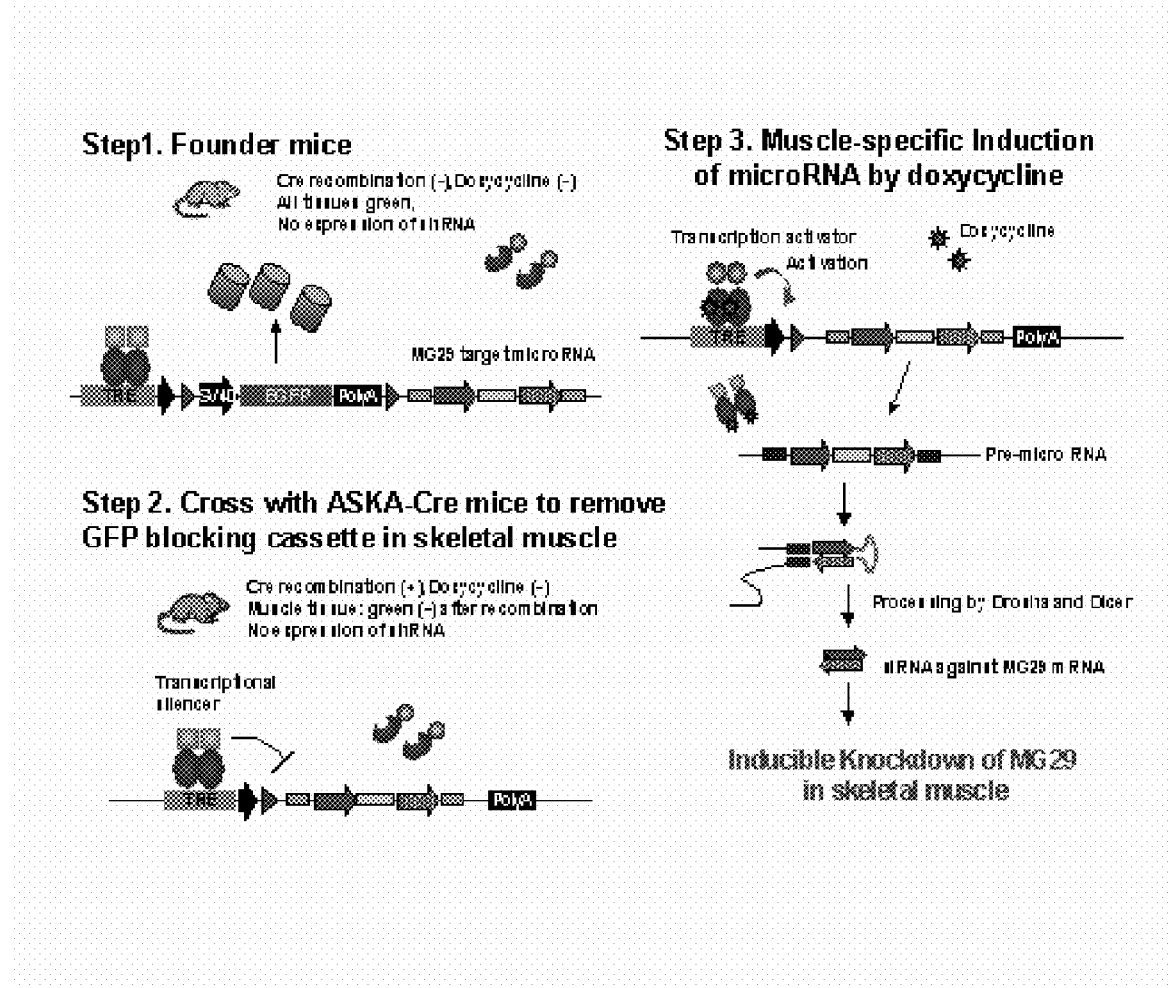
FIG. 3. Novel transgenic system that takes advantage of the tet-ON inducible system to control expression of a microRNA cassette. Application of this approach allows for the generation of founder mice where microRNA expression is specifically restricted to muscle tissues through the application of Cre-recombination technology. Activation of microRNA expression is controlled by the rtTA and tTS proteins of the tet-ON system, allowing for inducible and reversible suppression of expression of the gene of interest FIG. 4. 2nd generation microRNA approach used for inducible knockdown of MG29 gene expression by tet-On system.
Figure 4:
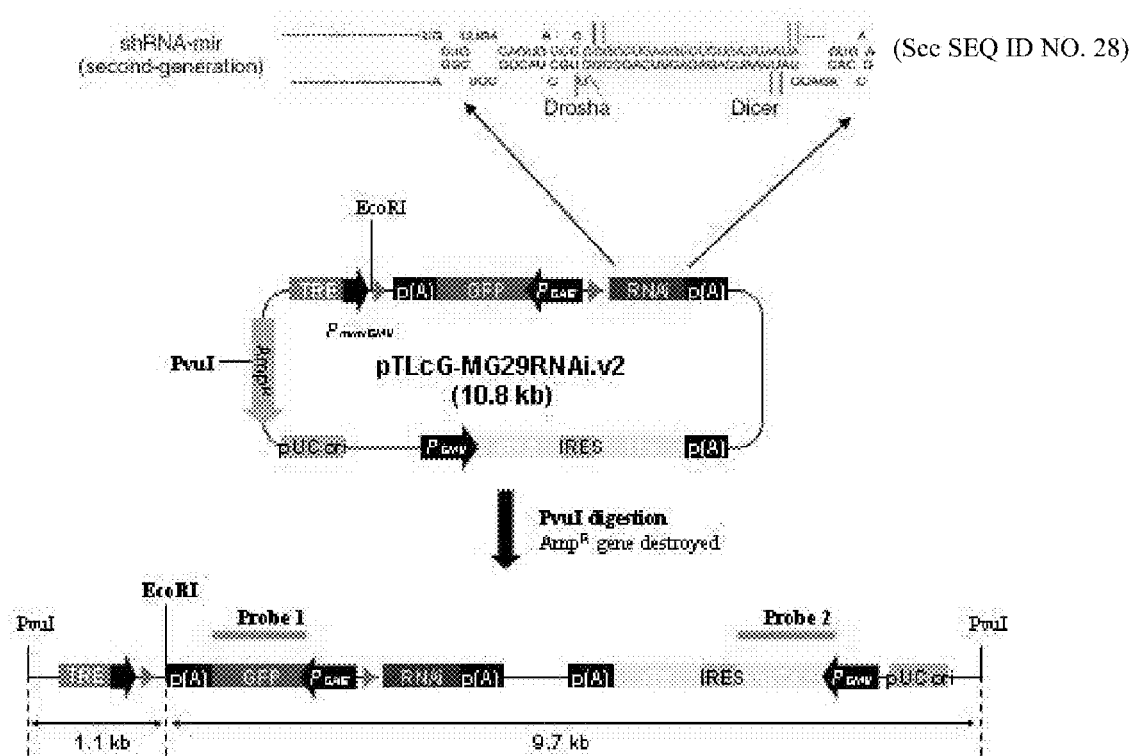

We have further expanded our system to control gene expression by introducing the capacity to reduce gene expression using siRNA-mediated silencing of gene expression. This approach traditionally uses a small hairpin RNA (shRNA) under control of a RNA pol-III promoter (e.g. U6 promoter). Our initial studies showed that this system could not be effectively controlled by inducible expression systems. Thus, we have adapted a system developed by Silva et al (Nature Genetics 37, 1281) that takes advantage of RNA processing by endogenous RNAses Drosha and Dicer to generate microRNA that targets specific mRNA for degradation using a pol-II promoter (e.g. CMV or SV40). Based on this concept, we designed a novel transgenic system that takes advantage of the tet-ON inducible system to control expression of a microRNA cassette (FIG. 3). Application of this approach allows for the generation of founder mice where microRNA expression is specifically restricted to muscle tissues through the application of Cre-recombination technology. Activation of microRNA expression is controlled by the rtTA and tTS proteins of the tet-ON system, allowing for inducible and reversible suppression of expression of the gene of interest (FIG. 4). As a proof-of-concept approach we determined that this transgenic system could be used to repress the expression of two genes, junctophillin-1 (mJP1) and junctophillin-2 (mJP2), in tissue culture in a dose-dependent fashion (FIG. 5). These results indicate the effectiveness of this approach, and also establish that this system can be used to silence the expression of other genes besides MG29.

MG29 Expression Increases with Exercise.

Long-term exercise training has been shown in the past to regulate the expression of a number of genes in skeletal muscle, particular those involved assembly of the contractile apparatus during physiological hypertrophy. However, there are few examples of genes that show significant increases in protein expression levels immediately following fatiguing exercise. During our examination of the role of MG29 in muscle fatigue and sarcopenia, we tested if MG29 expression is modified in mouse skeletal muscle following exercise. We found that MG29 expression levels immediately increase following a single round of treadmill running (FIG. 6B). This increased expression peaked around 24 hours after the treadmill running. Considering that reduced levels of MG29 in the mg29−/− mice or in aged skeletal muscle are linked with diminished muscle performance and increased fatigability, this transient increase in MG29 expression could be an adaptive response in skeletal muscle to acute exercise. Increased MG29 would act to bolster muscle performance and minimize fatigue under these conditions. If MG93 upregulation is part of such a response then inducing a further increased in MG29 expression might be sufficient to provide an additional improvement in skeletal muscle performance.

MG29 Expression Undergoes Post-Transcriptional Regulation.

Considering the remarkable upregulation of MG29 expression following a short bout of treadmill exercise, we sought to better understand the cellular mechanisms that control MG29 expression. During this process, we observed that C2C12 myogenic cells do not express MG29 protein either in the myoblast stage or the differentiated myotube stage (FIG. 7). When C2C12 myoblasts were differentiated into myotubes and harvested at different times no protein expression could be detected by Western blot, however ample MG29 mRNA expression could be detected by real-time PCR. These findings are highly suggestive that there is some level of control of MG29 translation that takes place at the level of the mRNA. If it is possible to resolve the molecular mechanism of this regulation it would provide a method to manipulate MG29 expression as the therapeutic approach against muscle fatigue, and sarcopenia.

The 3' UTR Region in the mg29 cDNA is a Target for Gene Regulation

To understand the molecular mechanism controlling MG20 post-transcriptional regulation we examined the structure of the MG20 mRNA. We found that the 3' UTR in both the mouse and human MG29 mRNA considerably longer than an average 3' UTR for a mRNA in these species (FIG. 8). This would provide additional sequence that could contain primary sequence that could contain binding sites for regulatory factors (see below) or an opportunity for higher-order structures, such as hairpins or other double-stranded motifs, to be generated. By using bioinformatics approaches to resolve the secondary structure of the murine MG29 5' and 3' UTR sequences we found major secondary structure is present in the UTR regions of MG29 (FIGS. 9 and 10). While some hairpin structures are predicted in the 5'UTR, the structure of the 3'UTR is highly complex and provides multiple sites for binding of accessory factors that could affect the post-transcriptional regulation of MG29 gene expression. Thus, the 3' UTR is an excellent candidate for a site where post-transcriptional regulation of MG29 expression could occur.

To facilitate further studies into this phenomenon, we generated two plasmid constructs from MG29 expression experiments (FIG. 11). pFLAG-MG29 is an expression vector that contains only the coding sequence from the murine MG29 gene fused to a FLAG tag (DYKDDDDK). pcDNA-MG29 is a expression vector that contains the full length cDNA and both the 5' and 3' untranslated regions (UTR) of the murine MG29 mRNA. These two constructs allow us to directly test if the UTR of the MG29 mRNA are important in the post-transcriptional regulation of MG29.

While C2C12 cells do not express endogenous MG29 protein, these cells will express MG29 protein when they are transfected with a plasmid that contains the mg29 cDNA that consists of only the coding sequence (FIG. 12). When the plasmid containing the full MG29 mRNA (including UTR) is transfected into the same cells there is no MG29 protein expressed, however there is ample mRNA produced from the plasmid (FIG. 12B). Therefore, the UTR sequence is necessary for the post-transcriptional regulation of MG29 gene expression, revealing the UTR to be a target of the regulatory pathway in muscle that controls the expression of MG29.

To test if this gene regulation pathway is specific to muscle cells, we transfected Human Embryonic Kidney (HEK293) with either pFLAG-MG29 or pcDNA-MG29. In these non muscle cells both constructs produced MG29 mRNA and protein (FIG. 13). However, the presence of MG29 UTR sequences reduced the amount of MG29 protein expression. These findings indicate that the pathway controlling post-transcriptional regulation of MG29 expression is limited in non-muscle cells. While the repression of protein expression in non-muscle HEK293 cells suggests that some ubiquitous factors must participate in this pathway, the appearance of any MG29 protein at all reveals that at least some components controlling the MG29 regulatory pathway must be muscle specific.

The experiments in the previous study (FIG. 13) were performed without the Fetal Bovine Serum (FBS) that would normally be present in the culture media for HEK293 cells. This was done in an effort to mimic the lack of FBS present in the culture media for differentiated C2C12 myoblast cells (in FIG. 12). When FBS is added to HEK293 cells the difference in protein expression between cells transfected with pFLAG-MG29 or pcDNA-MG29 is smaller than it is in the absence of FBS (FIG. 14). These findings are particularly interesting as they suggest that the pathway controlling post-transcriptional MG29 expression can be altered by extracellular signals, likely by protein factors found in the FBS mixture. This means that such factors, or small molecules targeting these or related proteins, could be used to altered MG29 expression as a therapeutic approach.

Thus, it appears there is some characteristic of the native mg29 mRNA, which is not present in the coding sequence cDNA, that prevents the translation of MG29 protein. One candidate for such a regulatory region is the large 3' untranslated region (UTR) of the native mg29 mRNA. Bioinformatic approaches were used to predict the how this 3' UTR sequence would affect the secondary structure. Addition of the 3' UTR sequence on the coding sequence for MG29 creates a much more complex secondary structure and significantly alters the free energy of the molecule (FIGS. 9/10).

While these experiments indicate that the UTR sequences in the MG29 mRNA are the basis for the post-transcriptional regulation of MG29, further analysis of the primary sequence of the 3' UTR of MG29 reveals specific target sites that could participate in gene regulation. There are numerous examples where the UTR of various mRNA can affect the translation of the mRNA. Frequently accessory factors bind onto the UTR and either enhance or repress the translation of the mRNA, while in other cases the secondary structure of the UTR can directly affect mRNA stability. Throughout deletion analysis of the 3'UTR sequence of the mg29 mRNA, we established a specific region within the 3' UTR that was responsible for the post-transcriptional regulation of MG29 expression in muscle cells (FIG. 15). With this information in hand, we used computer database analysis to find such consensus sequences in the MG29 3' UTR that could facilitate this post-transcriptional regulation of MG29 expression (FIG. 16). Three particularly interesting classes of sequences found we the HuR, ARE and 15-LOX-DICE sites. HuR sites regulate the stability and translation of mRNA in response to stress, such as oxidative stress. ARE (AU rich Element) are associated with mRNA destabilization. 15-LOX-DICE (15-LipOXygenase DIfferentiation Control Element) are bound by hnRNP E1 and K to inhibit initiation of translation. ARE (AU rich Element) are involved in mRNA destabilization.

Clearly, MG29 expression is regulated at the post-transcriptional level in a fashion that is dependent on the presence of the UTR of the native MG29 mRNA. Modulation of this regulatory pathway can increase the expression of MG29 in skeletal muscles. This has the potential to act as a therapeutic approach to treat aging-related decline in muscle structure and function; including sarcopenia, atrophy and contractile abnormalities. Since previous studies have linked MG29 protein levels with the capacity to resist muscle fatigue, modulating MG29 expression to produce more protein could also be used as a therapy for disease states that display increased fatigue and/or atrophy, including but not limited to cachexia, heart failure, muscular dystrophy, chronic-obstructive pulmonary disorder (COPD), channelopathies, etc.

There are several methodologies that could be used to target MG29 expression at the post-transcriptional level as a therapeutic approach. An approach targeting processes involved in 3' end processing/capping, exon splicing, addition of polyA tails, mRNA localization, mRNA translation, mRNA stability/degradation and silencing or microRNA (si/miRNA) regulation of the mg29 mRNA could be used a therapeutic approach for various muscle diseases and sarcopenia. Use of complementary or anti-sense RNA sequences, peptides and small chemical molecules represent potential agents to modulate these cellular processes and affect the expression level of MG29 or other genes in the MG29 pathway in muscle cells.

Our results here indicate that mg29 gene expression can be controlled at the post-transcriptional level through a mechanism that targets the UTR sequence in the mg29 mRNA. While this approach provides an attractive novel approach for modulating MG29 protein levels, there are other more established methods for modulating gene expression that can be brought to bear for increasing MG29 protein levels. One such approach is increasing the transcription of mg29 mRNA.

Through a bioinformatics approach, we found that the upstream sequence of the human MG29 gene contains a highly conserved region (FIG. 17). Such a region is expected to comprise the promoter region for the mg29 gene. This conserved region spans nucleotides between −702 to −422 from the transcription initiation site. Highly conserved sequences were found in a number of primate species, including chimpanzee, marmoset and gorilla. This suggests that this region is important in the regulation of mg29 transcription.

To further examine this conserved region for a role in control of mg29 expression we expanded out bioinformatics approach to examine this region for consensus transcription factor binding sites. We found several consensus binding sites associated with muscle atrophy is this conserved region (FIG. 18). Of particular interest were the several sites associated with control of muscle-specific gene expression, including GATA, RUNX1, SREBP1, C/EBP and p300. RUNX1 is of particular interest as it has been directly linked to the progression of muscle atrophy similar to the sarcopenia observed in aged skeletal muscle. A therapeutic approach that targets these or other DNA regulatory elements in the mg29 gene would provide another method for manipulating mg29 expression in the treatment of sarcopenia, muscle fatigue, and other diseases that involve skeletal muscle pathology.

There are several methodologies that could be used to target MG29 expression at the transcriptional level as a therapeutic approach. An approach that alters the chromatin structure of DNA (methylation, acetylation, etc), the specific DNA sequences in the gene promoters region, or the protein factors involved in transcription initiation/elongation (polymerases and other general transcription factors, specificity transcription factors, repressors, and enhancers), of the mg29 gene or other genes with a regulatory role in the MG29 pathway could be used a therapeutic approach for various muscle diseases and sarcopenia. Use of complementary or anti-sense RNA or DNA sequences, peptides and small chemical molecules represent potential agents to modulate these cellular processes and affect the expression level of MG29 in muscle cells.

Methods

Cell transfection—The C2C12 murine myoblast cell line was purchased from the American Type Culture Collection (Manassas, Va.). Cells were grown in a humidified environment at 37° C. and 5% CO2 in DMEM medium for C2C12 or for HEK293 cells supplemented with 10% fetal bovine serum, 100 units/ml penicillin and 100 ug/ml streptomycin. In order to induce myotube differentiation, C2C12 myoblasts were grown to confluence and the medium was switched to DMEM containing 2% horse serum, penicillin (100 U/ml), streptomycin (100·g/ml). For transient transfections, C2C12 myoblasts or HEK293 cells were plated at 70% confluence in glass-bottom dishes or plastic multi-well tissue culture dishes. After 24 hours, cells were transfected with plasmids using GeneJammer reagent (Stratagene) as per manufacturer's directions. Cells were visualized by live cell confocal imaging at 24-48 hours after transfection or at times indicated for individual experiments. Other cells were used for isolation of mRNA or protein to conduct Western blotting and other biochemical experiments. In some experiments, C2C12 myoblasts were allowed to differentiate into myotubes for the indicated time before observation.

Western Blot—Immunoblots were using standard techniques. Briefly, C2C12 or HEK293 cells were harvested and lysed with ice-cold modified RIPA buffer (150 mM NaCl, 5 mM EDTA, 1% NP40, 20 mM Tris-HCl, pH 7.5) in the presence of a cocktail of protease inhibitors (Sigma). 20·g of total protein were separated on a 4-12% SDS-polyacrylamide gel.

Bioinformatics—The sequence 2 kb upstream of the transcription initiation site for the human MG29 gene was used for a BLAST search of the non-repetitive genomic database in GenBank (www.ncbi.nlm.nih.gov/Genbank/). The region at −702 to −422 from the transcription initiation site of the human MG29 gene was subjected to database analysis for consensus transcription factor binding sites (www.cbrc.jp/research/db/TFSEARCH).

Treadmill running—Groups of 6 mice are placed on a leveled Exer-6M rodent treadmill (Columbus Instruments) equipped with an electric grid at the rear and are acclimated for four consecutive days. On day 1, they ran at a speed of 3.8 m/min for 5 min; on day 2, 4.8 m/min for 5 min; on day 3, 5.8 m/min for 5 min; and on day 4, 6.8 m/min for 5 min. On day 5, control and experimental mice run concomitantly at 8.8 m/min until exhaustion as indicated by falling on the electric grid twice, and running times until exhaustion are recorded. Three trials with three control and experimental mice each are conducted for each experimental condition.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims.

The invention claimed is:

1. A method of modulating muscle contractile function comprising administering to a subject in need thereof a composition comprising a pharmaceutically acceptable carrier and an effective amount of an agent that modulates mitsugumin29 (MG29) in a muscle cell, wherein the agent is at least one of (i) a nucleic acid that encodes an MG29 polypeptide, or (ii) a nucleic acid that hybridizes specifically to an MG29 mRNA transcript, and wherein the agent is effective in modulating MG29, and thereby, modulates muscle contractile function.

2. The method of claim 1, wherein the effective amount is from 0.1 mg/kg and 1000 mg/kg body weight/day.

3. The method of claim 1, wherein the composition further includes a nucleic acid that inhibits the expression or activity of an MG29 mRNA binding protein.

4. The method of claim 3, wherein the MG29 mRNA binding protein interacts with either the 5' or the 3' UTR of the MG29 mRNA transcript.

5. The method of claim 1, wherein the MG29 polypeptide is selected from the group consisting of SEQ ID NOs.: 1-20, or a bioactive portion thereof.

6. The method of claim 1, wherein the nucleic acid encoding an MG29 polypeptide demonstrates at least 85% sequence identity to a nucleic acid selected from the group consisting of SEQ ID NOs.: 21-26.

7. The method of claim 1, wherein the nucleic acid of (ii) is an inhibitory RNA or an antisense RNA.

8. The method of claim 7, wherein the inhibitory RNA is a small inhibitory RNA or a microRNA.

9. A method of treating sarcopenia comprising identifying an individual in need thereof, and administering to an individual a composition comprising a pharmaceutically acceptable carrier and an effective amount of an agent that modulates mitsugumin29 (MG29), in a muscle cell, wherein the agent is at least one of (i) a nucleic acid that encodes an MG29 polypeptide, or (ii) a nucleic acid that hybridizes specifically to an MG29 mRNA transcript, and wherein the agent is effective in modulating MG29, and thereby, treats sarcopenia.

10. The method of claim 9, wherein the composition is administered systemically.

11. The method of claim 9, wherein the agent (i) comprises a nucleic acid encoding an MG29 polypeptide as set forth in SEQ ID NOs.: 1-8, or 26.

12. The method of claim 11, wherein the nucleic acid encodes an MG29 polypeptide as set forth in SEQ ID NO:3.

13. The method of claim 9, wherein the composition further includes a nucleic acid that inhibits the expression or activity of an MG29 mRNA binding protein.

14. The method of claim 13, wherein the inhibitory nucleic acid comprises RNA.

15. The method of claim 14, wherein the inhibitory RNA is at least one of an antisense RNA, an interfering RNA or combination of both.

16. The method of claim 15, wherein the interfering RNA is at least one of an siRNA, an miRNA or combination thereof.

* * * * *